(12) United States Patent
Hseih-Wilson et al.

(10) Patent No.: US 7,842,517 B2
(45) Date of Patent: Nov. 30, 2010

(54) METHOD AND COMPOSITIONS FOR THE DETECTION OF PROTEIN GLYCOSYLATION

(75) Inventors: Linda Hseih-Wilson, San Marino, CA (US); Nelly Khidekel, Pasadena, CA (US); Hwan-Ching Tai, Pasadena, CA (US); Sabine Arndt, Dortmund (DE)

(73) Assignee: California Institute of Technology, Pasadena, CA (US)

( * ) Notice: Subject to any disclaimer, the term of this patent is extended or adjusted under 35 U.S.C. 154(b) by 303 days.

(21) Appl. No.: 11/763,834

(22) Filed: Jun. 15, 2007

(65) Prior Publication Data

US 2008/0312424 A1    Dec. 18, 2008

Related U.S. Application Data

(62) Division of application No. 10/990,767, filed on Nov. 17, 2004, now Pat. No. 7,332,355.

(60) Provisional application No. 60/523,523, filed on Nov. 18, 2003.

(51) Int. Cl.
  *G01N 33/532* (2006.01)
  *C07H 19/10* (2006.01)
  *C12Q 1/48* (2006.01)
(52) U.S. Cl. .................. 436/544; 435/15; 536/26.8
(58) Field of Classification Search .................. None
  See application file for complete search history.

(56) References Cited

U.S. PATENT DOCUMENTS 6,197,599 B1    3/2001    Chin et al.

OTHER PUBLICATIONS

Lazarevic et al. Syntheses of unnatural N-substituted UDP-galactosamines as alternative substrates for N-acetylgalactosaminyl transfereses. Carbohydrate Research 2002, vol. 337, pp. 2187-2194.*
Losey et al. Incorporation of glucose analogs by GtfE and GtfD from the vancomycin biosynthesis pathway to generate varient glycopeptides. Chemistry & Biology 2002, vol. 9, pp. 1305-1314.*

Lasky, L. A., "Selection—Carbohydrate Interactions and the Initiation of the Inflammatory Response," Anna. Rev. Biochem., 1995, 64, 113-139.
Capila, I., et al, "Heparin—Protein Interactions," Angew. Chem., Int. Ed. 2002, 41, 391-412.
Rudd, P. M., et al., "Glycosylation and the Immune System," Science 2001, 291, 2370-2376.
Wells, L., et al, "Glycosylation of Nucleocytoplasmic Proteins: Signal Transduction and O-GlcNAc," Science 2001, 291, 2376-2378.
Zachara, N. E., et al., "The Emerging Significance of O-GlcNAc in Cellular Regulation,", G. W. Chem. Rev. 2002, 102, 431.
Roquemore, E. P., et al., "Detection of 0-Linked N-Acetylglucosamine (O-GlcNAc) on Cytoplasmic and Nuclear Proteins," Methods Enzymol. 1994, 230, 443-460.
Snow, C. M, et al., "Monoclonal Antibodies Identify a Group of Nuclear Pore Complex Glycoproteins,". Cell Biol. 1987, 104, 1143-1156.
Comer, F. I, et al., Characterization of a Mouse Monoclonal Antibody Specific for O-Linked N-Acetylglucosamine, . Anal. Biochem. 2001, 293, 169-177.
Varki, A., "Biological Roles of Oligosaccharides: All of the Theories are Correct," Glycobiology 1993, 3, 97-130.

* cited by examiner

*Primary Examiner*—Shafiqul Haq
(74) *Attorney, Agent, or Firm*—Buchanan Ingersoll & Rooney PC

(57) ABSTRACT

The invention provides methods and compositions for the rapid and sensitive detection of post-translationally modified proteins, and particularly of those with post-translational glycosylations. The methods can be used to detect O-GlcNAc posttranslational modifications on proteins on which such modifications were undetectable using other techniques. In one embodiment, the method exploits the ability of an engineered mutant of β-1,4-galactosyltransferase to selectively transfer an unnatural ketone functionality onto O-GlcNAc glycosylated proteins. Once transferred, the ketone moiety serves as a versatile handle for the attachment of biotin, thereby enabling detection of the modified protein. The approach permits the rapid visualization of proteins that are at the limits of detection using traditional methods. Further, the preferred embodiments can be used for detection of certain disease states, such as cancer, Alzheimer's disease, neurodegeneration, cardiovascular disease, and diabetes.

7 Claims, 30 Drawing Sheets time (min)

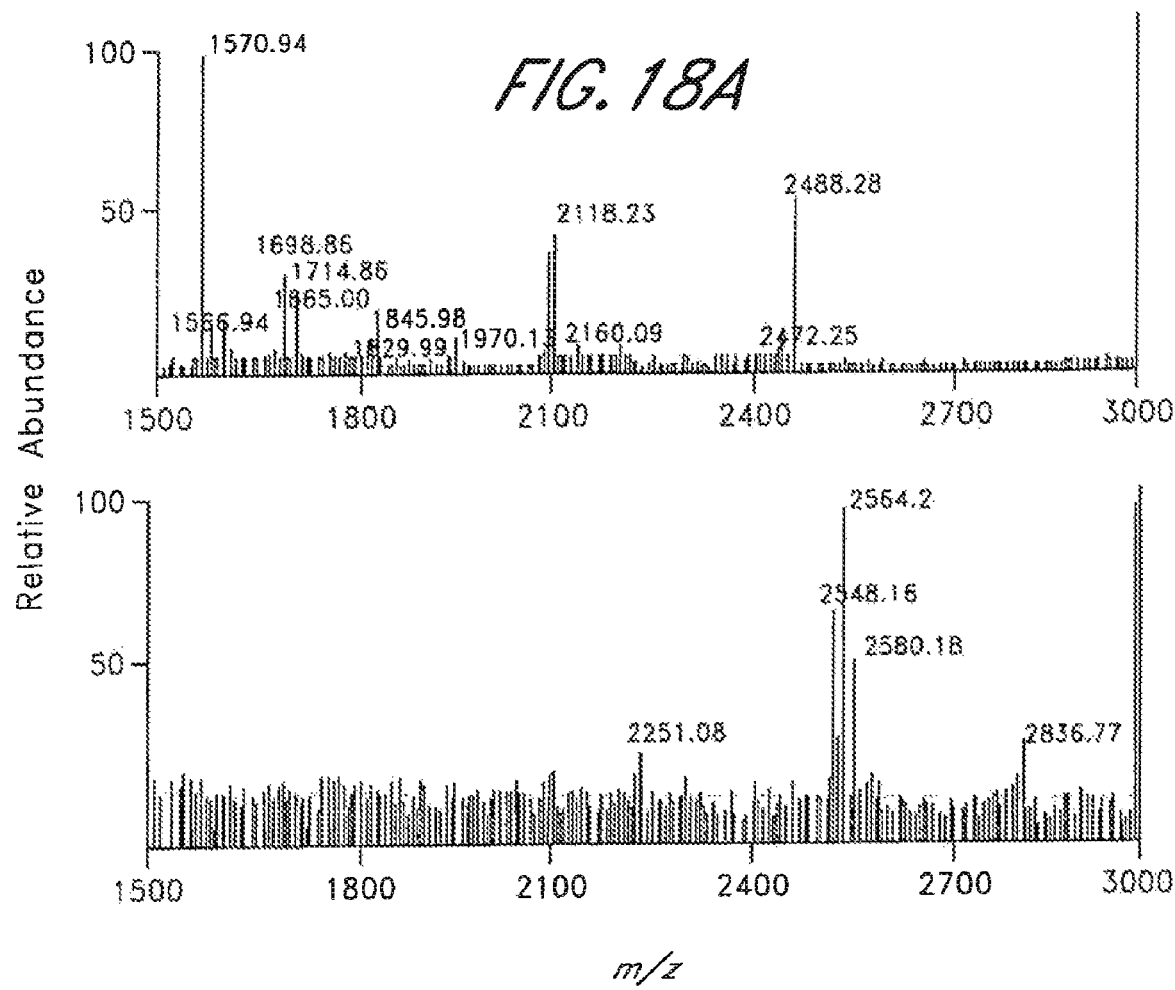

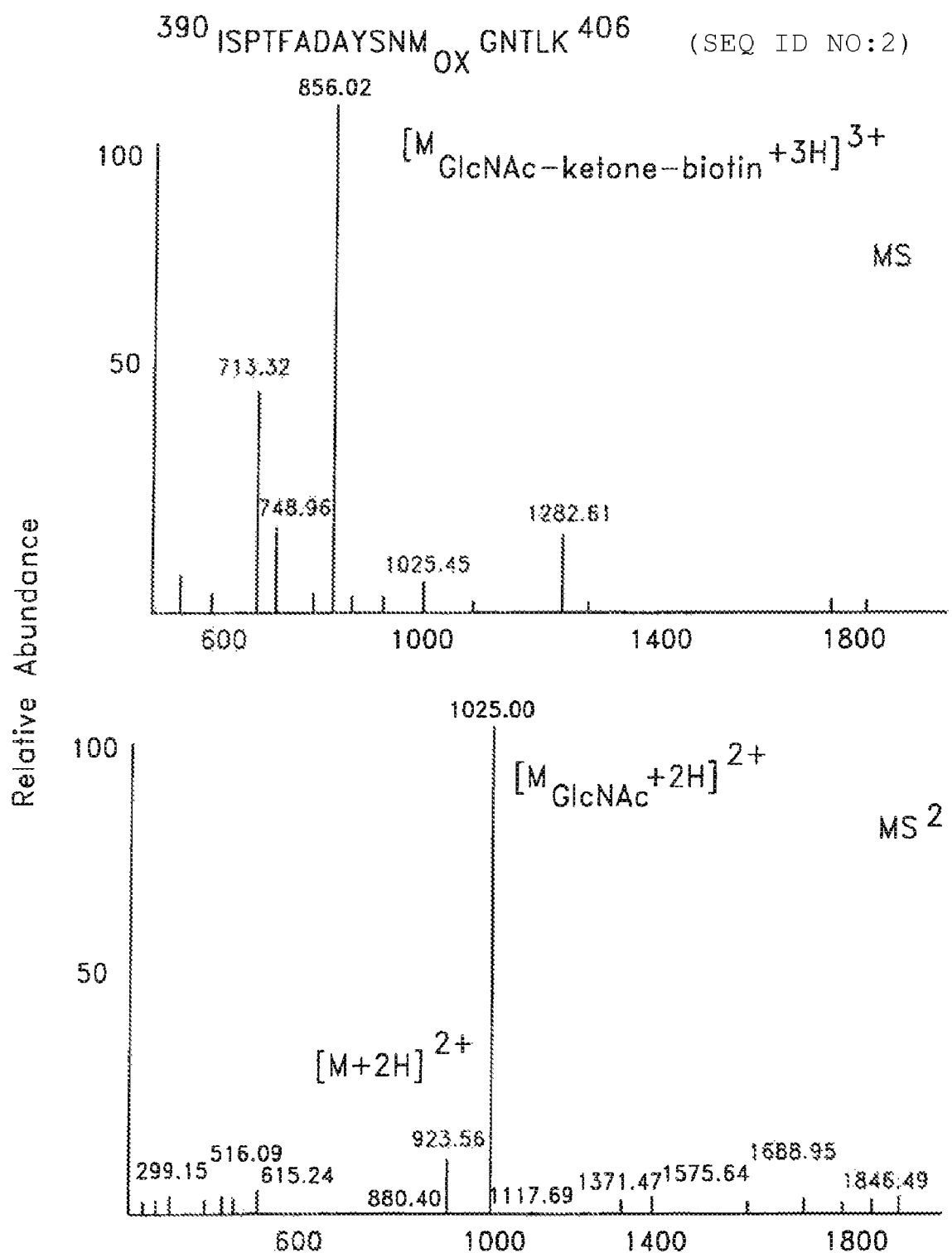
FIG.20A₁

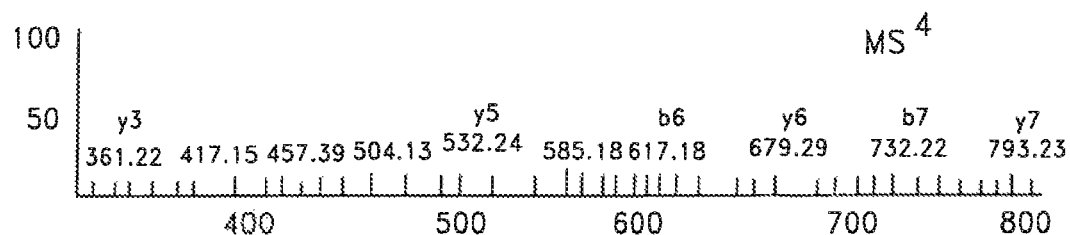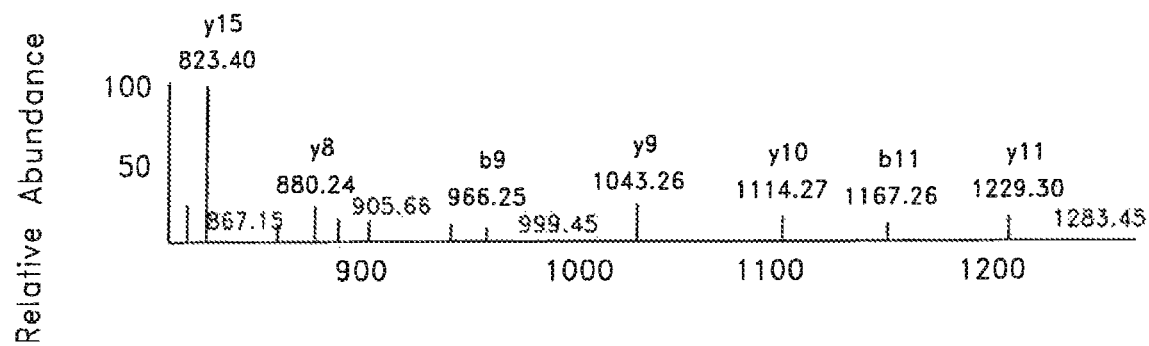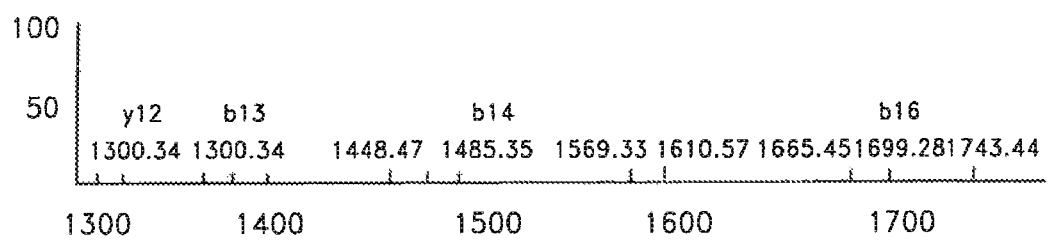
FIG.20A₂

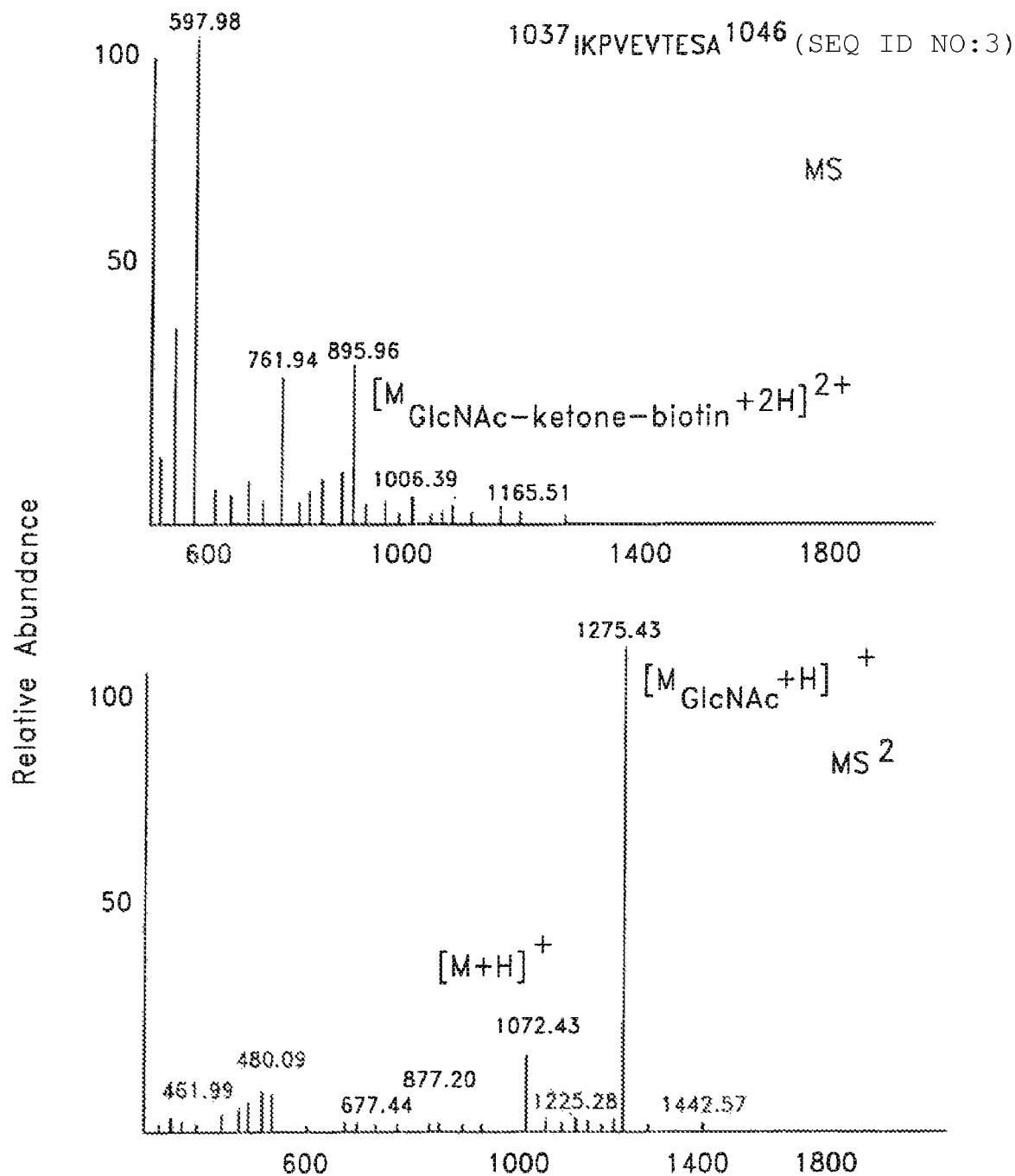
FIG.20B₁

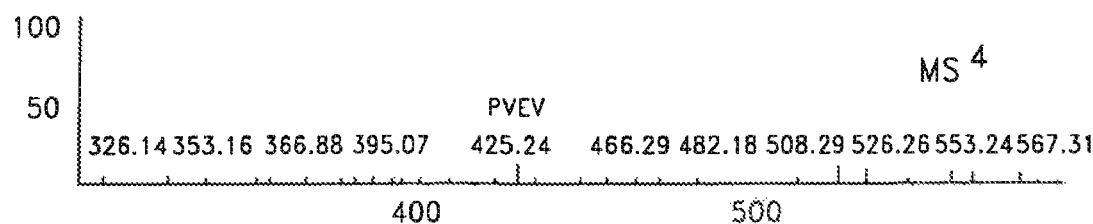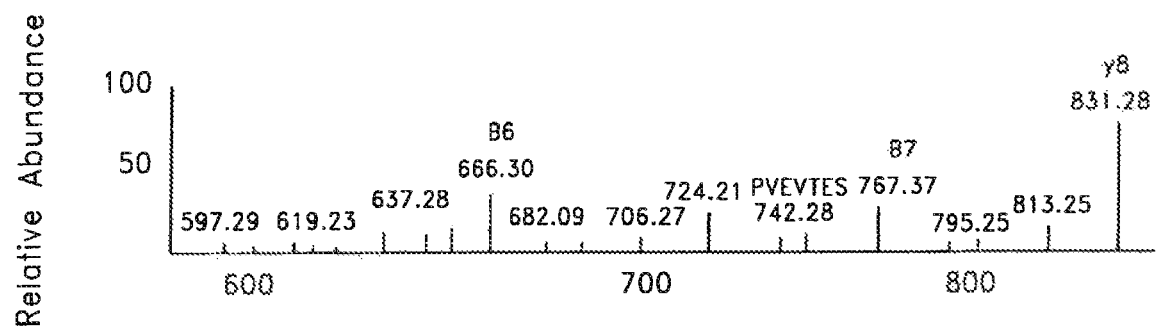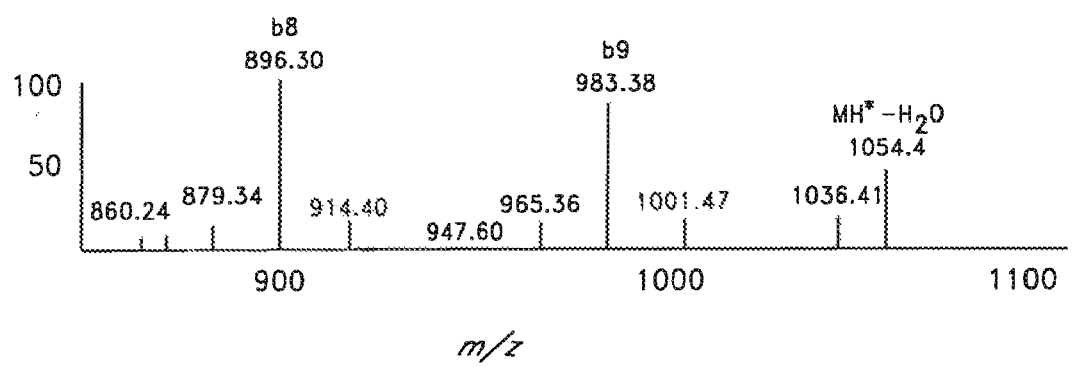
FIG.20B₂

FIG.23A
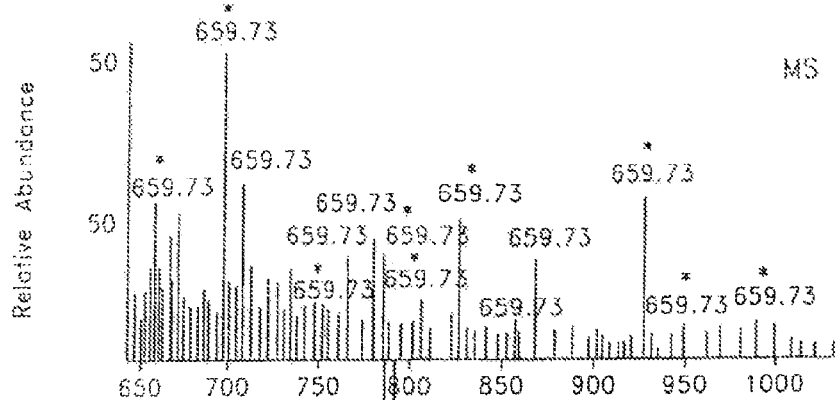
FIG.23B
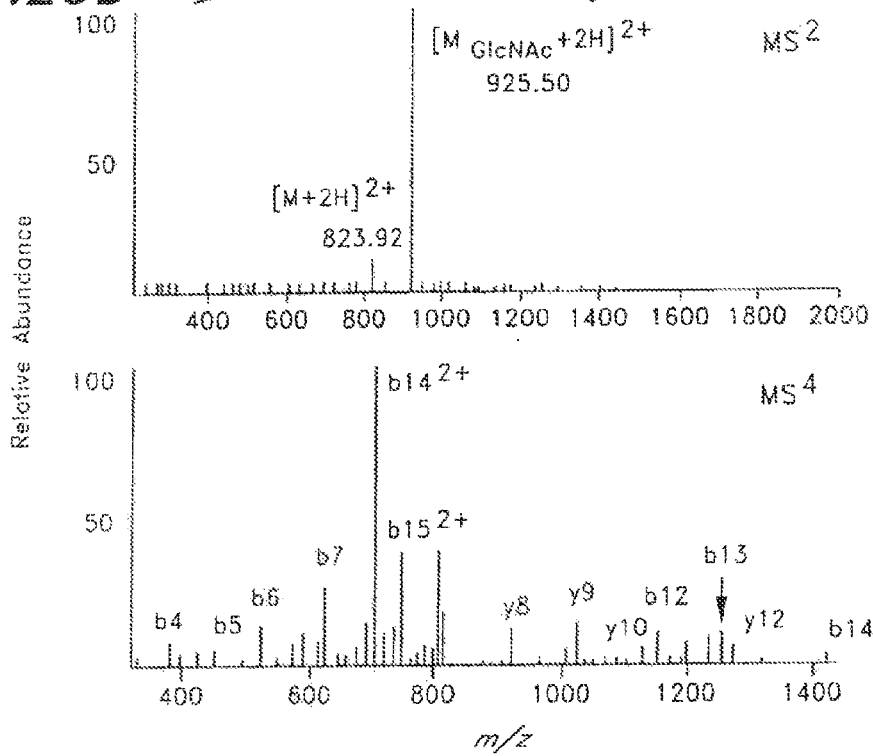
FIG.23C

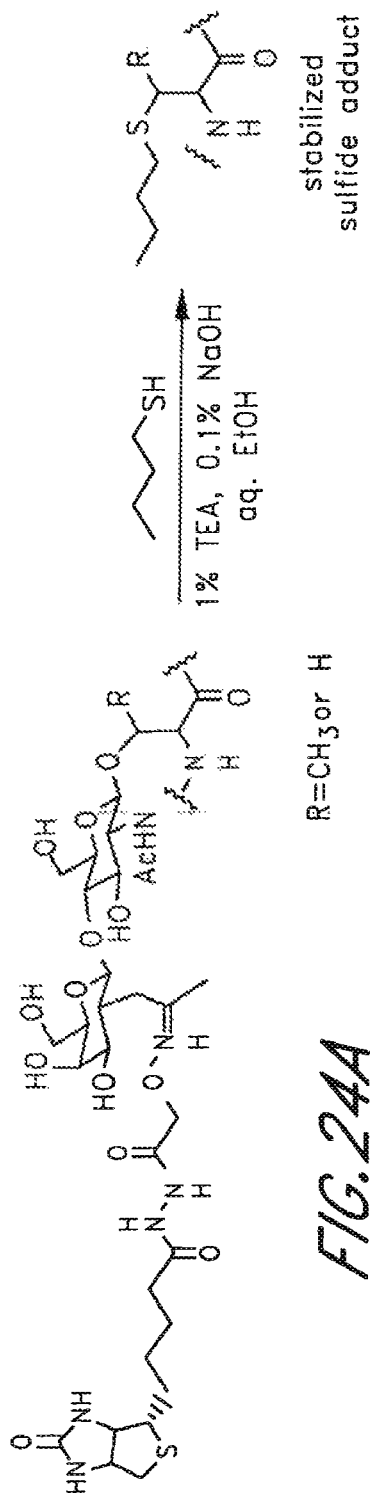
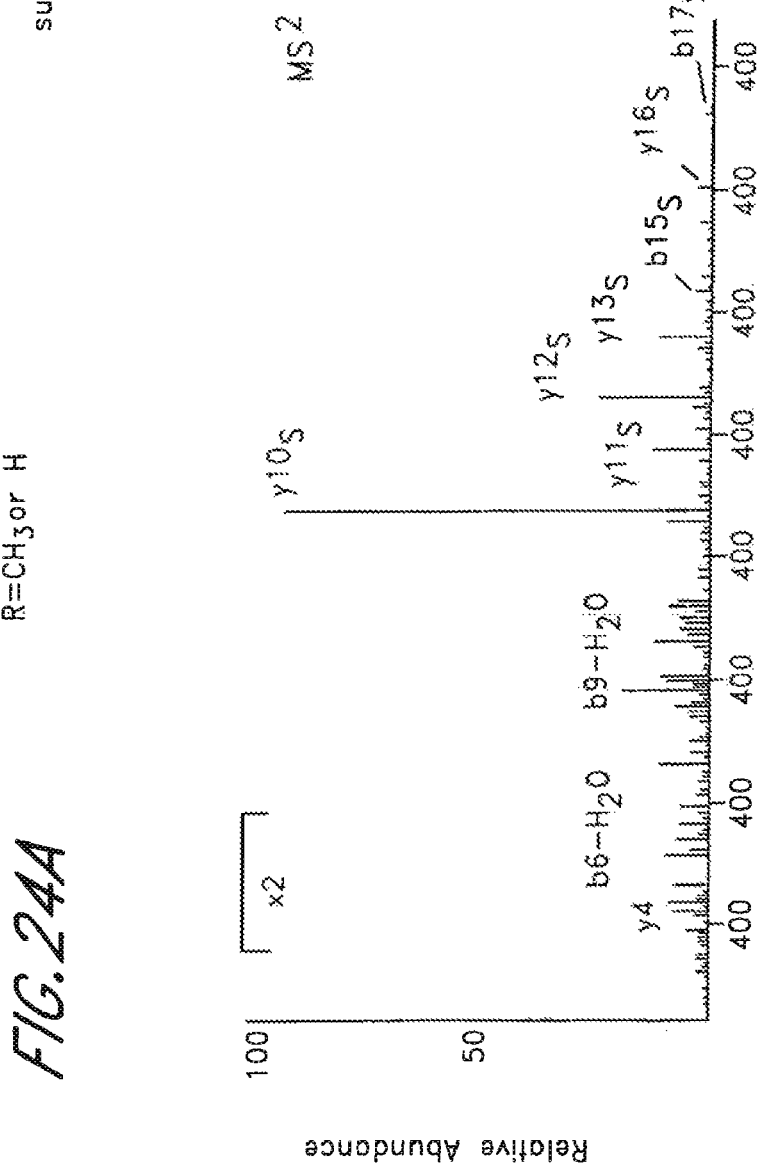
FIG.24A
FIG.24B

FIG. 24D b-ions
360 A P V G S V V S P S H S S A S S D K 378
         b6-H₂O b9-H₂O      b15s  b17s
y16s  y13s y12s y11s y10s y7s   y4
y-ions (SEQ ID NO: 6)

▓▓▓ Transcriptional Regulation
▓▓▓ Intracellular Transport
▓▓▓ Nucleic Acid Binding Proteins
▓▓▓ Cellular Organization/Dynamics
▓▓▓ Cellular Communication/Signal Transduction
▓▓▓ Uncharacterized Proteins

US 7,842,517 B2

METHOD AND COMPOSITIONS FOR THE DETECTION OF PROTEIN GLYCOSYLATION

CROSS REFERENCE TO RELATED APPLICATIONS

This is a divisional of U.S. patent Ser. No. 10/990,767, filed 17 Nov. 2004, which claims priority under 35 U.S.C. §119(e) to U.S. Provisional Patent No. 60/523,523, filed 18 Nov. 2003, which are herein incorporated by reference.

STATEMENT REGARDING FEDERALLY SPONSORED RESEARCH

This invention was made in part with government support under the NSF CAREER Award (CHE-0239861) awarded by the National Science Foundation and under the National Institutes of Health Training Grant T32GM07616 awarded by the National Institutes of Health. The Government may have certain rights in this invention.

BACKGROUND OF THE INVENTION

1. Field of the Invention

The invention relates to labeling, detecting, and/or isolating proteins with post-translational modifications.

2. Description of the Related Art

Protein glycosylation is one of the most abundant post-translational modifications and plays a fundamental role in the control of biological systems. For example, carbohydrate modifications are important for host-pathogen interactions, inflammation, development, and malignancy.(1) One such covalent modification is O-GlcNAc glycosylation, which is the covalent modification of serine and threonine residues by β-N-acetylglucosamine.(2) The O-GlcNAc modification is found in all higher eukaryotic organisms from *C. elegans* to man and has been shown to be ubiquitous, inducible and highly dynamic, suggesting a regulatory role analogous to phosphorylation. However, the regulatory nature of the modification (i.e., dynamic, low cellular abundance) also represents a central challenge in its detection and study.

A common method to observe O-GlcNAc involves labeling proteins with β-1,4-galactosyltransferase (GalT), an enzyme that catalyzes the transfer of [$^3$H]-Gal from UDP-[$^3$H]galactose to terminal GlcNAc groups.(3) Unfortunately, this approach is expensive, involves handling of radioactive material, and requires exposure times of days to months. Antibodies (4,5) and lectins (3) offer alternative means of detection, but they can suffer from weak binding affinity and limited specificity.

SUMMARY OF THE INVENTION

Accordingly, there is a need for methods of labeling and detecting proteins with post-translational modifications, particularly glycosylated proteins. The preferred embodiments provided herein address these and other needs in the art.

The preferred embodiments provide methods and compositions for labeling, for detection of, or other purposes, post-translationally modified proteins.

One embodiment comprises a method for detecting a post-translationally modified protein with a pendant moiety comprising contacting the protein with a labeling agent capable of reacting with the pendant moiety in the presence of an enzyme, wherein the labeling agent comprises a chemical handle; and reacting the chemical handle with a detection agent; and detecting the detection agent.

The method in the preceding paragraph in which the pendant moiety is a glycosyl group.

The method in the preceding paragraph in which the glycosyl group is selected from the group consisting of glucose, galactose, mannose, fucose, GalNAc, GlcNAc and NANA.

The method in the preceding paragraph in which the glycosyl group is GlcNAc.

The method described four paragraphs above in which the enzyme is a glycosyl transferase.

The method in the preceding paragraph in which the glycosyl transferase is GalT or a mutant thereof.

The method described six paragraphs above in which the detection agent is selected from the group consisting of fluorescent reagent, enzymatic reagent that can convert substrates calorimetrically or fluorometrically, fluorescent and luminescent probe, metal-binding probe, protein-binding probe, probe for antibody-based binding, radioactive probe, photocaged probe, spin-label or spectroscopic probe, heavy-atom containing probe, polymer containing probe, probe for protein cross-linking, and probe for binding to particles or surfaces that contain complementary functionality.

The method described seven paragraphs above in which the detection agent recruits another agent selected from the group consisting of a labeling agent, an enzyme, and a secondary detection agent.

The method in the preceding paragraph in which the detection agent is biotin or biotin derivative.

The method in the preceding paragraph in which biotin recruits a secondary detection agent selected from the group consisting of fluorescent reagent, enzymatic reagent that can convert substrates colorimetrically or fluorometrically, fluorescent and luminescent probe, metal-binding probe, protein-binding probe, probe for antibody-based binding, radioactive probe, photocaged probe, spin-label or spectroscopic probe, heavy-atom containing probe, polymer containing probe, probe for protein cross-linking, and probe for binding to particles or surfaces that contain complementary functionality.

The method described ten paragraphs above in which the chemical handle is selected from the group consisting of carbonyl group, azide group, alkyne group, and olefin group.

The method in the preceding paragraph in which the chemical handle is a carbonyl group.

The method in the preceding paragraph in which the detection agent comprises a reactive group selected from the group consisting of —NR$^1$—NH$_2$ (hydrazide), —NR$^1$(C=O)NR$^2$NH$_2$ (semicarbazide), —NR$^1$(C=S)NR$^2$NH$_2$ (thiosemicarbazide), —(C=O)NR$^1$NH$_2$ (carbonylhydrazide), —(C=S)NR$^1$NH$_2$ (thiocarbonylhydrazide), —(SO$_2$)NR$^1$NH$_2$ (sulfonylhydrazide), —NR$^1$NR$^2$(C=O)NR$^3$NH$_2$ (carbazide), —NR$^1$NR$^2$(C=S)NR$^3$NH$_2$ (thiocarbazide), and —O—NH$_2$ (aminooxy), wherein each R$^1$, R$^2$, and R$^3$ is independently H or alkyl having 1-6 carbons.

The method in the preceding paragraph in which the detection agent comprises a reactive group selected from the group consisting of hydrazide, aminooxy, semicarbazide, carbohydrazide, and sulfonylhydrazide.

The method described fourteen paragraphs above in which the detecting step is achieved by a means selected from the group consisting of radioactively, chemiluminescent, fluorescent, mass spectrometric, spin-labeling, and affinity labeling.

One embodiment comprises a method for detecting a post-translationally modified protein with a pendant moiety comprising contacting the protein with a labeling agent of the formula

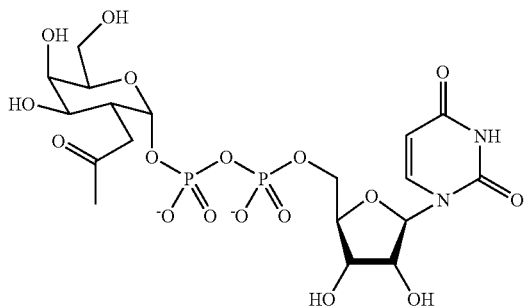

in the presence of GalT or a mutant of GalI, thereby producing labeled protein; and reacting the labeled protein with a detection agent; and detecting the detection agent.

The method in the preceding paragraph in which the pendant moiety is a glycosyl group.

The method in the preceding paragraph in which the glycosyl group is selected from the group consisting of glucose, galactose, mannose, fucose, GalNAc, GlcNAc and NANA.

The method in the preceding paragraph in which the glycosyl group is GlcNAc.

The method described four paragraphs above in which the GalT is mutated with Y289L.

The method described five paragraphs above in which the detection agent is selected from the group consisting of fluorescent reagent, enzymatic reagent that can convert substrates calorimetrically or fluorometrically, fluorescent and luminescent probe, metal-binding probe, protein-binding probe, probe for antibody-based binding, radioactive probe, photocaged probe, spin-label or spectroscopic probe, heavy-atom containing probe, polymer containing probe, probe for protein cross-linking, and probe for binding to particles or surfaces that contain complementary functionality.

The method described six paragraphs above in which the detection agent recruits another agent selected from the group consisting of a labeling agent, an enzyme, and a secondary detection agent.

The method in the preceding paragraph in which the detection agent is biotin or biotin derivative.

The method in the preceding paragraph in which biotin recruits a secondary detection agent selected from the group consisting of fluorescent reagent, enzymatic reagent that can convert substrates colorimetrically or fluorometrically, fluorescent and luminescent probe, metal-binding probe, protein-binding probe, probe for antibody-based binding, radioactive probe, photocaged probe, spin-label or spectroscopic probe, heavy-atom containing probe, polymer containing probe, probe for protein cross-linking, and probe for binding to particles or surfaces that contain complementary functionality.

The method described nine paragraphs above in which the detection agent comprises a reactive group selected from the group consisting of —$NR^1$—$NH_2$ (hydrazide), —$NR^1$(C=O)$NR^2NH_2$ (semicarbazide), —$NR^1$(C=S)$NR^2NH_2$ (thiosemicarbazide), —(C=O)$NR^1NH_2$ (carbonylhydrazide), —(C=S)$NR^1NH_2$ (thiocarbonylhydrazide), —($SO_2$)$NR^1NH_2$ (sulfonylhydrazide), —$NR^1NR^2$(C=O)$NR^3NH_2$ (carbazide), —$NR^1NR^2$(C=S)$NR^3NH_2$ (thiocarbazide), and —O—$NH_2$ (hydroxylamine), wherein each $R^1$, $R^2$, and $R^3$ is independently H or alkyl having 1-6 carbons.

The method described ten paragraphs above in which the detection agent comprises a reactive group selected from the group consisting of hydrazide, hydroxylamine, semicarbazide, carbohydrazide, and sulfonylhydrazide.

The method described eleven paragraphs above in which the detecting step is achieved by a means selected from the group consisting of radioactively, chemiluminescent, fluorescent, mass spectrometric, spin-labeling, and affinity labeling.

One embodiment comprises a compound of the formula:

Genus A

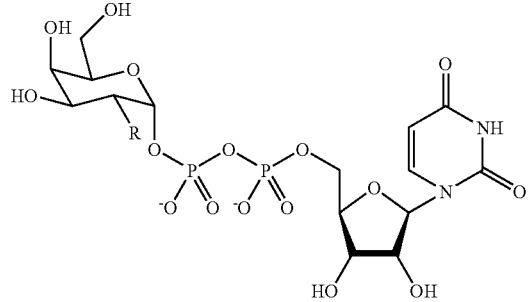

wherein R is a substituent selected from the group consisting of straight chain or branched $C_1$-$C_{12}$ carbon chain bearing a carbonyl group, azide group, straight chain or branched $C_1$-$C_{12}$ carbon chain bearing an azide group, straight chain or branched $C_1$-$C_{12}$ carbon chain bearing an alkyne, and straight chain or branched $C_1$-$C_{12}$ carbon chain bearing an alkene.

The compound in the preceding paragraph in which R is selected from the group consisting of straight chain or branched $C_2$-$C_4$ carbon chain bearing a carbonyl group, azide group, straight chain or branched $C_2$-$C_4$ carbon chain bearing an azide group, straight chain or branched $C_2$-$C_4$ carbon chain bearing an alkyne, and straight chain or branched $C_2$-$C_4$ carbon chain bearing an alkene.

The compound described two paragraphs above in which the formula is

1

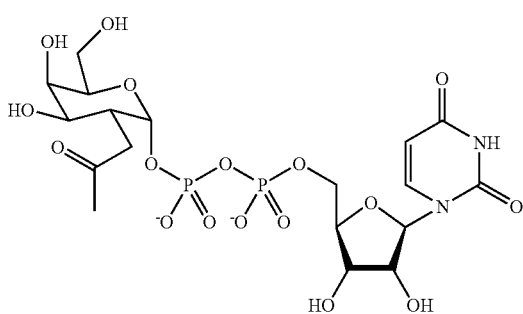

One embodiment comprises a labeled protein obtained from contacting a post-translationally modified protein comprising a pendant moiety with a labeling agent capable of reacting with the pendant moiety in the presence of an enzyme, wherein the labeling agent comprises a chemical handle; and reacting the chemical handle with a detection agent.

The labeled protein described in the preceding paragraph in which the pendant moiety is a glycosyl group.

The labeled protein described in the preceding paragraph in which the glycosyl group is selected from the group consisting of glucose, galactose, mannose, fucose, GalNAc, GlcNAc and NANA.

The labeled protein described in the preceding paragraph in which the glycosyl group is GlcNAc.

The labeled protein described four paragraphs above in which the enzyme is a glycosyl transferase.

The labeled protein described in the preceding paragraph in which the glycosyl transferase is GalT or a mutant thereof.

The labeled protein described six paragraphs above in which the detection agent is selected from the group consisting of fluorescent reagent, enzymatic reagent that can convert substrates calorimetrically or fluorometrically, fluorescent and luminescent probe, metal-binding probe, protein-binding probe, probe for antibody-based binding, radioactive probe, photocaged probe, spin-label or spectroscopic probe, heavy-atom containing probe, polymer containing probe, probe for protein cross-linking, and probe for binding to particles or surfaces that contain complementary functionality.

The labeled protein described seven paragraphs above in which the detection agent recruits another agent selected from the group consisting of a labeling agent, an enzyme, and a secondary detection agent.

The labeled protein described in the preceding paragraph in which the detection agent is biotin or biotin derivative.

The labeled protein described in the preceding paragraph in which biotin recruits a secondary detection agent selected from the group consisting of fluorescent reagent, enzymatic reagent that can convert substrates colorimetrically or fluorometrically, fluorescent and luminescent probe, metal-binding probe, protein-binding probe, probe for antibody-based binding, radioactive probe, photocaged probe, spin-label or spectroscopic probe, heavy-atom containing probe, polymer containing probe, probe for protein cross-linking, and probe for binding to particles or surfaces that contain complementary functionality.

The labeled protein described ten paragraphs above in which the chemical handle is selected from the group consisting of carbonyl group, azide group, alkyne group, and olefin group.

The labeled protein described in the preceding paragraph in which the chemical handle is a carbonyl group.

The labeled protein described in the preceding paragraph in which the detection agent comprises a reactive group selected from the group consisting of —NR$^1$—NH$_2$ (hydrazide), —NR$^1$(C=O)NR$^2$NH$_2$ (semicarbazide), —NR$^1$(C=S)NR$^2$NH$_2$ (thiosemicarbazide), —(C=O)NR$^1$NH$_2$ (carbonylhydrazide), —(C=S) NR$^1$NH$_2$ (thiocarbonylhydrazide), —(SO$_2$)NR$^1$NH$_2$ (sulfonylhydrazide), —NR$^1$NR$^2$(C=O)NR$^3$NH$_2$ (carbazide), —NR$^1$NR$^2$(C=S)NR$^3$NH$_2$ (thiocarbazide), and —O—NH$_2$ (aminooxy), wherein each R$^1$, R$^2$, and R$^3$ is independently H or alkyl having 1-6 carbons.

The labeled protein described two paragraphs above in which the detection agent comprises a reactive group selected from the group consisting of hydrazide, aminooxy, semicarbazide, carbohydrazide, and sulfonylhydrazide.

BRIEF DESCRIPTION OF THE DRAWINGS

FIG. 18 shows enrichment of OGT O-GlcNAc peptides via the chemoenzymatic labeling strategy: (A) MALDI-TOF spectrum of OGT tryptic peptides prior to avidin chromatography reveals a number of OGT peptides while no labeled O-GlcNAc modified peptides are visible, and (B) MALDI-TOF spectrum of eluted peptides following avidin affinity chromatography reveals enrichment of a peak at m/z 2548.16 and two oxidized forms of the same peptide.

FIG. 20 shows identification of O-GlcNAc modified peptides on OGT by LC-MS/MS: (A) tandem mass spectra of the labeled O-GlcNAc peptide $^{390}$ISPTFADAYSN-MoxGNTLK$^{406}$ (SEQ ID NO: 2) (m/z 856.02), and (B) tandem mass spectra of the labeled O-GlcNAc peptide $^{1037}$IKPVEVTESA$^{1046}$ (SEQ ID NO: 3) (m/z 895.96).

FIG. 23 shows (A) summed m/z spectrum of ions eluting from the LC column with retention time 17.0 to 18.1 minutes, (B) MS/MS spectrum of a representative peak (m/z=789.23), showing loss of a ketone-biotin moiety (m/z=925.50) and GlcNAc-ketone-biotin moiety (m/z 823.92), and (C) prominent fragment ions used to identify the peptide as $^{203}$VSGHAAVTTPKVYSE$^{218}$ (SEQ ID NO: 5) from synaptopodin.

DETAILED DESCRIPTION OF THE PREFERRED EMBODIMENT

The preferred embodiments provide methods and compositions for labeling for detection or other purposes, post-translationally modified proteins. An embodiment comprises a labeled protein obtained from contacting a post-translationally modified protein comprising a pendant moiety with a labeling agent capable of reacting with the pendant moiety in the presence of an enzyme, wherein the labeling agent comprises a chemical handle; and reacting the chemical handle with a detection agent. Further, the preferred embodiments can be used for detection of certain disease states, such as cancer, Alzheimer's disease, neurodegeneration, cardiovascular disease, and diabetes.

Figure 1A:
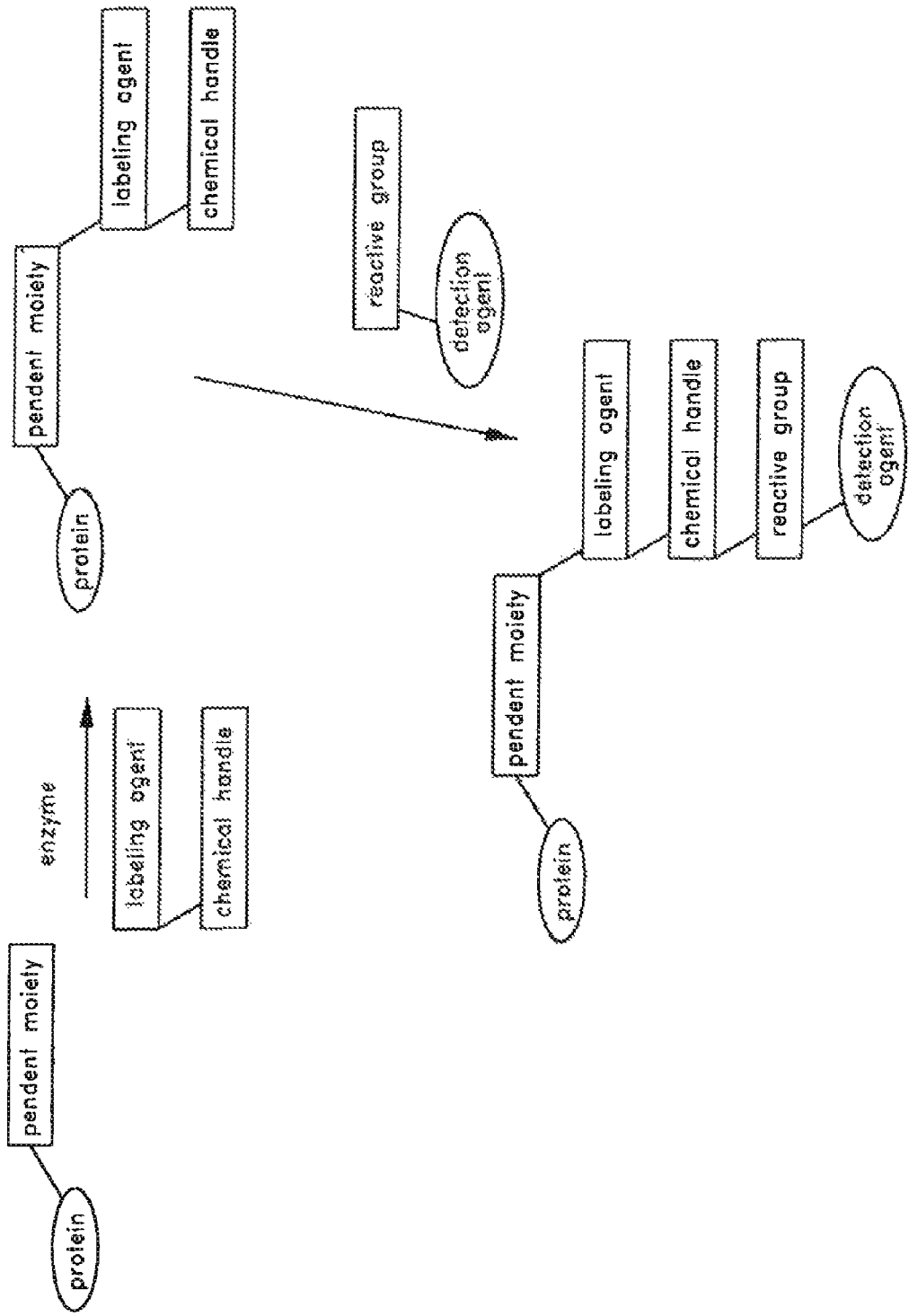
FIG. 1A shows a general scheme of detecting post-translationally modified proteins comprising a pendant moiety.

As set forth generally in FIG. 1A, the methods of the preferred embodiments involve contacting a protein or mixture of proteins further comprising a pendant moiety with a labeling agent capable of reacting with the pendant moiety on the protein. An enzyme can transfer the labeling agent or portion thereof to the pendant moiety on the protein. A modified protein results from reaction of the labeling agent with the pendant moiety of the protein. In one embodiment, the pendant moiety is a carbohydrate moiety. When the pendant moiety is a carbohydrate, the enzyme can be, for example, a glycosyltransferase.

The labeling agent further can comprise a chemical handle. The chemical handle on the labeling agent can be used to further react the modified protein with a detection agent via a reactive group on the detection agent. The chemical handle preferably does not react substantially with a protein or other components of a biological mixture.

The detection agent can be detectable through various detection means, such as, but not limited to, radioactively, chemiluminescence, fluorescence, mass spectrometry, spin labeling, affinity labeling, or the like. The detection agent can be, for example, a radiolabeled compound or a fluorescent compound. The detection agent also can be detectable indirectly, for example, by recruitment of one or more additional factors.

For example, FIG. 1A shows a general scheme of a detection of post-translationally modified proteins comprising a pendant moiety.

As used herein, "pendant moiety" refers to substituent of the protein. For example, certain post-translational modifications extend a range of possible functions a protein can have by introducing chemical groups or "pendant moieties" into the makeup of a protein.

As used herein, "labeling agent" is an agent that can react with a pendant moiety of a protein. A labeling agent can further comprise a chemical handle for further elaboration or detection.

As used herein, "chemical handle" is a functional group. In an embodiment, the chemical handle can be one of a number of groups as set forth below that can react in a selective manner with a detection agent via a reactive group in the presence of various biomolecules. Alternatively, the chemical handle can itself comprise a detection agent. Such detection agent can be a radioactive atom, as described below.

As used herein and described below, "reactive group" is a functional group that undergoes a chemical reaction with the chemical handle. A reactive group can be contained on a detection agent to react with the chemical handle.

As used herein, "detection agent" is an agent that has a property that can be observed spectroscopically or visually. Methods for production of detectably labeled proteins using detection agents are well known in the art. Detectable labels include, but are not limited to, radioisotopes, fluorophores, paramagnetic labels, antibodies, enzymes (e.g., horseradish peroxidase), or other moieties or compounds which either emit a detectable signal (e.g., radioactivity, fluorescence, color) or emit a detectable signal after exposure of the detection agent to its substrate.

Protein/Pendant Moiety Substrates

Post-translational modification is alteration of a primary structure of the protein after the protein has been translated. There are a wide range of modifications that can take place, such as cleavage, N-terminal extensions, protein degradation, acylation of the N-terminus, amidation of the C-terminal, glycosylation, γ-carboxyglutamine acid, Gal, iodination, covalent attachment of prosthetic groups, phosphorylation, methylation, acetylation, adenylation and ADP-ribosylation, covalent cross links within, or between, polypeptide chains, sulfonation, prenylation, Vitamin C dependent modifications, Vitamin K dependent modification, and selenoproteins. These modifications act on individual residues either by cleavage at specific points, deletions, additions or having the side chains converted or modified.

Certain post-translational modifications will append a pendant moiety onto a protein. In one embodiment, the pendant moiety is a glycosyl group, or a carbohydrate. Glycoproteins comprise proteins covalently linked to carbohydrate. The predominant sugars found in glycoproteins are glucose, galactose, mannose, fucose, GalNAc, GlcNAc and NANA. Carbohydrates can be linked to the protein component through either O-glycosidic or N-glycosidic bonds. The N-glycosidic linkage is commonly through the amide group of asparagine. The O-glycosidic linkage is commonly to the hydroxyl of serine, threonine or hydroxylysine. The preferred embodiments contemplate detection of glycosylated proteins.

One embodiment involves detection of O-linked β-N-acetylglucosamine (O-GlcNAc) glycosylated proteins. O-linked β-N-acetylglucosamine (O-GlcNAc) glycosylation is the covalent attachment of β-N-acetylglucosamine pendant moiety to serine or threonine residues of proteins. Unlike most carbohydrate modifications, O-GlcNAc is dynamic and intracellular and, as such, shares common features with protein phosphorylation. Nearly 80 proteins bearing the O-GlcNAc group have been identified to date, including transcription factors, cytoskeletal proteins, protein kinases, and nuclear pore proteins. Recent studies have elucidated diverse roles for the O-GlcNAc modification, ranging from nutrient sensing to the regulation of proteasomal degradation and gene silencing. Moreover, perturbations in O-GlcNAc levels have been associated with disease states such as cancer, Alzheimer's disease, neurodegeneration, cardiovascular disease, and diabetes.(98-106)

Labeling Agents and Enzymes

A labeling agent is an agent that can react with a pendant moiety of a protein while further comprising a chemical handle for further reaction. An enzyme can be used to transfer the labeling agent or a portion of the labeling agent to the pendant moiety on the protein of interest. When the pendant moiety is a carbohydrate, the enzyme will typically be a glycosyltransferase specific for the pendant moiety of interest. The enzyme can be a naturally occurring enzyme, a mutant enzyme, or an evolved enzyme that is specific for the pendant moiety. The enzyme can transfer the labeling agent to the pendant group on the protein. Glycosyltransferases that can be employed in the cells of the preferred embodiments include, but are not limited to, galactosyltransferases, fucosyltransferases, glucosyltransferases, N-acetylgalactosaminyltransferases, N-acetylglucosaminyltransferases, glucuronyltransferases, sialyltransferases, mannosyltransferases, glucuronic acid transferases, galacturonic acid transferases, oligosaccharyltransferases.

A certain embodiment utilizes GalT, β-1,4-galactosyltransferase, or a mutant thereof. GalT is an enzyme that can catalyze the transfer of galactose from uridine diphosphate-galactose (UDP-galactose) to terminal GlcNAc groups. In another embodiment, GalT has been mutated, such as with a single Y289L mutation, to enlarge the binding pocket and to enhance the catalytic activity toward substrates. Other mutations to GalT are contemplated such that the mutation provide enlargement of the binding pocket and enhancement of the catalytic activity toward substrates.

Chemical Handles

The chemical handle can be one of a number of groups that can react in a selective manner with the reactive group of a detection agent in the presence of various biomolecules, and particularly in an aqueous solution. Alternatively, the chemical handle can itself comprise a detection agent. In one embodiment, the chemical handle comprises a radioactive substance. A chemical handle is contained on a labeling agent. Some representative chemistries are described herein.

Carbonyl Group Chemical Handle

The carbonyl group participates in a large number of reactions from addition and decarboxylation reactions to aldol condensations. Moreover, the unique reactivity of the carbonyl group allows it to be selectively modified with hydrazide and aminooxy derivatives in the presence of the other amino acid side chains. See, e.g., Cornish, V. W., Hahn, K. M. & Schultz, P. G. (1996) *J. Am. Chem. Soc.* 118:8150-8151; Geoghegan, K. F. & Stroh, J. G. (1992) *Bioconjug. Chem.* 3:138-146; and, Mahal, L. K., Yarema, K. J. & Bertozzi, C. R. (1997) *Science* 276:1125-1128. This functional group is generally absent from proteins and thus can serve as a chemical handle for subsequent protein modification.

For reaction with the carbonyl group chemical handle, a reactive group can be —NR$^1$—NH$_2$ (hydrazide), —NR$^1$(C=O)NR$^2$NH$_2$ (semicarbazide), —NR$^1$(C=S)NR$^2$NH$_2$ (thiosemicarbazide), —(C=O)NR$^1$NH$_2$ (carbonylhydrazide), —(C=S)NR$^1$NH$_2$ (thiocarbonylhydrazide), —(SO$_2$)NR$^1$NH$_2$ (sulfonylhydrazide), —NR$^1$NR$^2$(C=O)NR$^3$NH$_2$ (carbazide), —NR$^1$NR$^2$(C=S)NR$^3$NH$_2$ (thiocarbazide), —O—NH$_2$ (aminooxy), and/or the like, where each R$^1$, R$^2$, and R$^3$ is independently H, or alkyl having 1-6 carbons, preferably H. In one aspect of the preferred embodiments, the reactive group is a hydrazide, aminooxy, semicarbazide, carbohydrazide, a sulfonylhydrazide, or the like.

The product of the reaction between the chemical handle and the reactive group typically incorporates the atoms originally present in the reactive group. Typical linkages obtained by reacting the aldehyde or ketone chemical handles with certain reactive groups include reaction products such as an oxime, a hydrazone, a reduced hydrazone, a carbohydrazone, a thiocarbohydrazone, a sulfonylhydrazone, a semicarbazone, a thiosemicarbazone, or similar functionality, depending on the nucleophilic moiety of the reactive group and the aldehyde or ketone chemical handle. Linkages with carboxylic acids are also possible and result in carbohydrazides or hydroxamic acids. Linkages with sulfonic acid chemical handles are also possible with the above reactive groups and result in sulfonylhydrazides or N-sulfonylhydroxylamines. The resulting linkage can be subsequently stabilized by chemical reduction. For instance, the carbonyl group reacts readily with hydrazides, aminooxy, and semicarbazides under mild conditions in aqueous solution, and forms hydrazone, oxime, and semicarbazone linkages, respectively, which are stable under physiological conditions. See, e.g., Jencks, W. P. (1959) *J. Am. Chem. Soc.* 81, 475-481; Shao, J. & Tam, J. P. (1995) *J. Am. Chem. Soc.* 117:3893-3899.

Azide and Alkyne Chemical Handle

A native or mutated glycosyltransferase can be employed to transfer a monosaccharide labeling agent containing an azide chemical handle or an alkyne chemical handle onto the O-GlcNAc pendant moiety. Once incorporated, the azide or alkyne chemical handle on the saccharide labeling agent can then be modified by, e.g., a Huisgen [3+2]cycloaddition reaction in aqueous conditions in the presence of a catalytic amount of copper (See, e.g., Tornoe, et al., (2002) *Org. Chem.* 67:3057-3064; and, Rostovtsev, et al., (2002) *Angew. Chem. Int. Ed.* 41:2596-2599; Padwa, A. in *Comprehensive Organic Synthesis, Vol.* 4, (1991) Ed. Trost, B. M., Pergamon, Oxford, p. 1069-1109; and, Huisgen, R. in 1,3-*Dipolar Cycloaddition Chemistry*, (1984) Ed. Padwa, A., Wiley, New York, p. 1-176). In a [3+2]cycloaddition addition reaction, where either an azide or an alkyne is a chemical handle, the other functionality would act as a reactive group. The [3+2]cycloaddition addition reaction can be used to introduce affinity probes (biotin), dyes, polymers (e.g., poly(ethylene glycol) or polydextran) or other monosaccharides (e.g., glucose, galactose, fucose, O-GlcNAc, mannose-derived saccharides bearing the appropriate chemical handle). The Huisgen 1,3-dipolar cycloaddition of azides and acetylenes can give 1,2,3-triazoles, also called "click chemistry." (see Lewis W G, Green L G, Grynszpan F, Radic Z, Carlier P R, Taylor P, Finn M G, Sharpless K B. *Angewandte Chemie-Int'l Ed.* 41 (6): 1053.).

Because the method involves a cycloaddition rather than a nucleophilic substitution reaction, proteins modified with the instant labeling agent can be modified with extremely high selectivity (as opposed to reactions with amines, carboxylates or sulfhydryl groups which are found more commonly on the surface of proteins). The reaction can be carried out at room temperature in aqueous conditions with excellent regioselectivity (1,4>1,5) by the addition of catalytic amounts of Cu(I) salts to the reaction mixture. See, e.g., Tomoe, et al., (2002) *Org. Chem.* 67:3057-3064; and, Rostovtsev, et al., (2002) *Angew. Chem. Int. Ed.* 41:2596-2599. The resulting five-membered ring that is attached to the labeling agent and the detection agent that results from the Huisgen [3+2]cycloaddition is not generally reversible in reducing environments and is stable against hydrolysis for extended periods in aqueous environments.

The chemical handle also can be an azido group capable of reacting in a Staudinger reaction (see, for example, Saxon, E.; Luchansky, S. J.; Hang, H. C.; Yu, C.; Lee, S. C.; Bertozzi, C. R.; *J. Am. Chem. Soc.;* 2002; 124(50); 14893-14902.). The Staudinger reaction, which involves reaction between trivalent phosphorous compounds and organic azides (Staudinger et al. Helv. Chim. Acta 1919, 2, 635), has been used for a multitude of applications. (Gololobov et al. Tetrahedron 1980, 37, 437); (Gololobov et al. Tetrahedron 1992, 48, 1353). There are almost no restrictions on the nature of the two reactants. The phosphine can have a neighboring acyl group such as an ester, thioester or N-acyl imidazole (i.e. a phosphinoester, phosphinothioester, phosphinoimidazole) to trap the aza-ylide intermediate and form a stable amide bond upon hydrolysis. The phosphine can also be typically a di- or triarylphosphine to stabilize the phosphine.

Olefin Chemical Handle

The labeling agent can comprise an olefin chemical handle and can be reacted with a reactive group on a detection agent using a cross metathesis reaction in the presence of a catalyst. In a cross metathesis reaction, where the chemical handle is an olefin, a reactive group is an olefin, an alkyne, or an appropriate substrate for a metathesis reaction with an olefin. Commonly, where the chemical handle is an olefin, a reactive group is also an olefin. Catalysts for a cross metathesis reaction are well-known and include water-soluble catalysts. such as those described in Lynn D M, Mohr B, Grubbs R H, Henling L M, and Day M W (2000) *J. Am. Chem. Soc.;* 2000; 122: 6601-6609 and those review in Chen L Y, Yang H J, Sun W H (2003) *Progress In Chemistry* 15: 401-408.

The chemical handle is substantially not reactive with components of a biological mixture, such as a typical cellular extract, including for example, nucleic acids and proteins. A preferred chemical handle is a carbonyl chemical handle, which can react with a reactive group, such as an aminoxy, hydrazide or thiosemicarbazide group on the detection agent.

Detection Agents

A variety of detection agents can be used. The detection agent can itself be detectable, or can be used to recruit another labeling molecule or enzyme, a secondary detection agent. The detection agent has a reactive group that can bind to or react with the chemical handle.

A detection agent is an agent that has a property that can be observed spectroscopically or visually. Methods for production of detectably labeled proteins using detection agents are well known in the art. The detection agent can be detectable through various detection means, such as radioactively, chemiluminescence, fluorescence, mass spectrometry, spin labeling, affinity labeling, or the like. The detection agent also can be detectable indirectly, for example, by recruitment of one or more additional factors.

A radioactive substance refers to a radioactive atom, a substance having radioactive atoms incorporated therein, or a substance radiolabeled with an additional or substituted radioactive atom not normally found in the native substance. Examples of radioactive atoms include, but are not limited to, $^{32}P$, $^{33}P$, $^{35}S$, $^{125}I$, $^{3}H$, $^{13}C$, $^{14}C$, $^{51}Cr$, and $^{18}O$. In one embodiment, the chemical handle further comprises such a radioactive substance.

Most chemiluminescence methods involve chemical components to actually generate light. Chemiluminescence is the generation of electromagnetic radiation as light by the release of energy from a chemical reaction. While the light can, in principle, be emitted in the ultraviolet, visible or infrared region, those emitting visible light are the most common. Chemiluminescent reactions can be grouped into three types:

1) Chemical reactions using synthetic compounds and usually involving a highly oxidized species, such as peroxide, are commonly termed chemiluminescent reactions.
2) Light-emitting reactions arising from a living organism, such as the firefly or jellyfish, are commonly termed bioluminescent reactions.
3) Light-emitting reactions which take place by the use of electrical current are designated electrochemiluminescent reactions.

Examples of chemiluminescent detection agents include, but are not limited to, luminol chemiluminescence, peroxyoxalate chemiluminescence, and diphenylanthracene chemiluminescence.

Fluorescence is the phenomenon in which absorption of light of a given wavelength by a fluorescent molecule is followed by the emission of light at longer wavelengths. Examples of fluorescent detection agents include, but are not limited to, rhodamine, fluorescein, Texas red, cyanine dyes, nanogold particles coated with gold, and analogues thereof and alike.

Mass spectrometry is an analytical technique that is used to identify unknown compounds, quantify known materials, and elucidate the structural and physical properties of ions. Mass Spectrometry can be used in conjunction with chromatography techniques, such as LC-MS and GC-MS. Examples of mass spectrometry tools for use as detection agents include, but are not limited to, electron ionisation (EI), chemical ionisation (CI), fast atom bombardment (FAB)/liquid secondary ionisation (LSIMS), matrix assisted laser desorption ionisation (MALDI), and electrospray ionisation (ESI). See, for example, Gary Siuzdak, *Mass Spectrometry for Biotechnology*, Academic Press, San Diego, 1996.

Electron paramagnetic resonance (EPR), also known as electron spin resonance (ESR) and electron magnetic resonance (EMR), is the name given to the process of resonant absorption of microwave radiation by paramagnetic ions or molecules, with at least one unpaired electron spin, and in the presence of a static magnetic field. Species that contain unpaired electrons include free radicals, odd electron molecules, transition-metal complexes, lanthanide ions, and triplet-state molecules.

Affinity labeling is a method for tagging molecules so that they can be more easily detected and studied. Affinity labeling can be based on substituting an analogue of a native substrate.

In one embodiment, the detection agent is a biotin or a biotin derivative. Biotin and biotin derivatives are well known to one of skill in the art, and are described in the *Handbook of Fluorescent Probes and Research Products, Ninth Edition*, Molecular Probes, Eugene, Oreg., 2002. Additional detection schemes also are provided in the Handbook. Secondary detection agents also are disclosed, including fluorescent reagents (e.g., fluorescently labeled streptavidin) and enzymatic reagents that can convert substrates colorimetrically or fluorometrically (e.g., streptavidin alkaline phosphatase and streptavidin-horseradish peroxidase conjugates). A number of detection schemes are known to one of skill in the art and include, for example: fluorescent and luminescent probes (e.g., fluoroscein hydrazide, metal nanoparticles or quantum dots) (see, e.g., Geoghegan, K. F. & Stroh, J. G. (1992) *Bioconjug. Chem.* 3:138-146); metal-binding probe (e.g., polyhistidine tag or metal chelate); protein-binding probes (e.g., FLAG-tag); probe (e.g., dinitrophenol) for antibody-based binding; radioactive probe (circumvent challenging synthesis and handling of radiolabeled monosaccharides); photocaged probe; spin-label or spectroscopic probe; heavy-atom containing probe (i.e., Br, I) for x-ray crystallography studies; polymer (e.g. PEG- or poly(propylene) glycol) containing probe; probes that permit protein cross-linking (e.g., to covalently modify binding partners to protein being modified, such as containing diazirene, benzophenone, or azidophenyl groups); and binding to particles or surfaces that contain complementary functionality.

GlcNAc Detection

Figure 1B:
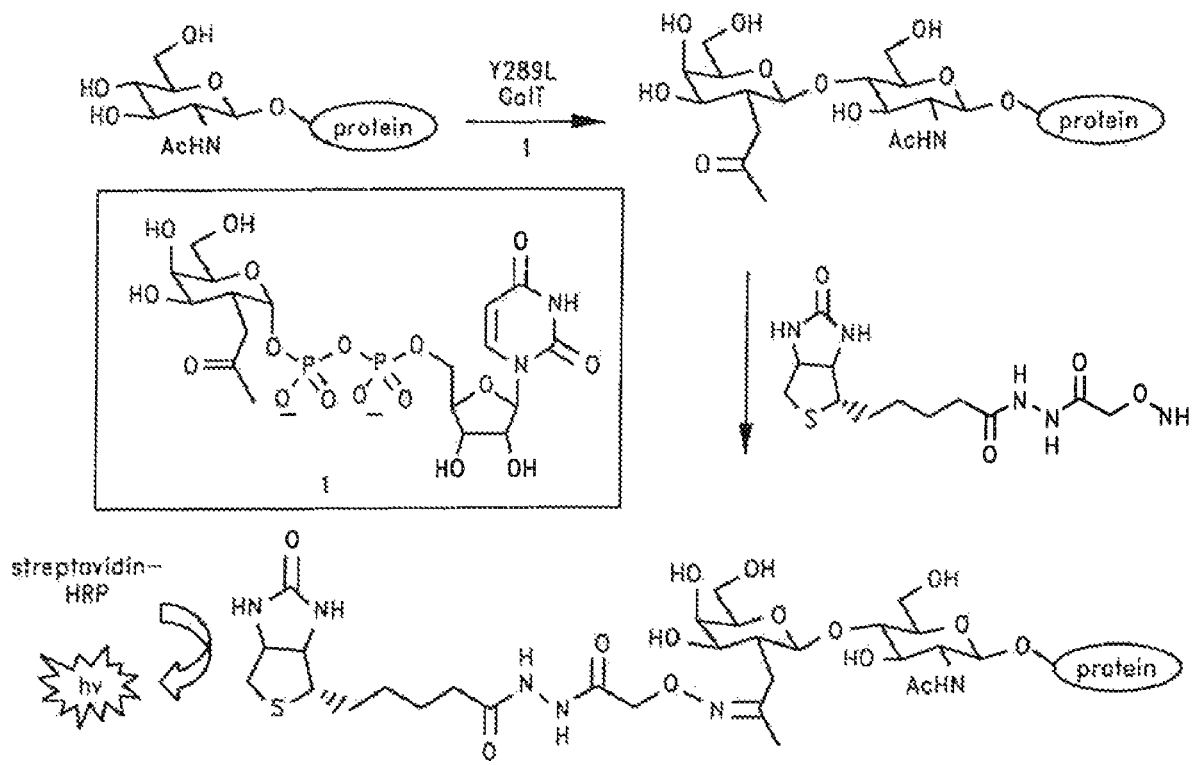
FIG. 1B shows a general strategy for detection of O-GlcNAc glycosylated proteins.

In one embodiment, the preferred embodiments provide methods for the rapid and sensitive detection of O-GlcNAc glycosylated proteins. One approach capitalizes on the substrate tolerance of GalT, which allows for chemoselective installation of a non-natural ketone chemical handle to O-GlcNAc glycosylated proteins (FIG. 1B). The ketone moiety has been well-characterized in cellular systems as a neutral, yet versatile chemical handle. Here, the ketone chemical handle serves as a unique marker to "tag" O-GlcNAc glycosylated proteins with biotin. Once biotinylated, the modified proteins can be readily detected by chemiluminescence, such as using streptavidin conjugated to horseradish peroxidase (HRP).

FIG. 1B shows a general strategy for detection of O-GlcNAc glycosylated proteins. In a particular embodiment, as shown in FIG. 1B, the methods of the preferred embodiments are used to detect O-GlcNAc pendant moiety on a protein or a mixture of proteins. According to the methods, a protein having the pendant moiety is contacted with a labeling agent comprising a chemical handle. The labeling agent can be a substrate of a particular enzyme that reacts with the pendant moiety on the protein to be labeled, for example, the labeling agent can be an analog of uridyl phosphate sugar. A glycosyltransferase can transfer the labeling agent to the GlcNAc pendant moiety on the protein. In one embodiment, the chemical handle is a ketone moiety, which is substantially unreactive with biological constituents. When the chemical handle is a ketone, the labeled protein can then be reacted with a detection agent comprising a reactive group, for example, a detection agent having an aminoxy, hydrazide or thiosemicarbazide reactive group. The detection agent can be a biotin moiety, which allows recruitment of a variety of avidin- or streptavidin-linked secondary detection agents, including fluorescent dyes and enzymes that can convert substrates to give a detectable signal.

In one embodiment, the detection agent is a biotin moiety. When the detection agent is a biotin moiety, it can be used to noncovalently recruit a number of secondary detection agents, including, for example, enzymes capable of making reacting with fluorogenic, chemiluminescent, colorimetric products. The biotin is also useful for affinity chromatography using streptavidin/avidin conjugated to sepharose/agarose. Affinity enrichment allows for the enrichment of glycopeptides present in low cellular abundance. O-GlcNAc peptides can be challenging to detect by mass spectrometry in the absence of enrichment strategies. According to the preferred embodiments, biological mixtures, such as cell lysates, can be labeled with the labeling agent 1. Such biological mixtures can then be: treated with PNGase F to remove N-linked sugars, digested with protease such as trypsin, captured glycopeptides using monomeric avidin conjugated to agarose, eluted the glycopeptides and identified the peptides by LC-MS. Accordingly, a protein having an O-GlcNAc pendant moiety in a nuclear lysate, can be labeled using the methods of the preferred embodiments with a ketone chemical handle-containing labeling agent and reacted with a biotin derivative. The labeled protein can then be detected by blotting with streptavidin-HRP. Such procedures can allow for high-throughput identification of the O-GlcNAc proteome. Another advantage of the streptavidin-agarose is that intact glycoproteins can be isolated. This procedure can be useful for rapid and fairly high-throughput detection by Western blotting (e.g., label proteins, isolate GlcNAc glycosylated proteins, and then probe the Western blot with antibodies against proteins of interest. This procedure can circumvent developing ways to immunoprecipitate or purify each protein of interest.). This procedure can also be used in conjunction with chromatin immunoprecipitation (CHIP assays) protocols to identify the genes regulated by post-translationally modified transcription factors.

Engineered Enzyme and Corresponding Substrate

One approach capitalizes on the substrate tolerance of GalT, which allows for chemoselective installation of a non-natural functionality, such as a ketone chemical handle, to O-GlcNAc pendant moiety on modified proteins (FIG. 1B).

GalT has been shown to tolerate unnatural substrates containing minor substitutions at the C-2 position, including 2-deoxy, 2-amino, and 2-N-acetyl substituents.(6) Moreover, 2-deoxy-Gal was transferred at rates comparable to Gal, whereas 3-, 4-, and 6-deoxy-Gal were transferred at reduced rates. Analysis of the crystal structures of GalT complexed with UDP-GalNAc revealed that the C-2 N-acetyl moiety is accommodated in a shallow pocket within the active site.(7) Importantly, the single Y289L mutation enlarges the binding pocket of GalT and enhances the catalytic activity toward GalNAc substrates without compromising specificity.(7) Other mutations that provide the same effect are contemplated.

Glycosyltransferases that can be employed in the cells of the preferred embodiments include, but are not limited to, galactosyltransferases, fucosyltransferases, glucosyltransferases, N-acetylgalactosaminyltransferases, N-acetylglucosaminyltransferases, glucuronyltransferases, sialyltransferases, mannosyltransferases, glucuronic acid transferases, galacturonic acid transferases, oligosaccharyltransferases. Enzyme design to enlarge binding pockets to accommodate altered substrates for these glycosyltransferases is contemplated. Generally, the binding pocket for the glycosyltransferase is identified, for instance, through crystal structure analysis. Then, the individual residues of the binding pocket of the glycosyltransferase can be mutated. Through homology modeling, the binding pocket of the mutated glycosyltransferase can be envisioned. Further modeling studies can explore binding of substrates in the binding pocket of the mutated glycosyltransferase. A preferred mutated enzyme would enlarge the binding pocket of the enzyme and/or enhance the catalytic activity toward substrates without compromising specificity.

As a labeling agent, a uridyl diphosphate analogue 1 was designed based on previous biochemical and structural studies of GalT (FIG. 1B). The ketone chemical handle was appended at the C-2 position of the galactose ring because GalT has been shown to tolerate unnatural substrates containing minor substitutions at the C-2 position.

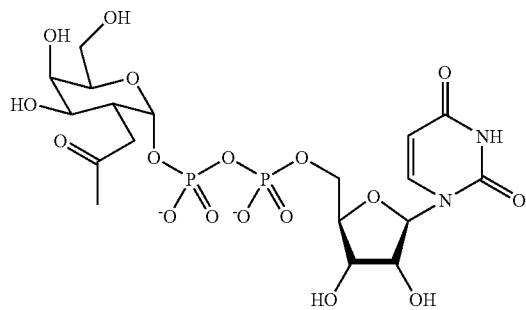

This analogue can be used in conjunction with GalT or mutated GalT. In one embodiment, uridyl diphosphate analogue 1 is used with mutated GalT. In another embodiment, uridyl diphosphate analogue 1 is used with mutated GalT with Y289L mutation.

Accordingly, a class of uridyl diphosphate analogues is designed to be accommodated in a shallow pocket within the active site of GalT or a GalT analogue.

Genus A wherein R is a substituent selected from the group consisting of straight chain or branched $C_1$-$C_{12}$ carbon chain bearing a carbonyl group, azide group, straight chain or branched $C_1$-$C_{12}$ carbon chain bearing an azide group, straight chain or branched $C_1$-$C_{12}$ carbon chain bearing an alkyne, and straight chain or branched $C_1$-$C_{12}$ carbon chain bearing an alkene.

Another embodiment of a class of uridyl diphosphate analogues is designed to be accommodated in a shallow pocket within the active site of GalT or mutated GalT.

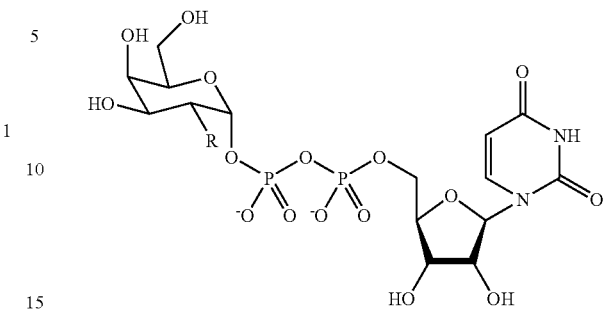

Genus A' wherein R is selected from the group consisting of straight chain or branched $C_2$-$C_4$ carbon chain bearing a carbonyl group, azide group, straight chain or branched $C_2$-$C_4$ carbon chain bearing an azide group, straight chain or branched $C_2$-$C_4$ carbon chain bearing an alkyne, and straight chain or branched $C_2$-$C_4$ carbon chain bearing an alkene.

A preferred compound within Genus A is Compound 1.

Figure 2:
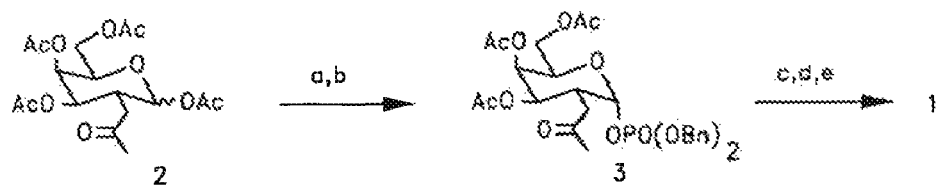
FIG. 2 shows a scheme for preparing labeling agent 1.

Labeling agent 1 was synthesized from the previously reported ketone 2 (8) as shown in FIG. 2. FIG. 2 shows a scheme with the following conditions: (a) Me$_2$NH, THF (53%); (b) (BnO)$_2$PNiPr$_2$, then mCPBA (54%); (c) Pd/C, H$_2$, tri-n-octylamine; (d) UMP-morpholidate, 1H-tetrazole, pyr; (e) TEA, H$_2$O/MeOH (45%, 3 steps).

Synthesis of Genus A follows closely with FIG. 2, except with the use a corresponding starting material instead of ketone 2.

In general, a novel chemoenzymatic strategy that detects O-GlcNAc modifications with an efficiency and sensitivity that is disclosed. A variety of applications, including direct fluorescence detection, affinity enrichment, and isotopic labeling for comparative proteomics, is also contemplated. Moreover, a broad application to the discovery, detection, and quantification of other posttranslational modifications such as farnesylation and methylation is also made possible by the instant embodiments. The approach to novel glycosylated proteins and to the dynamic regulation of the modification in cells is also made possible by the instant embodiments.

The examples disclosed below illustrated preferred embodiments and are not intended to limit the scope. It would be obvious to those skilled in the art that modifications or variations may be made to the preferred embodiments described herein without departing from the teachings of the present invention.

EXAMPLE 1

A Chemoenzymatic approach Toward the Rapid and Sensitive Detection of O-GlcNAc Posttranslational Modifications (95)

Design of a GlcNAc Labeling Agent

A labeling agent of uridyl diphosphate analogue 1 was designed based on previous biochemical and structural studies of GalT (FIG. 1B). The ketone chemical handle was appended at the C-2 position of the galactose ring because GalT has been shown to tolerate unnatural substrates containing minor substitutions at the C-2 position, including 2-deoxy, 2-amino, and 2-N-acetyl substituents.(6) Moreover, 2-deoxy-Gal was transferred at rates comparable to Gal, whereas 3-, 4-, and 6-deoxy-Gal were transferred at reduced rates. Analysis of the crystal structures of GalT complexed with UDP-GalNAc revealed that the C-2 N-acetyl moiety is accommodated in a shallow pocket within the active site.(7) The single Y289L mutation enlarges the binding pocket and enhances the catalytic activity toward GalNAc substrates without compromising specificity.(7)

Synthesis of GlcNAc Labeling Agent

Labeling agent 1 was synthesized from the previously reported ketone 2 (8) as shown in FIG. 2. FIG. 2 shows a scheme with the following conditions: (a) $Me_2NH$, THF (53%); (b) $(BnO)_2PNiPr_2$, then mCPBA (54%); (c) Pd/C, $H_2$, tri-n-octylamine; (d) UMP-morpholidate, 1H-tetrazole, pyr; (e) TEA, $H_2O$/MeOH (45%, 3 steps).

Selective anomeric deacetylation followed by treatment with $(BnO)_2PNiPr_2$(9) afforded the phosphite, which was directly oxidized with mCPBA(10) to produce dibenzyl phosphate 3. Hydrogenolytic debenzylation yielded the unprotected phosphate as the trioctylammonium salt, which was coupled with UMP-morpholidate in pyridine (11) to provide labeling agent 1 upon deacetylation with TEA.

Labeling a GlcNAc-Containing Peptide

Figure 3:
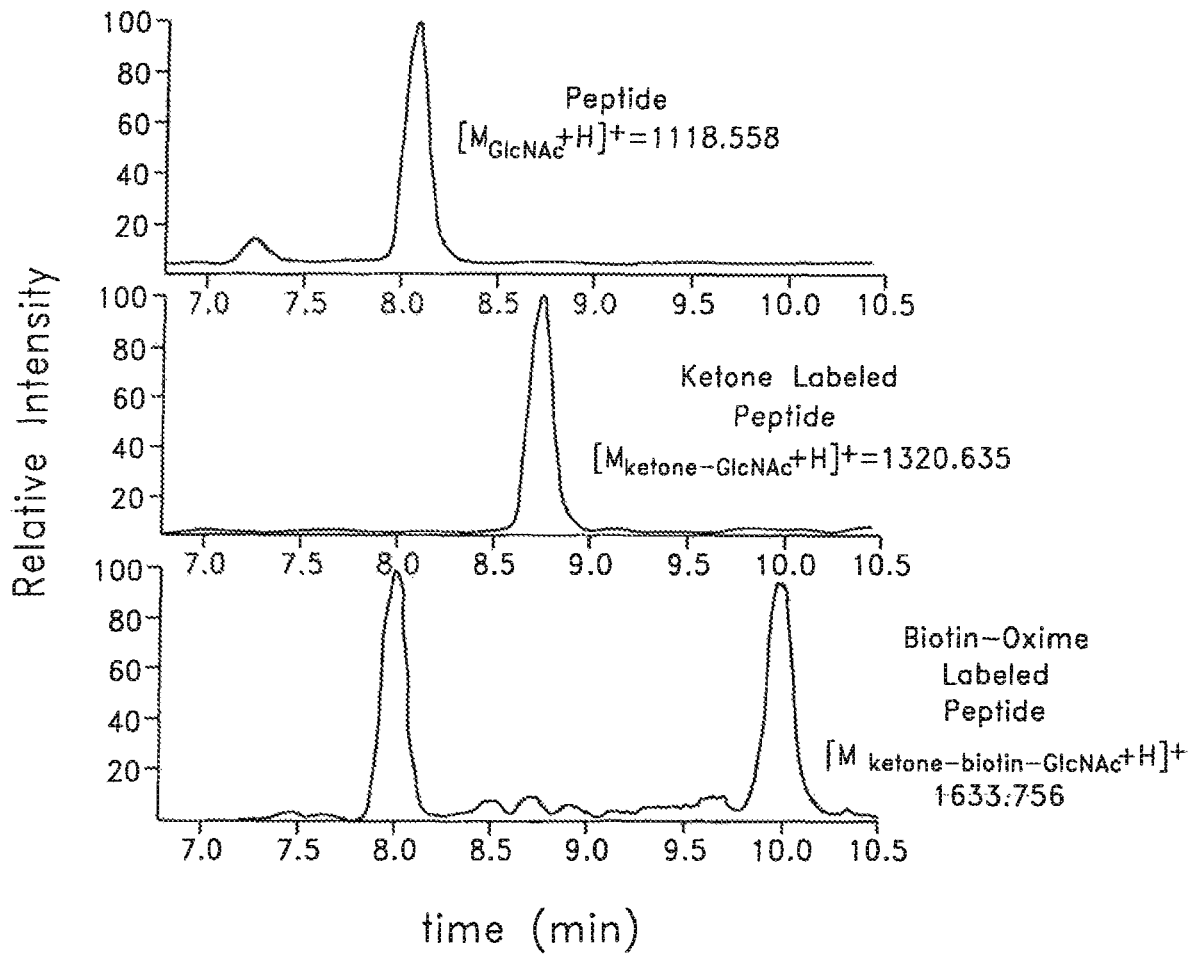
FIG. 3 shows labeling of the peptide TAPTS(O-GlcNAc)TIAPG (SEQ ID NO: 1) via LC-MS traces.

The ability of GalT to label the peptide TAPTS(O-GlcNAc)TIAPG (SEQ ID NO: 1), which encompasses an O-GlcNAc modification site within the protein CREB (SEQ ID NO: 48)(12) was examined with labeling agent 1. Using wild-type GalT, only partial transfer of the keto-sugar was observed by LC-MS (~1.5% after 12 h at 37° C.). As anticipated, however, the Y289L mutant GalT enzyme showed greater activity and afforded complete conversion after 6 h at 4° C. (FIG. 3). Subsequent reaction of the ketone chemical handle-labeled peptide with the aminooxy biotin derivative detection agent, N-(aminooxyacetyl)-N'-(D-biotinoyl)hydrazine, under mild conditions (pH 6.7 buffer, 8 h, 25° C.) gave essentially complete formation of the corresponding O-alkyl oxime.

FIG. 3 shows labeling of the peptide TAPTS(O-GlcNAc) TIAPG (SEQ ID NO: 1). LC-MS traces monitoring the reaction progress at (A) time 0, (B) 6 h after the addition of 1 and Y289L GalT, and (C) 8 h after biotin addition. A and B represent base peak chromatograms and C is the extracted ion chromatogram within 1319.0-1321.0 and 1633.0-1635.5 m/z. The peak at 8 min in C is a biotin impurity.

Labeling CREB Protein

Figure 4:
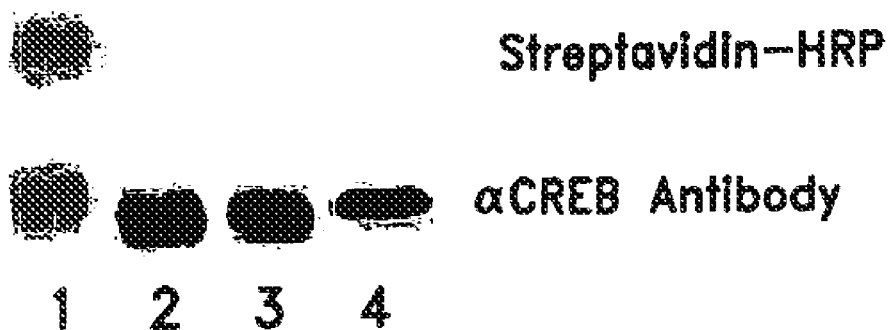
FIG. 4 shows selective labeling of glycosylated CREB, where CREB from Sf9 cells were tested in lanes 1-3 and E. coli was tested in lane 4.

Having demonstrated the labeling of a peptide, the preferred embodiments were applied to the O-GlcNAc glycosylated protein CREB. Recombinant CREB from Sf9 cells (12) was incubated with labeling agent 1 and Y289L GalT for 12 h at 4° C. Following reaction with aminooxy biotin detection agent, the mixture was resolved by SDS-PAGE, transferred to nitrocellulose, and probed with streptavidin-HRP. Strong labeling of CREB was observed by chemiluminescence within seconds of exposure to film (FIG. 4). FIG. 4 shows selective labeling of glycosylated CREB. CREB from Sf9 cells (lanes 1-3) or E. coli (lane 4) was tested. In contrast, no signal was observed over the same time period for unglycosylated CREB (from E. coli) or when reactions were performed in the absence of either 1 or enzyme, demonstrating the selectivity of the transfer.

Labeling α-Crystallin

Figure 5:
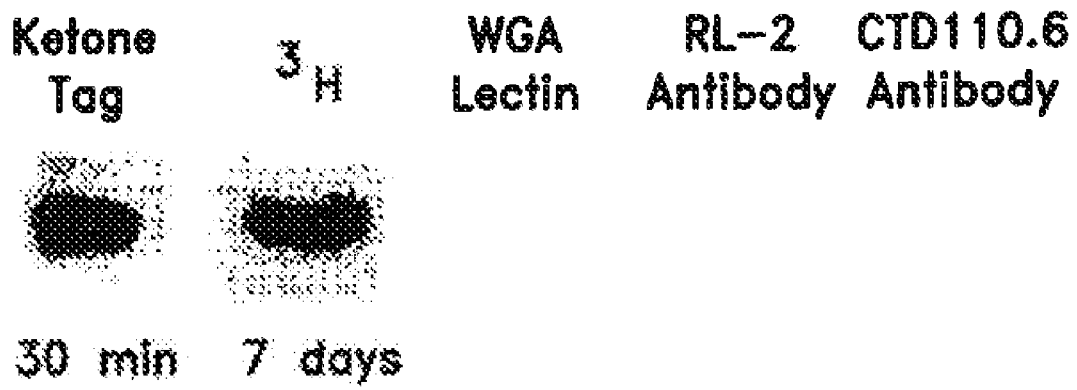
FIG. 5 shows labeling of α-crystallin, and comparison with several existing detection methods.
Figure 6A:
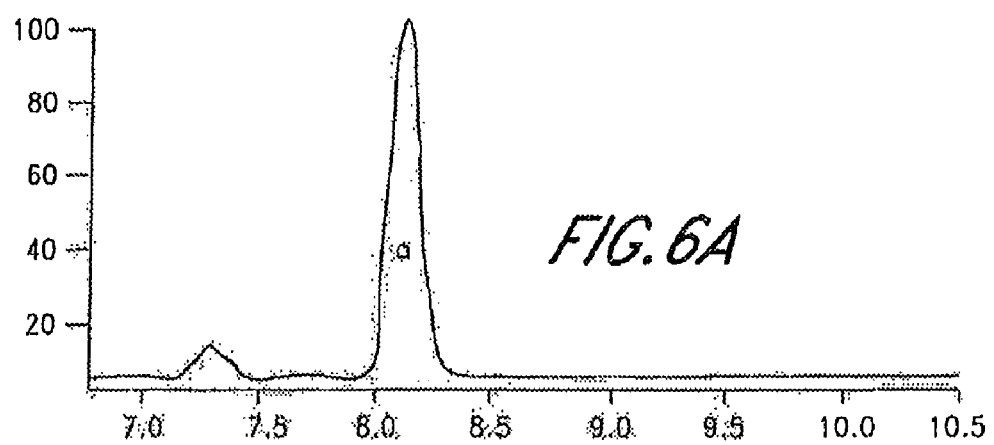
FIG. 6 shows reverse phase LC-MS analysis of O-GlcNAc peptide labeling reactions at (A) time 0, (B) 6 h after the addition of 1 and Y289L GalT, (C) 8 h after aminooxy biotin addition. Trace (D) shows aminooxy biotin in the absence of 1, Y289L GalT and O-GlcNAc peptide.
Figure 6B:
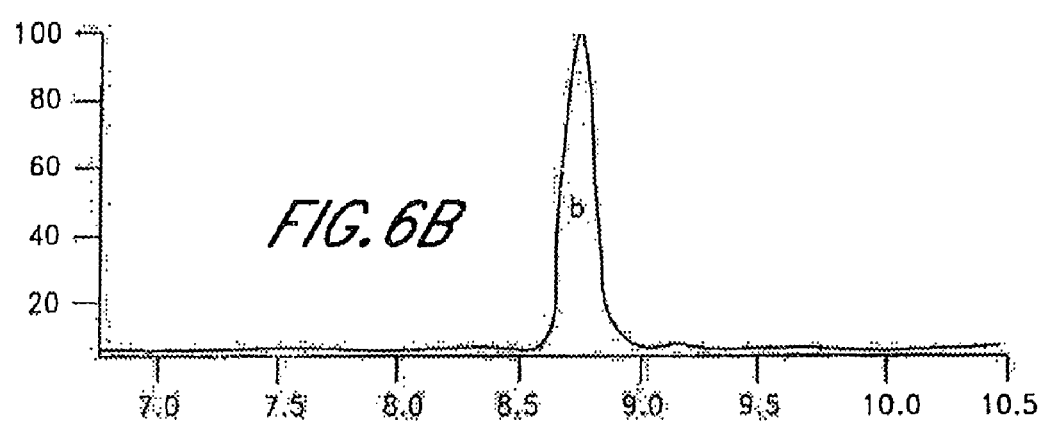
Figure 6C:
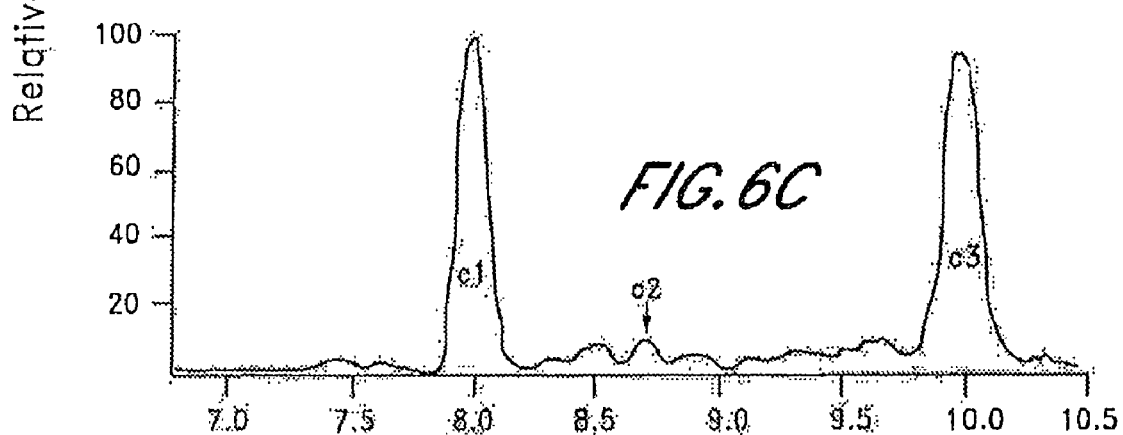
Figure 6D:
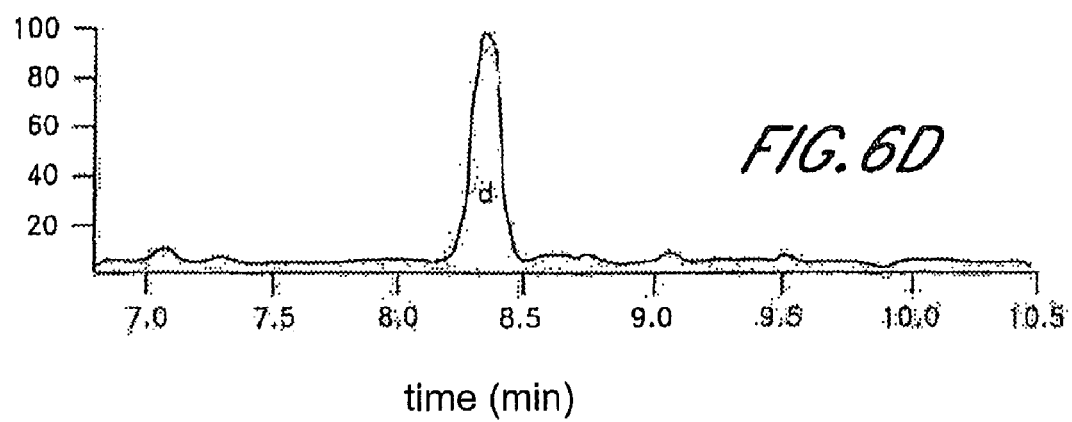
Figure 7A:
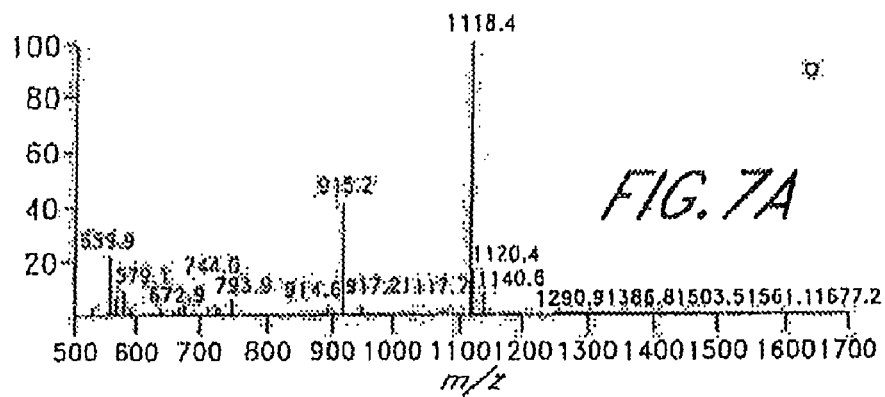
FIGS. 7(A)-(F) show electrospray ionization mass spectra of the peaks in FIG. 6: (A) spectrum of the peptide starting material (peak a), [M.sub.GICNAC+H]$^+$=1118.4, (B) spectrum of the ketone product (peak b), [M.sub.ketone-GlcNAc+H]$^+$=1320.5, (C) spectrum of the biotin impurity (peak c 1), (D) spectrum of peak c2, (E) spectrum of the oxime product (peak c3), and (F) spectrum of the biotin impurity (peak d), obtained by incubating biotin in the absence of 1, Y289L GalT and O-GlcNAc peptide.
Figure 7B:
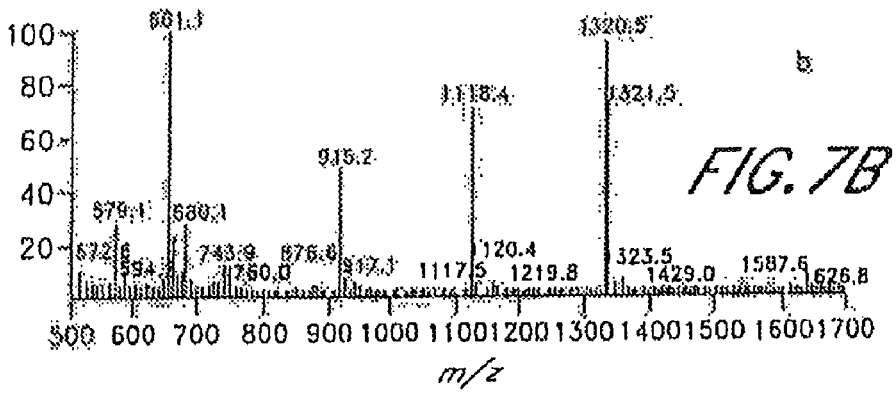
Figure 7C:
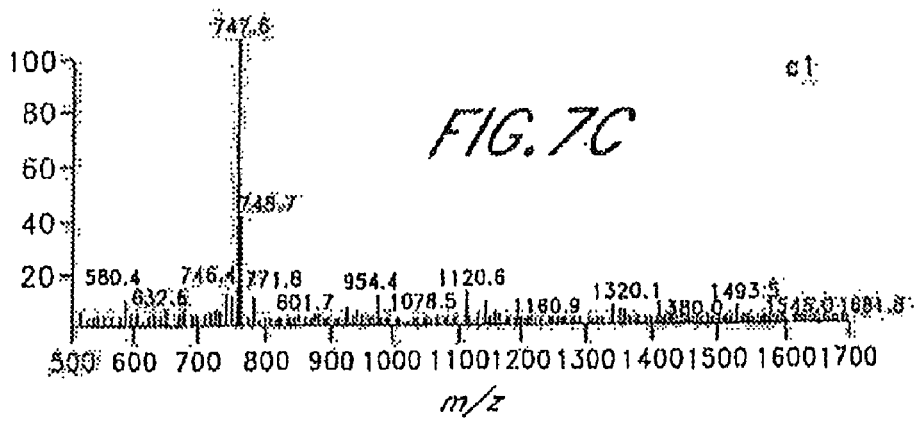
Figure 7D:
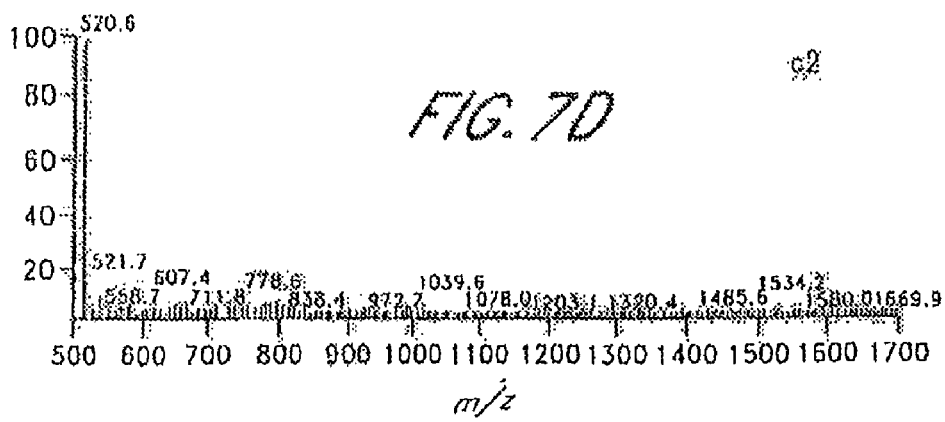
Figure 7E:
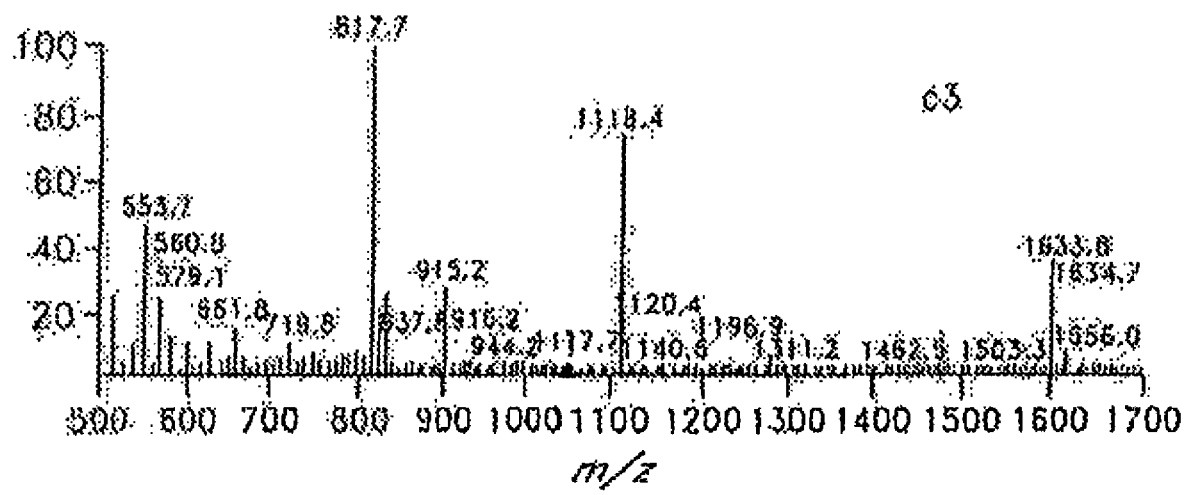
Figure 7F:
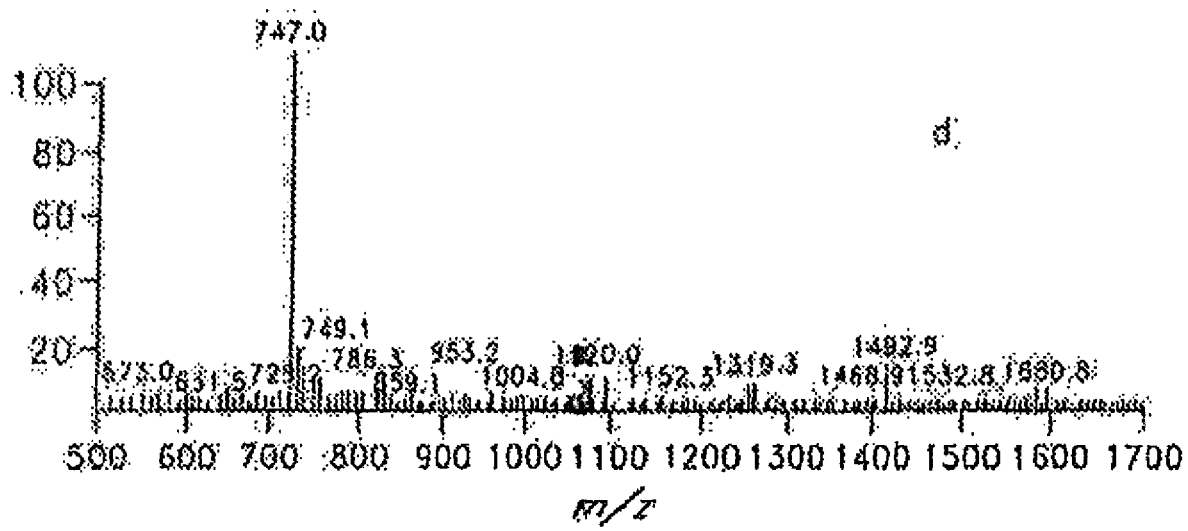

The sensitivity of the preferred embodiments using another target, α-crystallin, was explored. Detection of the O-GlcNAc pendant moiety on α-crystallin has been reported to be particularly difficult due to its low stoichiometry of glycosylation (~10%) and the presence of only one major modification site.(13) Indeed, the existing methods such as wheat-germ agglutinin (WGA) lectin (3) and the O-GlcNAc-specific antibodies RL-2(4) and CTD110.6(5) failed to detect any O-GlcNAc pendant moiety on α-crystallin, even when 10 μg of α-crystallin was used (FIG. 5). FIG. 5 shows labeling of α-crystallin, and comparison with several existing detection methods. For the ketone and tritium labeling studies, 0.75 μg of protein was used; for the lectin and antibodies, 5 μg of protein was used. In contrast, the present embodiments enabled detection of the O-GlcNAc pendant moiety within minutes using 0.75 μg of α-crystallin. For comparison, tritium labeling with wild-type GalT required 8 days of exposure to film for a weaker signal. Thus, the present embodiments represent at least a 380-fold enhancement over traditional methods.

General Methods:

Chemicals and reagents were used without further purification unless otherwise noted. If necessary, reactions were performed under argon atmosphere using anhydrous solvents. Thin layer chromatography was performed using E. Merck silica gel 60 F254 precoated plates and visualized using cerium ammonium molybdate stain. Flash column chromatography was carried out with Silica Gel 60 (230-400 mesh). NMR spectra were obtained on a Varian Mercury 300 instrument. High resolution mass spectra were obtained with a Jeol JMS-600H spectrometer. The peptide TAPTS(O-GlcNAc)TIAPG (SEQ ID NO: 1) was synthesized at the Beckman Institute Biopolymer Synthesis Center using standard Fmoc chemistry. The Fmoc-protected, peracetylated O-GlcNAc serine amino acid was synthesized as reported by Seitz et al.(15) Baculovirus preparation and protein expression of CREB in Spodoptera frugiperda (Sf9) cells were performed at the Beckman Institute Protein Expression Facility at the California Institute of Technology.(16) HeLa cell nuclear extracts were prepared according to published procedures.(17) Y289L and wild-type GalT were expressed and purified as described previously.(18) All protein concentrations were measured using the Bradford assay (Bio-Rad Laboratories, Hercules, Calif.).

General Reagents:

Unless otherwise noted, reagents were purchased from the commercial suppliers Fisher (Fairlawn, N.J.) and Sigma-Aldrich (St. Louis, Mo.) and were used without further purification. Protease inhibitors were purchased from Sigma-Aldrich or Alexis Biochemicals (San Diego, Calif.). Bovine GalT, ovalbumin, and α-crystallin were obtained from Sigma-Aldrich. Uridine diphospho-D-[6-$^3$H]galactose, Hyperfilm ECL and Amplify reagent were purchased from Amersham Biosciences (Piscataway, N.J.). WGA lectin was purchased from E-Y Laboratories (San Mateo, Calif.). RL-2 antibody was purchased from Affinity Bioreagents (Golden, Colo.). Alkaline phosphatase was purchased from New England Biolabs (Beverly, Mass.), and bovine serum albumin (BSA) was obtained from Fisher. SuperSignal West Pico chemiluminescence reagents and secondary antibodies were from Pierce (Rockford, Ill.), and the CTD 110.6 antibody was from Covance Research Products (Berkeley, Calif.). Nitrocellulose was from Schleicher and Schuell (Keene, N.H.), and PVDF was from Millipore (Bedford, Mass.).

2-Acetonyl-2-deoxy-3,4,5-tri-O-acetyl-β-D-galactopyranose (19)

Ketone 2 (289 mg, 0.744 mmol) of FIG. 2 was dissolved in acetonitrile (1.5 mL), and $Me_2NH$ in THF (2.0 M solution, 2.80 mL, 5.60 mmol) was added. The reaction mixture was stirred for 24 h at r.t. The solvents and reagents were evaporated in vacuo. Flash chromatography on silica gel (1:1 hexanes:EtOAc) gave the monodeacetylated product (136 mg, 0.393 mmol, 53%) as a colorless oil.

$^1$H NMR (300 MHz, CDCl$_3$): δ 5.49-5.46 (m, 1H, 1-H), 5.34-5.33 (m, 1H, 4-H), 5.10 (dd, J=12.0, 3.0 Hz, 1H, 3-H), 4.39 (t, J=6.6 Hz, 1H, 5-H), 4.18-4.04 (m, 2H, 6-H$_2$), 2.84-2.72 (m, 1H, 2-H), 2.62-2.54 (m, 2H, 1'-H2), 2.17, 2.14, 2.06, 2.01 (4×s, 12H, 3×Ac, 3'-H$_3$).

$^{13}$C NMR (75 MHz, CDCl$_3$): δ 207.1, 170.4, 170.3, 170.2, 92.8, 68.7, 66.7, 66.1, 62.3, 4Q.9, 34.71 30.4, 20.7, 20.7, 20.7.

HRMS (FAB) calcd. for C$_{15}$H$_{23}$O$_9$ [M+H]$^+$ 347.1342, found 347.1342.

Dibenzyl (2-acetonyl-2-deoxy-3,45-tri-O-acetyl-a-D-galactopyranosyl) phophate (3)(20)

The deprotected ketone (90 mg, 0.26 mmol) and 1H-tetrazole (91 mg, 1.3 mmol) were dissolved in dichloromethane (3 mL). The reaction mixture was cooled to −30° C. and dibenzyl N,N'-diisopropylphosphamidite (170 μL, 0.52 mmol) was added. The reaction mixture was warmed to r.t. over 30 min and stirred at r.t. After 1 h, the reaction mixture was again cooled to −30° C., and mCPBA (229 mg, 1.30 mmol) was added. The mixture was then stirred at 0° C. for 1 h and at r.t. for 1 h. The reaction was subsequently diluted in dichloromethane, washed twice with 10% Na$_2$SO$_3$, once with NaHCO$_3$, and once with H$_2$O. The organic phase was dried over MgSO$_4$, filtered and concentrated. Flash chromatography on silica gel (1:1 hexanes:EtOAc) gave 3 (83 mg, 0.14 mmol, 54%) as a colorless oil.

$^1$H NMR (300 MHz, CDCl$_3$): δ 7.34-7.32 (m, 10H, arom), 5.86 (dd, J=6.0, 3.3 Hz, 1H, 1-H), 5.29 (m, 1H, 4-H), 5.15-4.98 (m, 4H, bn), 4.92 (dd, J=2.7, 12.0 Hz, 1H, 3-H), 4.25 (t, J=6.5 Hz, 1H, 5-H), 4.07-3.93 (m, 2H, 6-H$_2$), 2.90-2.80 (m, 1H, 2-H), 2.35 (d, J=7.2 Hz, 2H, 1'-H$_2$), 2.09, 1.95, 1.91, 1.87 (4×s, 12H, 3×ac, 3'-H$_2$).

$^{31}$P NMR (121 MHz, CDCl$_3$): δ −1.31.

$^{13}$C NMR (75 MHz, CDCl$_3$): δ 205.7, 170.0, 170.0, 169.8, 128.6, 128.5, 128.5, 127.9, 97.7 (d), 69.6 (d), 69.5, 68.3, 68.0, 65.9, 61.7, 39.7, 34.4 (d), 29.9, 20.6, 20.6, 20.5.

HRMS (FAB): calcd. for C$_{29}$H$_{36}$O$_{12}$P [M+H]$^+$ 607.1945, found 607.1924.

Uridine 5'-diphospho-2-acetonyl-2deoxy-α-D-galactopyranose diammonium salt (1)(21)-Labeling Agent A solution of dibenzyl phosphate 3 (80 mg, 0.13 mmol) and tri-n-octylamine (35 μL) in methanol (10 mL) was hydrogenolyzed in the presence of 10% Pd/C (100 mg) under 1 atm H$_2$ for 20 h. The mixture was filtered, concentrated, dried and directly used in the next step. UMP-morpholidate 4-morpholine-N,N'-dicyclohexylcarboxamidine salt (36 mg, 0.198 mmol) was added and the mixture was evaporated three times from anhydrous pyridine (1.5 mL). The mixture was dissolved in pyridine (1.0 mL), 1H-tetrazole (28 mg, 0.40 mmol) was added, and the solution was stirred for three days at r.t. After evaporation of the solvent, the reaction product was dissolved in a mixture of MeOH/water/TEA (2 mL/0.8 mL/0.4 mL) and stirred for 24 h. The residue was then dissolved in water and dichloromethane, and the organic phase was extracted twice with water. The aqueous phases were combined and lyophilized. The residue was purified on a Bio-Gel P2 (extra fine) column (1.5×80 cm), and eluted with 0.1 M NH$_4$HCO$_3$ at a flow rate of 0.6 mL/min. Lyophilization of the desired fractions (determined by HPLC, Varian Microsorb C18, 100 mM NH$_4$HCO$_3$, 4.1 min) gave labeling agent 1 (38.7 mg, 0.060 mmol, 45%) as a colorless powder.

$^1$H NMR (300 MHz, D$_2$O): δ 7.96 (d, J=8.1 Hz, 1H, 6"-H), 5.97-5.94 (m, 2H, 5"-H, 1'-H), 5.55 (dd, J=7.8, 3.3 Hz, 1H, 1-H), 4.36-4.33 (m, 2H, 2'-H, 3'-H), 4.26-4.24 (m, 1H, 4'-H), 4.21-4.17 (m, 2H, 5'-H$_2$), 4.13 (t, J=5.1 Hz, 1H, 5-H), 3.88 (m, 1H, 4-H), 3.79-3.69 (m, 3H, 3-H, 6-H$_2$), 2.79-2.75 (m, J=4.2 Hz, 2H, 1'=''-H$_2$), 2.53 (m, 1H, 2-H), 2.24 (s, 3H, 3'''-H$_3$).

$^{31}$P NMR (121 MHz, CDCl$_3$): δ −10.74 (d, J=19.5 Hz), −12.06 (d, J=20.1 Hz).

$^{13}$C NMR (75 MHz, D$_2$O): δ 214.3, 166.3, 151.9, 141.8, 102.9, 96.5, 88.6, 83.6, 74.0, 72.1, 69.9, 68.2, 65.1, 63.9, 61.6, 43.5, 41.6, 30.3.

HRMS (EI) calcd. for C$_{18}$H$_{27}$O$_{17}$N$_2$P$_2$ [M−H]-605.0785, found 605.0803.

Labeling of the O-GlcNAc Peptide.

The peptide TAPTS(O-GlcNAc)TIAPG (SEQ ID NO: 1) (10 μM) was dissolved in 25 mM MOPS buffer, pH 6.7 containing 5 mM MnCl$_2$ and 8 μM reference peptide (ThermoFinnigan, San Jose, Calif.). Labeling agent 1 and mutant Y289L GalT were added to final concentrations of 1 mM and 100 ng/μL, respectively. Prior to enzyme addition, an aliquot of the—reaction was removed as an initial time point for LC-MS analysis. Reactions were incubated at 4° C. for 6 h, after which an aliquot of the reaction mixture was removed for product analysis by LC-MS. The remainder of the reaction was diluted 5-fold into PBS (final concentration: 10.1 mM Na$_2$HPO$_4$, 1.76 mM KH$_2$PO$_4$, 1137 mM NaCl, 2.7 mM KCl, pH 6.7), and N-(aminooxyacetyl)-N'-(D-biotinoyl) hydrazine (Molecular Probes, Eugene, Oreg.) was added to a final concentration of 12 mM. After 8 h at 25° C., the extent of biotin-oxime product was measured by LC-MS. Optimization of the experimental parameters suggested that a 6000:1 molar ratio of aminooxy biotin was optimal for complete conversion to the oxime product. Note that different batches of aminooxy biotin were found to contain variable amounts of TFA salts, affecting the final pH of the biotinylation reaction. Labeling reactions with wild-type GalT were performed identically, with the exception that reactions were incubated at 37° C. for 12 h.

LC-MS Monitoring of O-GlcNAc Peptide Labeling Reactions.

Liquid chromatography and mass spectrometry (LC-MS) were performed on an LCQ Classic ion trap mass spectrometer (ThermoFinnigan, San Jose, Calif.) interfaced with a Surveyor HPLC system (ThermoFinnigan, San Jose, Calif.). Approximately 10 pmoles of peptide from each labeling reaction was loaded onto a Luna column (2 mm i.d.×50 mm) prepacked with 3 μm 100 Å C18 RP particles. Flow rate was maintained at 190 μL/min with a gradient optimized for separation of the O-GlcNAc peptide from labeled products. LC buffer A comprised 2% CH$_3$CN in 0.1M aqueous AcOH and buffer B comprised 90% CH$_3$CN in 0.1M aqueous AcOH. The gradient comprised 0-3 min, 2% B; 3-6 min, 2-11% B; 11-14.5 min 11-27.5% B, 14.5-18 min 27.5-100% B; 18-22 min 100% B where the initial 5 minutes of flow were diverted to waste in order to avoid contamination of the mass spectrometer with salts. The LCQ was operated in automated mode using Xcalibur™ software. The electrospray voltage was 4.5 kV and the heated capillary was 200° C. Ion injection time was set at 200 ms for full MS scan mode of operation (3 microscans per scan). The ion selection window was set at 500-1700 m/z for all experiments.

FIG. 6 shows the progress of the ketone chemical handle labeling reaction using Y289L GalT and the subsequent reaction with aminooxy biotin, as monitored by LC-MS. Base peak chromatograms are shown before and 6 h after the addition of ketone analogue 1 and Y289L GalT. Complete conversion of the peptide to the desired ketone chemical handle-labeled product was observed. For reaction with detection agent aminooxy biotin, formation of the oxime product was monitored using an extracted ion chromatogram within the mass range 1319.0-1321.0 m/z and 1633.0-1635.5 m/z, which was generated post-acquisition via the Xcalibur™ software. Extracted ion chromatograms were necessary because the excess biotin in the reaction mixture dominated the base peak chromatograms. No appreciable amounts of the unbiotinylated starting material were observed after 8 h. Mass spectrometric analysis confirmed the identity of each product (FIG. 7).

FIG. 6 shows reverse phase LC-MS analysis of O-GlcNAc peptide labeling reactions at (A) time 0, (B) 6 h after the addition of 1 and Y289L GalT, (C) 8 h after aminooxy biotin addition. Trace D shows aminooxy biotin in the absence of 1, Y289L GalT and O-GlcNAc peptide. A and B represent base peaks chromatograms, and C and D represent the extracted ion chromatograms within the mass range 1319.0-1321.0 m/z and 1633.0-1635.5 m/z. As shown in FIG. 7, peaks c1 and d represent the same biotin impurity. The slight difference in their retention times is due to minor differences in column equilibration time.

FIG. 7 shows electrospray ionization mass spectra of the peaks in FIG. 6. (A) Spectrum of the peptide starting material (peak a), $[M_{GlcNAc}+H]^+=1118.4$. The fragment ion at 915.2 m/z represents the deglycosylated peptide $[M+H]^+$, which was induced during ionization in the mass spectrometer. (B) Spectrum of the ketone product (peak b), $[M_{ketone-GlcNAc}+H]^+=1320.5$. Ions at 1118.4, 915.2, and 661.1 m/z represent the O-GlcNAc glycosylated peptide, the deglycosylated peptide and the doubly charged species of the ketone labeled peptide, respectively. (C) Spectra of the biotin impurity (peak c1), peak c2, and the oxime product (peak c3). The identity of the product was confirmed by ions 1633.6 and 817.7 m/z, which represent the singly and doubly charged species of the O-alkyl oxime product, respectively. The additional fragment ions at 1118.4 and 915.2 m/z correspond to the O-GlcNAc glycosylated and deglycosylated peptide, respectively. (D) Spectrum of the biotin impurity (peak d), obtained by incubating biotin in the absence of labeling agent 1, Y289L GalT and O-GlcNAc peptide. Note that the spectrum matches that of c1, indicating that these peaks arise from aminooxy biotin.

Figure 8A:
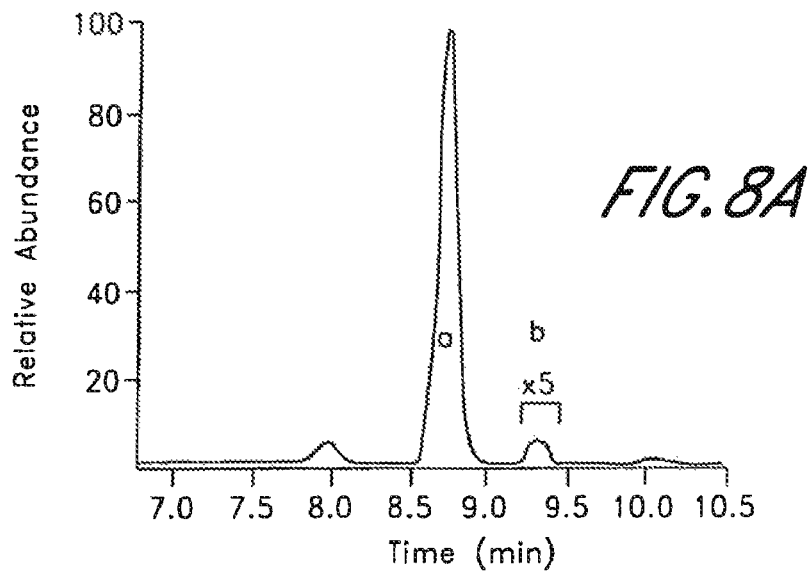
FIG. 8 shows (A) reverse phase LC-MS analysis and accompanying mass spectra of the labeling reaction 12 h after the addition of 1 and wild-type GalT, and (B) the EI mass spectra of peaks a and b confirm the identities of the O-GlcNAc glycosylated peptide, [M$_{GlcNAc}$+H]$^+$=1118 m/z, and the product, [M$_{ketone-GlcNAc}$+H]$^+$=1321.635 m/z and [M$_{ketone-GlcNAc+}$$^2$H]$^{2+}$=661 m/z, respectively.
Figure 8B:
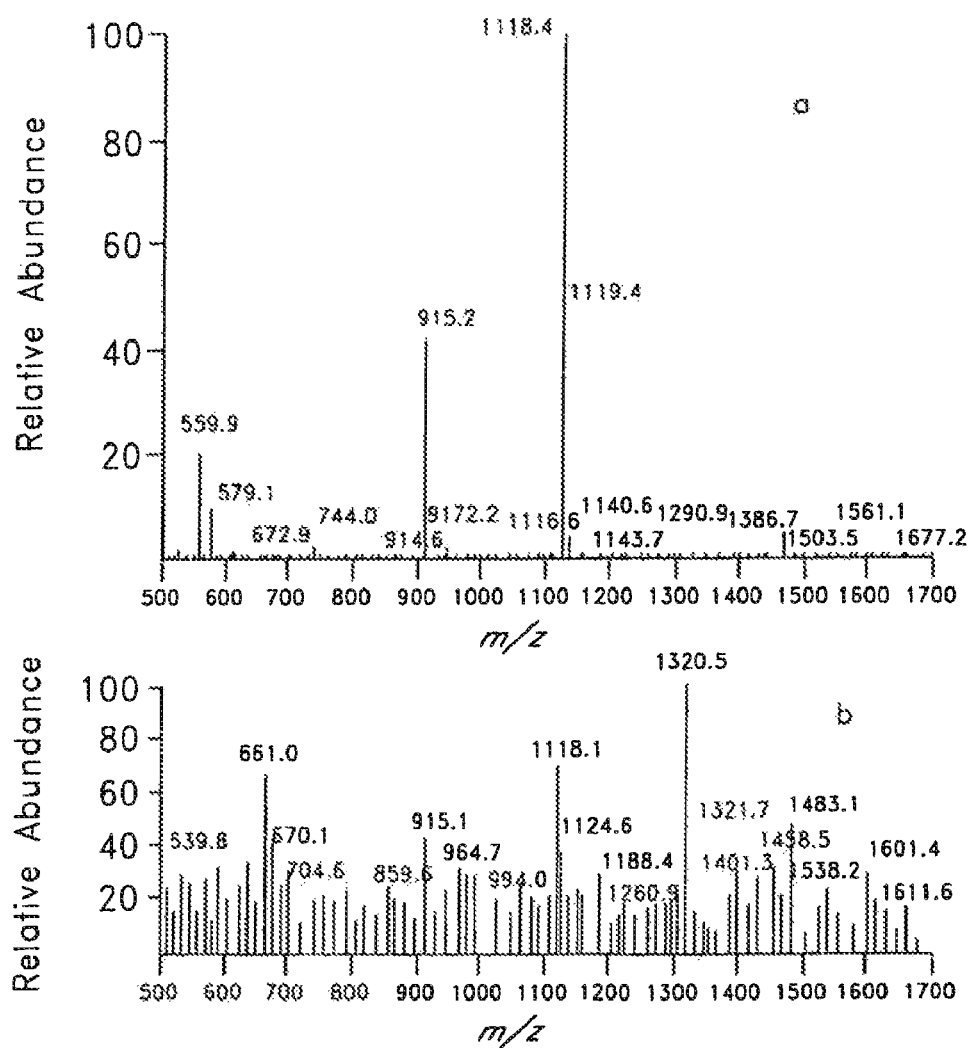

FIG. 8 shows the progress of the labeling reaction using wild-type GalT after 12 h at 37° C. The extent of conversion to ketone-labeled peptide was analyzed by measuring peak areas for the starting material (peak a) and product (peak b) using Xcalibur™ software, under the assumption that the O-GlcNAc peptide and its ketone-labeled analogue had similar ionization potentials. Approximately 1.5% of the desired product was formed with the wild-type Gal T.

FIG. 8 shows (A) Reverse phase LC-MS analysis and accompanying mass spectra of the labeling reaction 12 h after the addition of 1 and wild-type GalT. Both the starting material (a) and ketone labeled peptide product peak (b) are visible in the base peak chromatogram. The latter peak intensity has been amplified 5-fold for clarity. (B) The EI mass spectra of peaks a and b confirm the identities of the O-GlcNAc glycosylated peptide, $[M_{GlcNAc}+H]^+=1118$ m/z, and the product, $[M_{ketone-GlcNAc}+H]^+=1320.635$ m/z and $[M_{ketone-GlcNAc}+2H]^{2+}=661$ m/z, respectively.

Labeling of CREB Protein.

Recombinant O-GlcNAc glycosylated CREB was generated by coexpression of CREB with O-GlcNAc glycosyltransferase in Sf9 cells as described previously.(16) 500 ng of CREB in 20 mM HEPES pH 7.9, 100 mM KCl, 0.2 mM EDTA, 15% glycerol was added to 50 mM MOPS pH 6.45 containing 5 mM $MnCl_2$ and 0.25 mU/µL alkaline phosphatase.(22) Labeling agent 1 and Y289L GalT were then added to final concentrations of 1 mM and 40 ng/µL, respectively. Control reactions without enzyme or analogue 1 were treated identically. Following incubation at 12 h at 4° C., the reactions were diluted 5-fold into PBS containing protease inhibitors (5 µg/mL pepstatin, 5 µg/mL chymostatin, 20 µg/mL leupeptin, 20 µg/mL aprotinin, 20 µg/mL antipain, 0.2 mM PMSF). Aminooxy biotin was added to a final concentration of 2 mM, and the biotinylation reactions were incubated with gentle shaking for 12 h at 37° C. Reactions were aliquoted for analysis and stopped by boiling in SDS-PAGE loading dye. Proteins were resolved by 10% SDS-PAGE, electrophoretically transferred to nitrocellulose, and probed with streptavidin-HRP.

Nitrocellulose blots were blocked for 1 h at RT using 3% periodated-BSA (23) in PBS, rinsed once with TBS (50 mM Tris.HCl, 150 mM NaCl, pH 7.4) containing 0.05% (v/v) tween-20, and probed with streptavidin-HRP (1:2500 to 1:5000) in TBS-0.05% tween for 1 h at RT. Note that we found some variability among different batches of streptavidin. In some cases, blots were probed for 1 h with streptavidin-HRP, rinsed several times with TBS-0.05% tween, and reprobed with another aliquot of streptavidin-HRP. After probing with streptavidin, membranes were rinsed and washed 5×10 min with TBS-0.1% tween containing 0.05% BSA. Streptavidin-HRP signal was visualized by chemiluminescence upon exposure to film. After streptavidin visualization, membranes were stripped in 5 mM $Na_2HPO_4$ pH 7.5, 2% SDS, and 2 mM βME, for 45 min at 60° C., rinsed several times with $dH_2O$, and re-probed with α-CREB antibody as previously described (16) with the modification that the antibody was used at a concentration of 1:400.

Labeling reactions with CREB expressed in *E. coli* were performed identically. To generate the bacterial protein, rat CREB cDNA was cloned into the prokaryotic expression vector pET23b(+) (Novagen, Madison, Wis.) using HindIII and NdeI restriction endonucleases. Electrocompetent BL21 (DE3) cells were electroporated and grown in Luria-Bertani media supplemented with 100 mg/L ampicillin. Protein expression was induced with 0.3 mM isopropyl-β-D-thiogalactopyranoside. Recombinant CREB was purified using Ni-NTA agarose (Qiagen, Valencia, Calif.) as described previously.(16)

Figure 9:
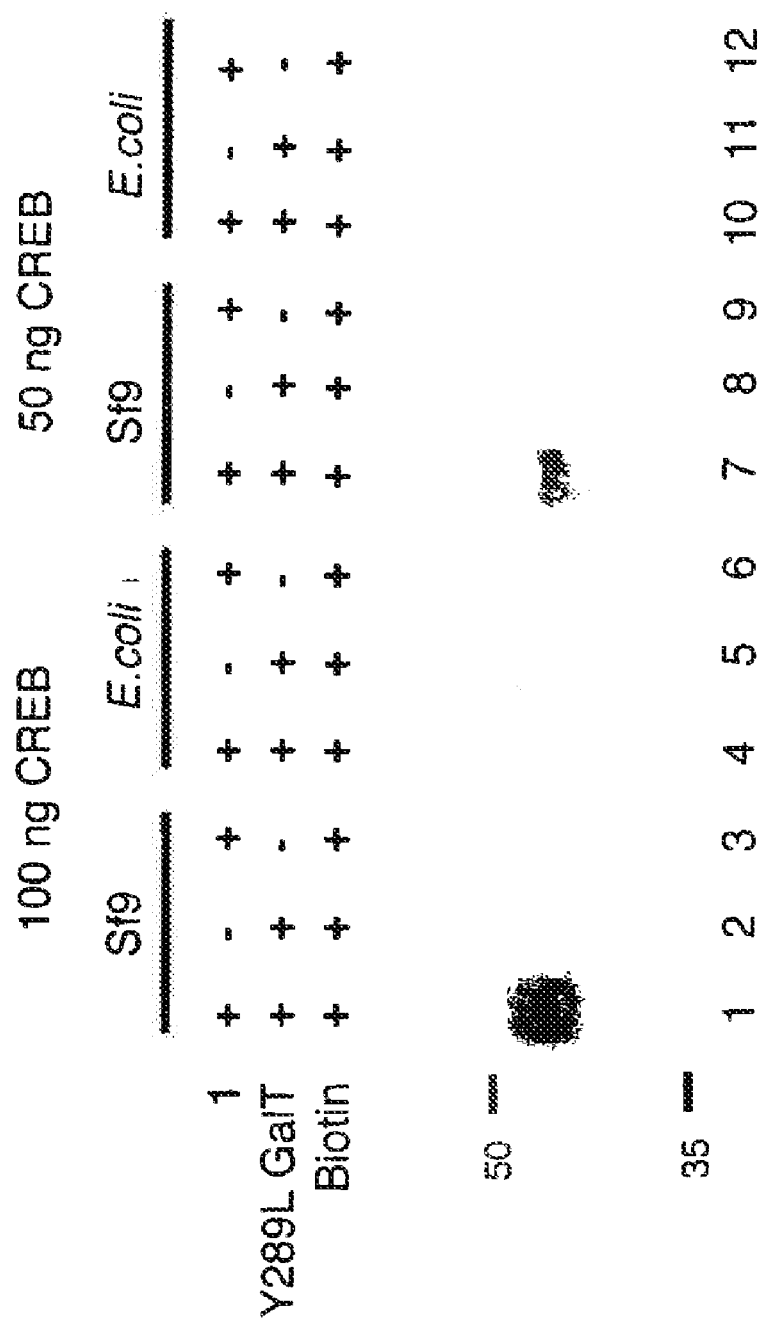
FIG. 9 shows labeling of glycosylated CREB from Sf9 cells (lanes 1-3 and 7-9) or E. coli (lanes 4-6 and 10-12).

As demonstrated in FIG. 9, strong, selective labeling of glycosylated CREB was observed upon treatment with both Y289L GalT and labeling agent 1. With larger quantities of protein, a faint background signal was observed, which was presumably due to the non-specific interaction of aminooxy biotin with the protein. Importantly, the background signal was readily diagnosed using control reactions in the absence of enzyme or labeling agent 1. In the case of *E. coli* CREB, for example, a weak background signal was observed over time, but no selective enhancement of signal was seen in the presence of both enzyme and labeling agent 1, indicating that bacterially expressed CREB was not GlcNAc glycosylated.

FIG. 9 shows labeling of glycosylated CREB from Sf9 cells (lanes 1-3 and 7-9) or *E. coli* (lanes 4-6 and 10-12). Strong streptavidin-HRP signal is observed upon treatment with Y289L GalT and labeling agent 1 (lanes 1 and 7) relative to reactions lacking enzyme or labeling agent 1 (lanes 2-3 and 8-9). In contrast, no selective enhancement of the signal is observed for the negative control, unglycosylated CREB from *E. coli*.

Labeling of α-crystallin.

Bovine lens α-crystallin (a mixture of A (SEQ ID NO: 50) and B (SEQ ID NO: 51) chains) was resolved by SDS-PAGE electrophoresis and Coomassie-stained with standards in order to quantify the amount of A chain in the mixture. For reactions, 8.7 μg of α-crystallin (6.5 μg of A chain) in 20 mM HEPES pH 7.9 was added to 50 mM MOPS pH 6.45 containing 5 mM $MnCl_2$ and 0.25 mU/μL alkaline phosphatase. Labeling agent 1 and Y289L GalT were added to final concentrations of 1 mM and 100 ng/μL, respectively. Reactions were incubated at 4° C. for 18 h and then diluted 5-fold with PBS pH 6.7, protease inhibitors, and aminooxy biotin (6.5 mM final concentration). Biotinylation reactions were incubated with gentle shaking at 25° C. for 12 h. The molar ratio of biotin to α-crystallin was adjusted to minimize background signal, while maintaining reactivity over a reasonable time period. A 4000:1 molar ratio worked successfully for these purposes. After biotinylation, reactions were aliquoted for analysis and subsequently boiled in SDS-PAGE loading dye. Proteins were resolved by 15% SDS-PAGE, transferred to nitrocellulose, and probed with streptavidin-HRP or stained with Coomassie Brilliant Blue (Supplementary FIG. 5). Blotting with streptavidin-HRP was performed as described above and produced a strong signal within 30 min. In contrast, tritium labeling required 8 days to obtain a moderate signal. The difference in time corresponds to ~380-fold improvement in detection sensitivity.

Figure 10:
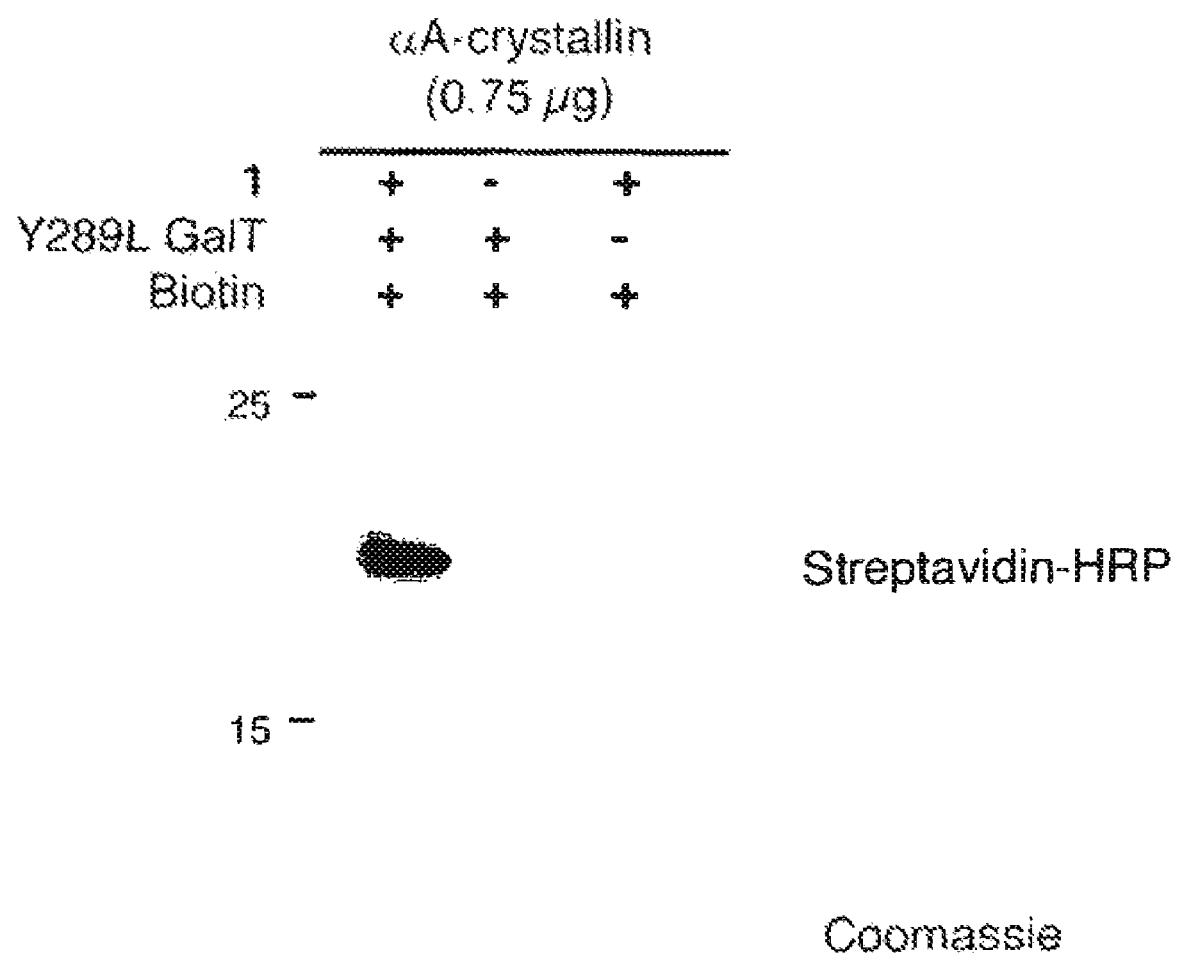
FIG. 10 shows streptavidin-HRP blot of the α-crystallin labeling reactions and the accompanying Coomassie-stained gel of each reaction.

FIG. 10 shows streptavidin-HRP blot of the α-crystallin labeling reactions and the accompanying Coomassie-stained gel of each reaction. Selective labeling of α-crystallin A chain was observed. In contrast, no appreciable labeling was observed in the control reactions lacking labeling agent 1 or Y289L GalT. Coomassie gel bands of similar intensity confirm the presence of comparable amounts of α-crystallin A chain. Faint labeling of the B chain was observed, consistent with reports that it is O-GlcNAc glycosylated.(24)

UDP-[$^3$H]galactose labeling of α-crystallin.

$^3$H-labeling was performed essentially as described.(24, 25) Briefly, 8.7 μg of α-crystallin (6.5 μg of A chain) in 20 mM HEPES pH 7.9 was added to 10 mM HEPES pH 7.9 containing 5 mM $MnCl_2$ and protease inhibitors. UDP-[$^3$H]-galactose was added to a final concentration of 0.03 μCi/μL, and the reaction was initiated with the addition of 25 mU autogalactosylated bovine β 1,4-galactosyltransferase.(25) Reactions were incubated at 37° C. for 1 h 15 min. Reactions were subsequently aliquoted for analysis and stopped by boiling with SDS-PAGE loading dye. Proteins were resolved by 15% SDS-PAGE, stained with Coomassie Brilliant Blue, incubated with Amplify reagent, and dried for subsequent exposure to Hyperfilm MP at −80° C.

Western Blotting of α-Crystallin Using Antibodies RL-2 and CTD110.6.

α-Crystallin, and appropriate positive and negative controls were resolved by 15% SDS-PAGE. All Western blotting steps were performed at RT unless otherwise noted. Western blotting with the RL-2 antibody was performed according to reported methods (26) with minor changes suggested by the manufacturer to reduce background noise. α-Crystallin and controls were electrophoretically transferred to nitrocellulose blots, and the blots were blocked for 1 h in 5% BSA in high salt (250 mM) TBS-1% tween-20 (hsTBS-T). RL-2 antibody, at a concentration of 1:2000, was subsequently added in blocking buffer and blots were incubated for 1.5-2 h. Blots were then rinsed with hsTBST and washed 6×5 min. Secondary goat anti-mouse IgG antibody was applied at a concentration of 1:10,000 in hsTBS-T containing 1% BSA. After 1 h, blots were rinsed and washed as described before chemiluminescence detection on film (FIG. 11A). Western blotting with the CTD10.6 antibody was performed according to manufacturer's recommendations. Briefly, α-crystallin and controls were transferred to PVDF and washed 2×15 min with TBS-0.1% tween-20 (TBST). Blots were blocked in TBST containing 3% BSA for 1 h, rinsed 2× with TBST, and probed with CTD110.6 (1:2500) in blocking buffer for 1 h. Blots were then rinsed 2× with TBST and washed 2×5 min. Secondary goat anti-mouse IgM antibody was applied at a concentration of 1:10,000 in blocking buffer for 1 h, and blots were subsequently rinsed with TBST and washed 5×5 min before chemiluminescence detection on film (FIG. 11B).

Figure 11:
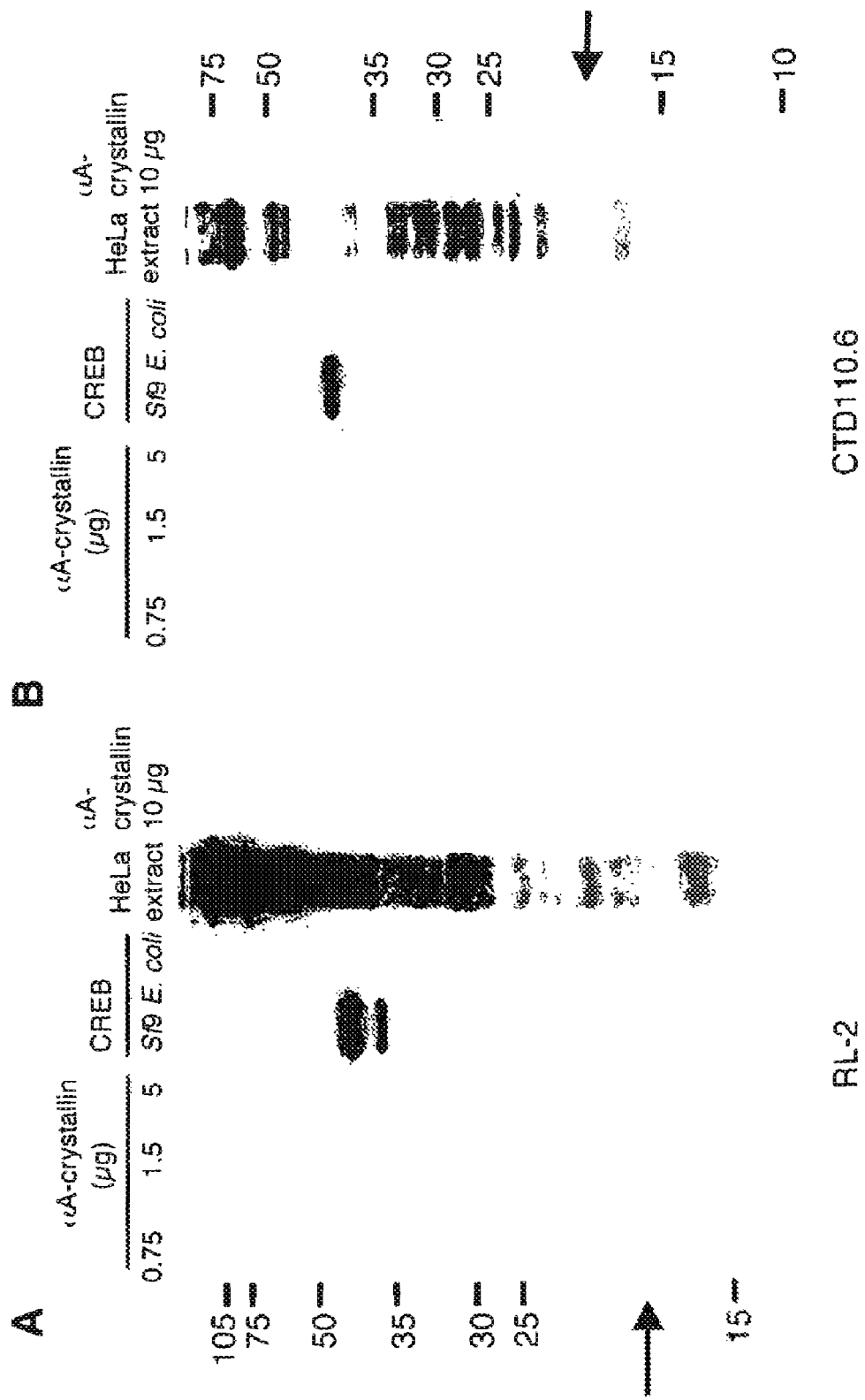
FIG. 11 shows Western blots of α-crystallin using the RL-2 antibody (A) and CTD110.6 antibody (B).

FIG. 11 shows Western blots of α-crystallin using the RL-2 antibody (A) and CTD110.6 antibody (B). Both antibodies effectively detected the O-GlcNAc present on the CREB positive control and HeLa nuclear lysates, while the negative control, unglycosylated CREB from *E. coli*, remained undetected. However, the antibodies failed to appreciably detect the O-GlcNAc present on α-crystallin, even when 10 μg of protein was used. The arrow marks the anticipated position of α-crystallin in the gel.

WGA Lectin Blotting of α-Crystallin.

WGA western blotting was performed essentially as described.(25, 27) Briefly, α-crystallin and controls were resolved by 15% SDS-PAGE and electrophoretically transferred to nitrocellulose. Blots were blocked for 1 h in 3% periodate-treated BSA in PBS, rinsed 2×15 min with PBS-0.05% tween-20 (PBST), and probed for 2 h with WGA-HRP (1:8000 in PBST). Subsequently, blots were rinsed with PBST, washed 3×10 min, then 3×20 min before chemiluminescence detection on film (FIG. 12).

Figure 12:
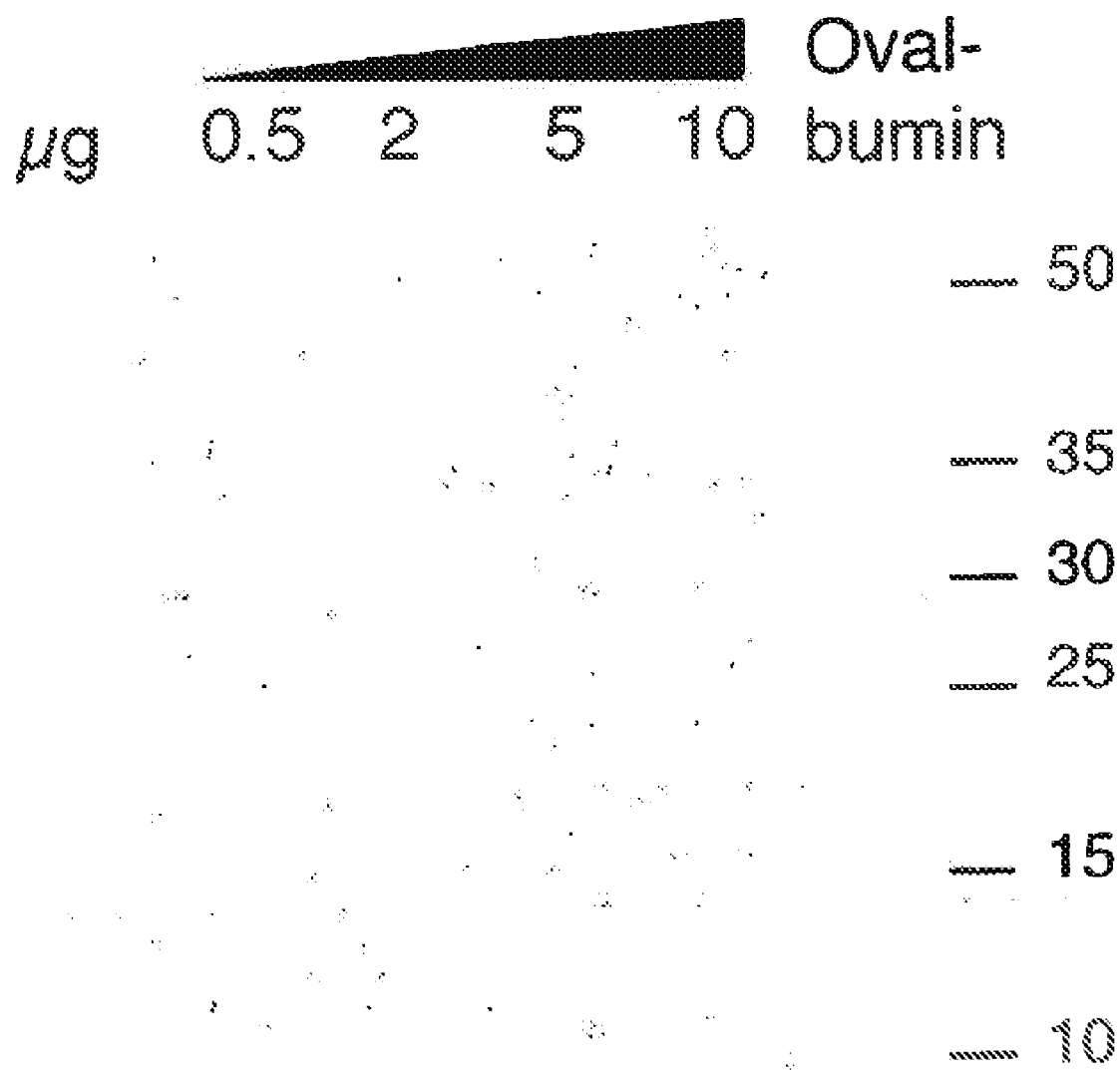
FIG. 12 shows blotting of α-crystallin using WGA lectin.
Figure 13:
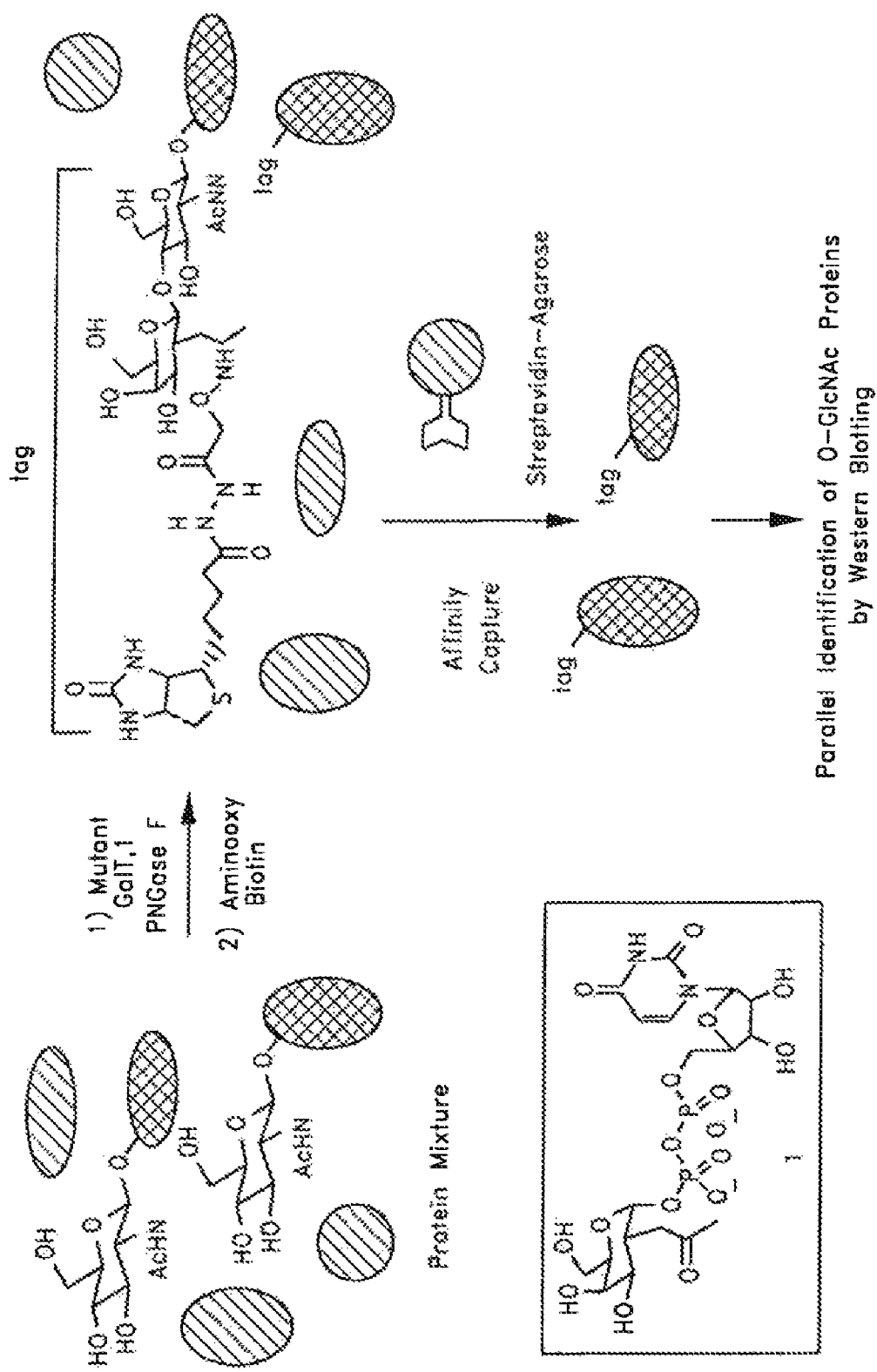
FIG. 13 shows a general strategy for identifying O-GlcNAc proteins from cell lysates.

FIG. 12 shows blotting of α-crystallin using WGA lectin. While WGA detected the N-linked terminal GlcNAc groups of the ovalbumin positive control, it could not detect the O-GlcNAc moiety on α-crystallin.

EXAMPLE 2

Parallel Identification of O-GlcNAc Modified Proteins from Cell Lysates (96)

The preferred embodiments can be used for detecting a protein for O-GlcNAc modification. The preferred embodiments circumvent the need to purify individual proteins, accommodate any cell type or tissue, and can be extended to the mapping of modification sites. The results herein identified four new O-GlcNAc glycosylated proteins of low cellular abundance (c-Fos, c-Jun, ATF-1, and CBP) and two new glycosylation sites on the protein O-GlcNAc transferase (OGT (SEQ ID NO: 49)). Using the preferred embodiments, multiple proteins could be readily interrogated in parallel by Western blotting using antibodies selective for proteins of interest.

The preferred embodiments have several notable advantages. The preferred embodiments accelerate the discovery of O-GlcNAc proteins by eliminating the need to purify individual proteins. Virtually any protein could be examined for the modification as a wide variety of antibodies are available for Western blotting. The enhanced sensitivity of the preferred embodiments relative to existing methods would enable identification of even low-abundance regulatory proteins.(31) Moreover, the use of cell lysates rather than intact cells would capture the physiologically relevant glycosylation state of proteins without perturbing metabolic pathways.

Finally, the ability to target specific proteins across different tissue or cell types (32) would complement emerging proteomic technologies.(29A)

Implementation of a parallel approach utilizes the preferred embodiments to study complex mixtures. HeLa cells were lysed under denaturing conditions to preserve the physiological glycosylation state of the proteins. The cell extract was then labeled with the labeling agent 1 with use of mutant GalT for 12 h at 4° C. N-linked glycans could be removed simultaneously during this incubation period by treatment with PNGaseF.(33) Following reaction with an aminooxy biotin, the biotinylated O-GlcNAc proteins were captured with streptavidin-agarose beads, resolved by SDS-PAGE, and transferred to nitrocellulose membrane. To determine whether the captured proteins had been biotinylated, the membrane was blotted with streptavidin conjugated to horseradish peroxidase (HRP). A strong chemiluminescence signal was observed, indicating successful labeling of proteins from extracts (FIG. 14A). Little signal was detected in the absence of either enzyme or labeling agent 1, strongly suggesting that O-GlcNAc-modified proteins had been specifically labeled and captured.

To confirm the results, the transcription factor cAMP-responsive element binding protein (CREB) was studied. CREB is a low-abundance protein that contains only two major O-GlcNAc clycosylation sites,(34) and as such, it represents a challenging cellular target. CREB was readily detected in the captured fraction by Western blotting using an anti-CREB antibody (FIG. 14B). In contrast, a protein that lacks O-GlcNAc pendant moiety (25), cAMP-dependent protein kinase (PKA), was not detected. These results demonstrate that low-abundance O-GlcNAc proteins from cells can be selectively captured and identified.

Figure 14:
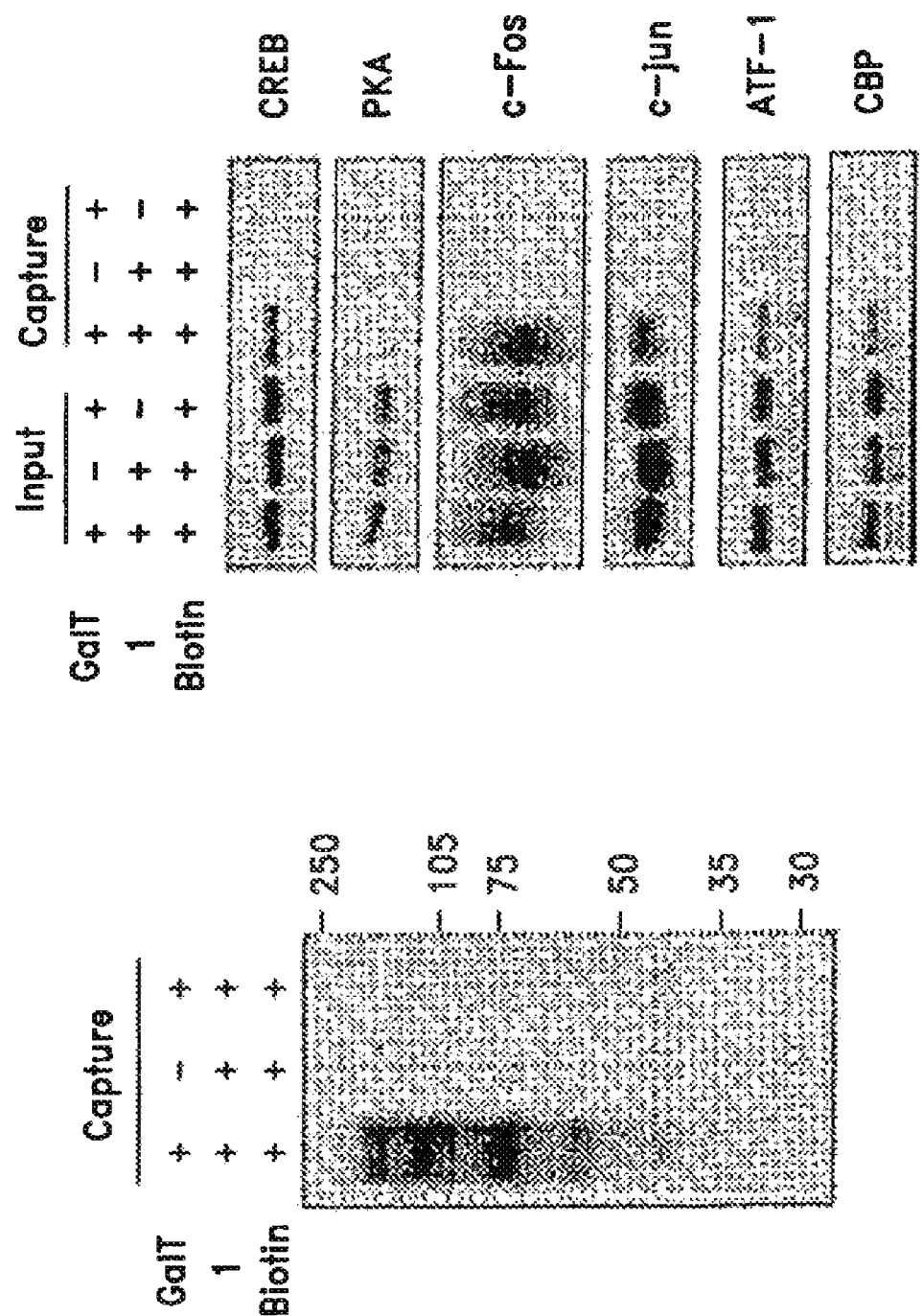
FIG. 14 shows (A) captured proteins from HeLa cell lysates following labeling, and (B) labeled lysates prior to (Input) or following (Capture) affinity capture as probed by Western blotting using antibodies against the indicated proteins.

The approach was next applied toward the parallel identification of novel proteins. Although the AP-1 transcription factor complex has been shown to be GlcNAc modified (36), the specific proteins and nature of the glycosidic linkage have remained unresolved. FIG. 14 shows that the AP-1 family members c-Fos and c-Jun were captured, indicating that both proteins are O-GlcNAc glycosylated. As independent confirmation, the traditional approach of UDP-[$^3$H]galactose and GalT (33), followed by immunoprecipitation of c-Fos was used. Notably, tritium labeling required 1000 h of exposure to film for strong detection. In contrast, the preferred embodiments permitted detection of c-Fos within minutes.

FIG. 14 shows (A) captured proteins from HeLa cell lysates following labeling as indicated. The blot was probed with streptavidin-HRP to detect biotinylated proteins. (B) Labeled lysates prior to (Input) or following (Capture) affinity capture as probed by Western blotting using antibodies against the indicated proteins.

The preferred embodiments enable study of the O-GlcNAc modification across structurally or functionally related protein families. ATF-1, a structural homologue and dimerization partner of CREB (37), shares only partial sequence identity within the region of CREB glycosylation.(34) Nonetheless, A F-1 was present in the captured fraction, indicating that both family members are subject to O-GlCNAc glycosylation in HeLa cells.

The preferred embodiments also permitted the identification of an entirely new class of O-GlcNAc-glycosylated proteins, histone acetyltransferases (HAT). CREB-binding protein (CEP) is a HAT involved in chromatin remodeling and activation of numerous transcription factors.(38) As shown in FIG. 14B, it was found that CBP is O-GlcNAc glycosylated. This finding is interesting in light of recent observations that O-GlcNAc transferase (OGT), the enzyme that catalyzes the modification, interacts with a histone deacetylase complex to promote gene silencing.(39) These results demonstrate that a broader set of transcriptional components are O-GlcNAc modified, and they support the notion that O-GlcNAc may serve as a general mechanism for transcriptional control.

Figures 15A, 15B:
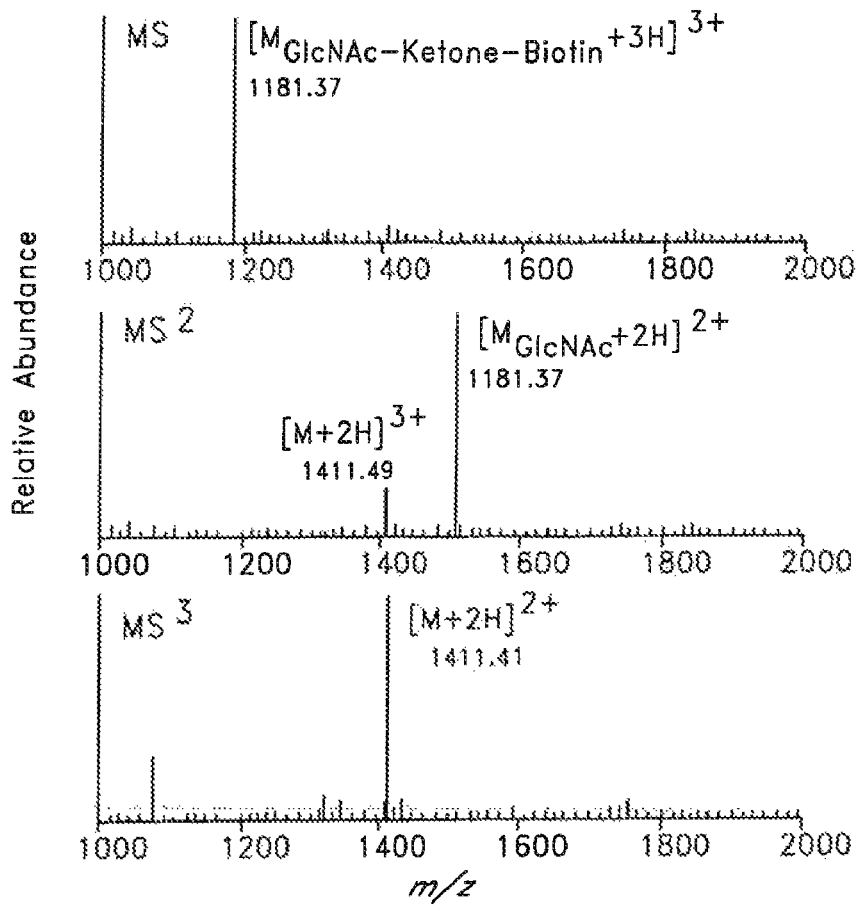
FIG. 15 shows (A) LC-MS signature of the enriched O-GlcNAc peptide from CREB, and (B) glycosylated peptides from OGT.

Finally, the preferred embodiments were extended to the mapping of glycosylation sites. The challenge of identifying specific modification sites has deterred efforts to understand posttranslational modifications, and mass spectrometry enrichment strategies are often required.(40) The preferred embodiments could be applied to the enrichment of O-GlcNAc peptides and this was demonstrated using CREB. CREB from Sf9 cells was labeled and digested with trypsin. Following avidin chromatography, enrichment of a CREB glycopeptide (34) was observed by MALDI-TOF MS and LC-MS (FIG. 15A). Importantly, the ketone-biotin moiety facilitated the identification of the O-GlcNAc peptide by providing it unique fragmentation pattern upon tandem MS. To illustrate the potential of the approach to identify new glycosylation sites, OGT from Sf9 cells was labeled and analyzed as above. Two regions of glycosylation were identified within the catalytic domain of OGT (aa 1037-1046) and the ninth tandem tetratricopeptide repeat (aa 390-406), a highly conserved motif that mediates protein-protein interactions between OGT and its regulatory partners (FIG. 15B). The location of these sites within important functional domains suggests that OGT may regulate its own activity via autoglycosylation.

FIG. 15 shows (A) LC-MS$^n$ signature of the enriched O-GlcNAc peptide from CREB. (B) Glycosylated peptides from OGT. Summary of the b and y fragment identified by MS$^4$.

The preferred embodiments permit endogenous or overexpressed proteins isolated from cell or whole tissue extracts to be rapidly interrogated for the O-GlcNAc modification. The preferred embodiments detect low-abundance proteins, circumvent the need to purify individual proteins, and can be extended to the mapping of glycosylation sites. Finally, the preferred embodiments can advance the study of other post-translational modifications, as well as disease states associated with these post-translational modifications, such as cancer, Alzheimer's disease, neurodegeneration, cardiovascular disease, and diabetes.

General Reagents and Methods:

Unless otherwise noted, reagents were purchased from the commercial suppliers Fisher (Fairlawn, N.J.) and Sigma-Aldrich (St. Louis, Mo.), and were used without further purification. Protease inhibitors were purchased from Sigma-Aldrich or Alexis Biochemicals (San Diego, Calif.). Bovine GalT, ovalbumin and sepharose 6B were obtained from Sigma-Aldrich. Uridine diphospho-D-[6$^3$H]-galactose, Hyperfilm ECL, Hyperfilm MP and Amplify reagent were purchased from Amersham Biosciences (Piscataway, N.J.). Peptide N-glycosidase F (PNGase F) was purchased from New England Biolabs (Beverly, Mass.). Sequencing grade trypsin was from Promega (Madison, Wis.). Agarose-conjugated protein A, agarose-conjugated streptavidin, SuperSignal West Pico chemiluminescence reagents, horseradish peroxidase (HRP)-conjugated streptavidin and anti-rabbit IgG antibody were from Pierce (Rockford, Ill.). Nitrocellulose membrane was from Schleicher and Schuell (Keene, N.H.). Dulbecco's modified Eagle media (DMEM), fetal bovine serum and penicillin/streptomycin were from Gibco (Carlsbad, Calif.). N-(aminooxyacetyl)-N'-(D-biotinoyl) hydrazine was purchased from Dojindo (Gaithersburg, Md.). Anti-CREB, anti-ATF-1 and HRP-conjugated, anti-sheep IgG antibodies were from Upstate (Charlottesville, Va.). Anti-PKA catalytic subunit (C-20), anti-c-Fos (4), anti-c-Jun (H-79), and anti-CBP (A-22) antibodies were from Santa Cruz Biotechnology (Santa Cruz, Calif.). CTD 110.6 anti-O-GlcNAc antibody was from Covance (Princeton, N.J.). Mutant GaiT (Y289L) was expressed and purified as described previously.(41) All protein concentrations were measured using the Bradford assay (Bio-Rad Laboratories, Hercules, Calif.).

Preparation of HeLa Cell Extracts.

HeLa (human cervical adenocarcinoma) cells were cultured in 37° C. humidified air with 5% $CO_2$ in DMEM supplemented with fetal bovine serum (10%), penicillin (100 U/mL) and streptomycin (100 µg/mL). Prior to lysis, HeLa cells were 20% serum starved in serum-free DMEM for 48 h and induced with 20% serum for 2 h.(42) In some experiments, the culture medium was supplemented with 10 mM glucosamine during the last 5 h of serum starvation and throughout serum induction. After induction, cells from a 100 mm dish were trypsinized and pelleted. The pellet was washed with ice-cold TBS (Tris-buffered saline, 50 mM Tris-HCl pH 7.4, 150 mM NaCl), resuspended in 0.5 mL of boiling lysis buffer (20 mM HEPES pH 7.9, 0.5% SDS, 10 mM DTT), sonicated for 10 s, and boiled for 10 min. After centrifugation at 21,500×g for 15 min, the supernatant was collected as denatured HeLa extract. Denatured extracts were stable when stored at −80° C. for several weeks.

Labeling and Capturing O-GlcNAc Modified Proteins.

One volume of denatured HeLa extract (typically 700 µg of total protein in 70 µL) was added into four volumes of dilution buffer (6.7 mM HEPES pH 7.9, 1.25% Nonidet P-40 (NP-40), 75 mM NaCl, 1.5 mM DTT) containing protease inhibitors (15 µg/mL antipain, 15 µg/mL leupeptin, 7.5 µg/mL chymostatin, 7.5 µg/mL pepstatin, 0.75 mM phenylmethylsulfonyl fluoride). Diluted extract was then supplemented with 5 mM $MnCl_2$, 1.25 mM adenosine 5'-diphosphate, 0.5 mM labeling agent 1, 20 gg/mL mutant GalT and 2500 U/mL PNGase F. The reaction mixture was incubated at 4° C. for 12 h, and dialyzed into buffer A (8 mM HEPES pH 7.9, 5 M urea, 25 mM NaCl) twice for 4 h at room temperature. Following dialysis, NP-40 and SDS were added to the final concentrations of 0.5% and 0.05%, respectively. The sample was then acidified to pH 4.8 by adding 0.3 M NaOAc pH 3.7 to a final concentration of 1.8 mM and mixed for 10 min. After centrifugation at 21,500×g for 10 min, the supernatant was collected and the aminooxy biotin derivative was added to a final concentration of 3 mM. After incubation at room temperature for 16 h, the sample was neutralized by adding 0.5 M HEPES pH 7.9 to a final concentration of 33 mM, followed by dialysis into buffer B (10 mM HEPES pH 7.9, 6 M urea) three times for 4 h, and into buffer C (10 mM HEPES 7.9, 150 mM NaCl, 1 mM DTT) twice for 3 h. Dialyzed sample was collected and denoted as labeled HeLa extract.

Labeled HeLa extract was supplemented with protease inhibitors (10 µg/mL antipain, 10 µg/mL leupeptin, 5 µg/mL chymostatin, 5 µg/mL pepstatin, 0.5 mM phenylmethylsulfonyl fluoride), and pre-cleared with sepharose 6B beads (30 1.tL/100 µg of proteins) for 1 h at 4° C. After centrifugation at 5,000×g for 3 min, the supernatant was collected and incubated with agarose-conjugated streptavidin (30 µL/100 µg of proteins) for 2 h at 4° C. Following centrifugation at 5,000×g for 3 min, the supernatant was removed, and the beads were washed three times with 8 volumes of low salt wash buffer (0.1 M $Na_2HPO_4$ pH 7.5, 0.15 M NaCl, 1% Triton X-100, 0.5% sodium deoxycholate, 0.1% SDS) and three times with high salt wash buffer (0.1 M $Na_2HPO_4$ pH 7.5, 0.5 M NaCl, 0.2% Triton X-100). After washing, the beads were boiled for 10 min in 2.5 volumes of elution buffer (50 mM Tris-HCl 6.8, 2.5% SDS, 100 mM DTT, 10% glycerol, 2 mM biotin). After centrifugation at 2,000×g for 1 min, the supernatant was collected as the captured material.

PNGase F Deglycosylation of Ovalbumin.

Proteins containing N-linked glycans with terminal GlcNAc groups can also be labeled by GalT, and, therefore, it is important to remove N-linked glycans by PNGase F to ensure labeling specificity.(43, 44) Ovalbumin, a glycoprotein with N-linked glycans and terminal GlcNAc moieties (45), was chosen as a positive control to demonstrate that N-linked glycans in HeLa extracts can be effectively removed under the specified reaction conditions.

Purified ovalbumin was dissolved in lysis buffer to a final concentration of 2 mg/ml and boiled for 10 min. After denaturation, ovalbumin was diluted and subjected to mutant GalT/PNGase F treatment as described for denatured HeLa extracts. Assuming 10% of HeLa cell proteins were N-glycosylated, the amount of ovalbumin treated in parallel represented a 2-fold excess. Following incubation at 4° C. for 12 h, ovalbumin samples were analyzed by SDS-PAGE and visualized by Coomassie staining.

Figure 16A:
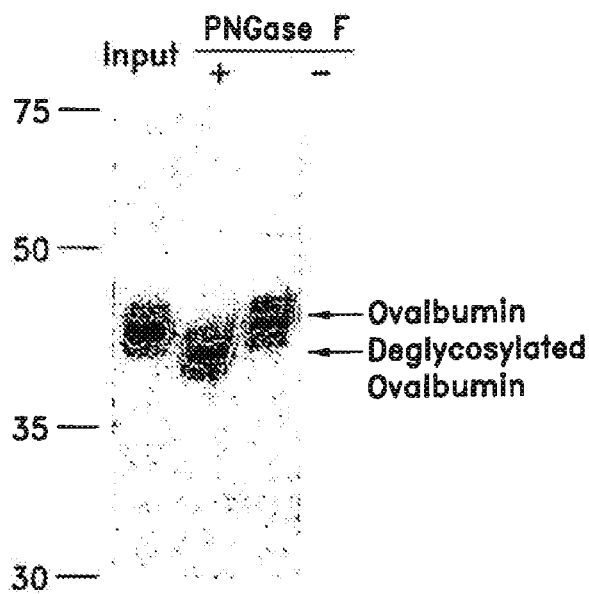
FIG. 16 shows (A) removal of N-linked glycans from ovalbumin using PNGase F, and (B) immunoprecipitation of radiolabeled c-Fos.

FIG. 16A shows that PNGase F-treated ovalbumin has increased gel mobility compared to either denatured ovalbumin (Input) or ovalbumin treated with mutant GalT but not PNGase F. The drastic shift in mobility is due to the removal of N-linked glycans by PNGase F. These results confirm the effectiveness of N-linked glycan removal under the specified reaction conditions.

FIG. 16A shows removal of N-linked glycans from ovalbumin using PNGase F. Denatured ovalbumin (left lane), PNGase F/GalT treated (middle lane) and GalT treated (right lane) ovalbumin were analyzed by SDS-PAGE and visualized by Coomassie staining. Increased gel mobility of PNGase F-treated ovalbumin indicates removal of N-linked glycans under the Gal T labeling conditions.

Western Blotting with HRP-Conjugated Streptavidin.

Streptavidin-captured materials from labeled HeLa extracts were resolved by SDS-PAGE and transferred to nitrocellulose membranes. Membranes were blocked with 5% BSA in phosphate-buffered saline (pH 7.4) for 1 h at room temperature, followed by 1 h incubation with HRP-streptavidin in TBS with 0.05% Tween-20 (TBST). After six washes for 10 min in TBST, biotinylated proteins were visualized by chemiluminescence.

Immunoblotting for the Parallel Identification of O-GlcNAc Proteins.

For each immunoblotting analysis, material captured from 20-100 µg of HeLa extracts was loaded on the gel, along with 20% of the corresponding input material prior to capture. After SDS-PAGE, proteins were transferred to nitrocellulose membranes. Membranes were blocked with 5% non-fat milk in TBST for 30 min at room temperature, and then incubated with an antibody specific for the protein of interest in blocking buffer for 1-2 h at room temperature. Following three washes for 10 min in TBST, membranes were incubated with the HRP-conjugated secondary antibody in blocking buffer for 1 h at room temperature, and washed three more times. Individual proteins were visualized by chemilumineseence.

Radiolabeling and Immunoprecipitation of c-Fos.

O-GlcNAc glycosylation of c-Fos was confirmed using standard procedures (44) HeLa cell extract was prepared as described above, except that the lysis buffer contained 50 mM Tris-HCl pH 7.5 instead of HEPES. One volume of HeLa extract was added to four volumes of dilution buffer (10 mM Tris-HCl 7.5, 1.25% NP-40, 2.5 mM CHAPS) with protease inhibitors (10 μg/mL antipain, 10 μg/mL leupeptin, 5 μg/mL chymostatin, 5 μg/mL pepstatin, 0.5 mM phenylmethylsulfonyl fluoride). Diluted extract was then supplemented with 5 mM $MnCl_2$, 1.25 mM adenosine 5'-diphosphate, 625 mU/mL bovine GalT and 67 p.Ci/mL UDP-[$^3$H]galactose. After incubation at 4° C. for 12 h, the radiolabeling reaction was quenched by the addition of EDTA to a final concentration of 10 mM.

Radiolabeled extract (150 μg) was pre-cleared by incubation with 10 μL of protein A-agarose beads at 4° C. for 1 h. Following centrifugation at 2,000×g for 20 s, the supernatant was collected and incubated with 20 μL of protein A-agarose beads that had been pre-incubated with 2 μg of anti-c-Fos antibody. After 4 h incubation at 4° C., the beads were washed twice with wash buffer (20 mM Tris-HCl pH 7.5, 1% NP-40, 0.1% SDS, 2 mM CHAPS). Immunoprecipitated material was eluted by boiling for 10 min with 50 μL of elution buffer (1% SDS, 1% 2-mercaptoethanol). After centrifugation at 2,000×g for 1 min, the supernatant was collected and diluted into 50 μL of PNGase F buffer (0.15 M $Na_2HPO_4$ pH 8.6, 15 mM EDTA, 5% NP-40). 1250 U of PNGase F was then added to the sample, followed by 12 h incubation at 37° C. and SDS-PAGE analysis. After Coomassie staining and destaining, the gel was immersed in 2% glycerol for 30 min, followed by Amplify reagent for 30 min, and dried under vacuum. Tritium-labeled proteins were detected by autoradiography.

Figure 16B:
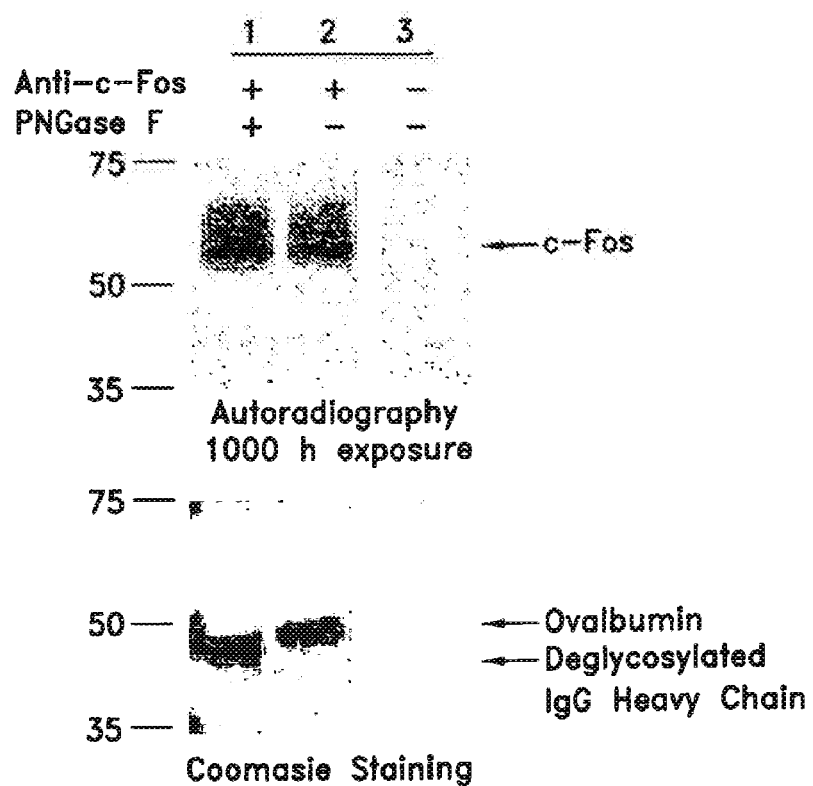

As shown in FIG. 16B, immunoprecipitated c-Fos was detected by autoradiography after 1000 h. Importantly, PNGase F treatment removed N-linked glycans from the IgG heavy chain as expected,(46) but c-Fos radioactivity remained unaffected. These results confirm that c-Fos is O-GlcNAc glycosylated.

FIG. 16B shows immunoprecipitation of radiolabeled c-Fos. HeLa extracts were first labeled with bovine GalT and UDP-[$^3$H]galactose, and c-Fos was immunoprecipitated in the presence (lanes 1 and 2) or absence (lane 3) of anti-c-Fos antibody, followed by incubation with PNGase F (lane 1). After SDS-PAGE analysis, gels were Coomassie stained (lower panel), dried, and subjected to autoradiography (upper panel). Radiolabeled c-Fos was specifically pulled-down by the anti-c-Fos antibody. Removal—linked glycans with PNGase F enhanced the mobility of IgG heavy chain (lower panel, lanes 1 and 2) but did not affect the tritium labeling of c-Fos (upper panel, lanes 1 and 2), indicating that c-Fos is O-GlcNAc glycosylated.

Labeling of CREB and O-GlcNAc Transferase (OGT) for Mass Spectrometry.

Baculovirus preparation and protein expression were performed as described previously.(47) CREB (2 μg) or OGT (10 μg) in 20 mM HEPES pH 7.9, 100 mM KCl, 0.2 mM EDTA, 15% glycerol were supplemented with 5 mM $MnCl_2$. Labeling agent 1 and Y289L GalT were added to final concentrations of 750 μM and 40 ng/μL, respectively. Control reactions without enzyme or labeling agent 1 were treated identically. Following incubation at 12 h at 4° C., the reactions were diluted 2-fold with saturated urea. 2.7 M NaOAc pH 3.9 was added to a final concentration of 50 mM and a final pH of 4.8. Aminooxy biotin derivative was added to a final concentration of 5 mM, and the biotinylation reactions were incubated with gentle shaking for 20-24 h at 23° C. Reactions were aliquoted for analysis by Western blotting or mass spectrometry and stopped by boiling in SDS-PAGE loading dye. Proteins were resolved by 10% SDS-PAGE and either electrophoretically transferred to nitrocellulose or stained with Coomassie Brilliant Blue. Western blotting with streptavidin-HRP was performed as described above to confirm successful labeling.

In-Gel Trypsin Digestion, Avidin Enrichment and MALDI-TOF Analysis of Labeled CREB and OGT.

CREB and OGT bands were excised from Coomassie-stained gels and treated essentially as described by Shevchenko et al.(48) Briefly, excised bands were destained overnight in 50% MeOH, 5% AcOH. Destained bands were dehydrated in $CH_3CN$, dried by vacuum, and rehydrated in 10 mM DTT. After 30 min reduction at room temperature, excess DTT was removed, and proteins were alkylated in 50 mM iodoacetamide for 30 min at room temperature in the dark. After alkylation, excess iodoacetamide was removed and protein bands were washed in 100 mM $NH_4HCO_3$ pH 8.0 for 10 min, followed by two successive dehydrations in $CH_3CN$. Wash and dehydration steps were repeated once more, and excess $CH_3CN$ was removed under vacuum. Protein bands were rehydrated in 15 ng/μL trypsin in 50 mM $NH_4HCO_3$ pH 8.0. Excess trypsin solution was removed after rehydration, and 20-30 μL of 50 mM $NH_4HCO_3$ pH 8.0 was then added to cover the gel slices. Proteins were digested overnight at 37° C. Following digestion, peptides were extracted with successive washes of water followed by 50% acetonitrile/5% formic acid in water, and dried by vacuum centrifugation.

A small portion of each sample was saved prior to affinity chromatography for matrix-assisted laser desorption/ionization time-of-flight mass spectrometry (MALDI-TOF MS). The remainder was subjected to avidin affinity chromatography (Applied Biosystems, Foster City, Calif.). Chromatography was performed essentially as described by the manufacturer except that the volume of washes was doubled. Eluted peptides were partially dried by vacuum centrifugation, and a small portion of the eluted peptides was analyzed by MALDI-TOF MS. For the analysis, peptide samples were concentrated on C18 zip tips (Millipore, Bedford, Mass.) and combined with the MALDI matrix (2,5-dihydroxybenzoic acid in 20% $CH_3CN$, 0.1% TFA in water). Spectra were acquired on a PerSeptive Biosystems Voyager-DE Pro at 20,000 kV in the reflector mode.

Figures 17A, 17B:
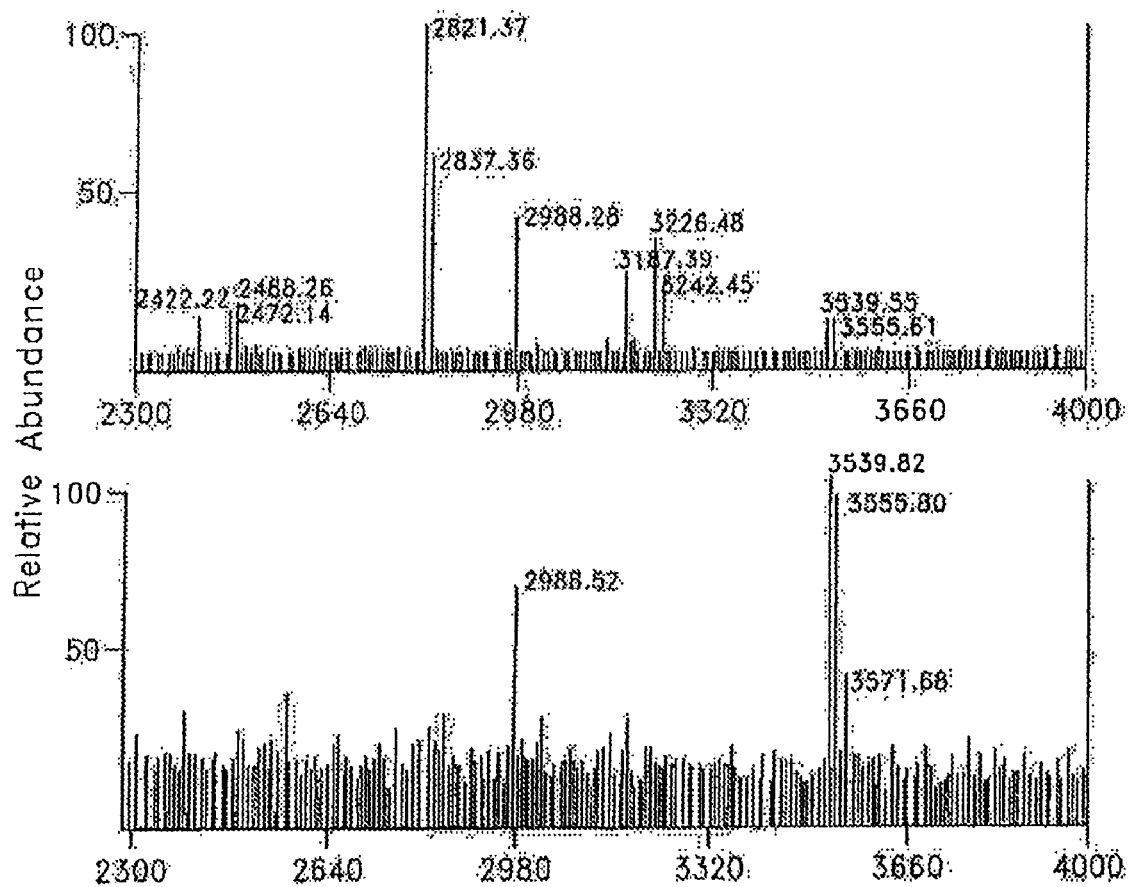
FIG. 17 shows enrichment of CREB O-GlcNAc peptides via the chemoenzymatic strategy: (A) MALDI-TOF spectrum of CREB tryptic peptides prior to avidin chromatography, (B) MALDI-TOF spectrum of the eluent following avidin affinity capture of CREB peptides. The spectrum reveals enrichment of the labeled CREB peptide at m/z 3539.82 as well as two peaks at m/z 3555.80 and 3571.68 that correspond to oxidized forms of this peptide. The peptide at m/z 2988.52 displays some nonspecific interaction with the avidin column and can be readily discerned as unlabeled by LC-MS/MS.

As shown in FIG. 17A, a number of CREB tryptic peptides were observed prior to affinity chromatography. The expected O-GlcNAc peptide $^{256}$TAPTSTIAPGVVMASSPALPTQ-PAEEAAR$^{284}$ (SEQ ID NO: 7),(47) which had been labeled with a ketone-biotin moiety, was present in low abundance (m/z 3539.55). Following avidin chromatography, selective enrichment of this peptide was clearly observed (FIG. 17B). Two additional variants corresponding to multiply oxidized forms of this peptide were also detected. These results demonstrate that O-GlcNAc peptides that are labeled using our chemoenzymatic strategy can be selectively captured for MS analysis.

FIG. 17 shows enrichment of CREB O-GlcNAc peptides via the chemoenzymatic strategy. (A) MALDI-TOF spectrum of CREB tryptic peptides prior to avidin chromatography. The peak at m/z 3539.55 corresponds to the mass of the O-GlcNAc glycosylated peptide labeled with the ketone-biotin moiety. (B) MALDI-TOF spectrum of the eluent following avidin affinity capture of CREB peptides. The spectrum reveals enrichment of the labeled CREB peptide at m/z 3539.82 as well as two peaks at m/z 3555.80 and 3571.68 that correspond to oxidized forms of this peptide. The peptide at m/z 2988.52 displays some nonspecific interaction with the avidin column and can be readily discerned as unlabeled by LC-MS/MS.

The MALDI-TOF MS spectra of the peptides corresponding to OGT was examined. Prior to avidin chromatography, a number of tryptic peptides of OGT were observed (FIG. 18A). Notably, however, no labeled glycopeptides were detected. Following avidin chromatography, significant enrichment of a peak (m/z 2548.16) corresponding to the OGT sequence $^{390}$ISPTFADAYSNMGNTLK$^{406}$ (SEQ ID NO: 2) plus the ketone-biotin moiety was obtained (FIG. 18B). As in the case of CREB, two additional multiply oxidized variants of the captured peptide were observed.

FIG. 18 shows enrichment of OGT O-GlcNAc peptides via the chemoenzymatic labeling strategy. (A) MALDI-TOF spectrum of OGT tryptic peptides prior to avidin chromatography reveals a number of OGT peptides while no labeled O-GlcNAc modified peptides are visible. (B) MALDI-TOF spectrum of eluted peptides following avidin affinity chromatography reveals enrichment of a peak at m/z 2548.16 and two oxidized forms of the same eptide. This mass corresponds to the labeled O-GlcNAc peptide $^{390}$ISPTFADAYSN-MGNTLK$^{406}$ (SEQ ID NO: 2), whose sequence was confirmed by LC-MS/MS. The mass at m/z 2836.77 may correspond to the labeled O-GlcNAc form of the OGT tryptic peptide $^{421}$AIQINPAFADAHSNLASIHK$^{440}$ (SEQ ID NO: 8). However, tandem MS analysis was inconclusive. The mass at m/z 2251.08 does not correspond to theoretical OGT tryptic modified or unmodified peptides and may be a contaminant.

LC-MS/MS Analysis of Avidin-Enriched CREB and OGT Peptides.

Having confirmed the efficacy of the enrichment procedures using MALDI-TOF MS, subsequent analyses were performed directly using LC-MS/MS. Automated nanoscale liquid chromatography and tandem mass spectrometry (LC-MS/MS) were conducted using a ThermoFinnigan Surveyor HPLC and LTQ ion trap mass spectrometer along with a variation of the "vented column" approach described by Licklider et al.(49) Avidin-enriched peptides were loaded onto a 5 cm-long×75 μm i.d. precolumn packed with 5 μm C-18 silica (Monitor 100 A) retained by a Kaisel fit. After thorough washing, the vent was closed and the sample was transferred to a 12 cm-long×75 gm i.d. column with a pulled 5 μm tip packed with the same material. The chromatographic profile was from 100% solvent A (0.1% aqueous AcOH) to 50% solvent B (0.1% AcOH in $CH_3CN$) in 30 min at approximately 200 nL/min (manual split from 300 gL/min). Additional time was allotted for column washing and reequilibration. The LTQ was operated in automated mode using Xcalibur™ software. The acquisition method during MS/MS analysis involved one MS precursor ion scan followed by five data-dependent MS/MS scans. Higher order MS analyses involved an MS precursor scan followed by targeted MS$^4$ scans of those masses that specifically demonstrated loss of the ketone-biotin moeity and ketone-biotin-GlcNAc moiety in the MS/MS analysis. In the case of the OGT sample peptides, MS$^4$ data was used to search against an OGT sequence database using SEQUEST.(50) All potential peptide identifications were manually verified. In the case of the CREB sample, the acquisition method involved targeted MS/MS analysis of the presumptive ketone-biotin-GlcNAc modified peptide at m/z 1181.2, with simultaneous targeted MS$^3$ analysis of the GlcNAc modified peptide at m/z 1513.6 and MS$^4$ analysis of the unmodified peptide at m/z 1412.1.

The electrospray voltage was set at 1.6 kV and the heated capillary was set at 250° C. The ion selection window was set at 500-2000 m/z for all experiments. For MS/MS and higher order MS analyses, the relative collision energy for collision-induced dissociation (CID) was preset to 35% and a default charge state of +2 was selected to calculate the scan range for acquiring tandem MS spectra. The precursor ion isolation window was set at 3.5 for maximum sensitivity.

Figure 19:
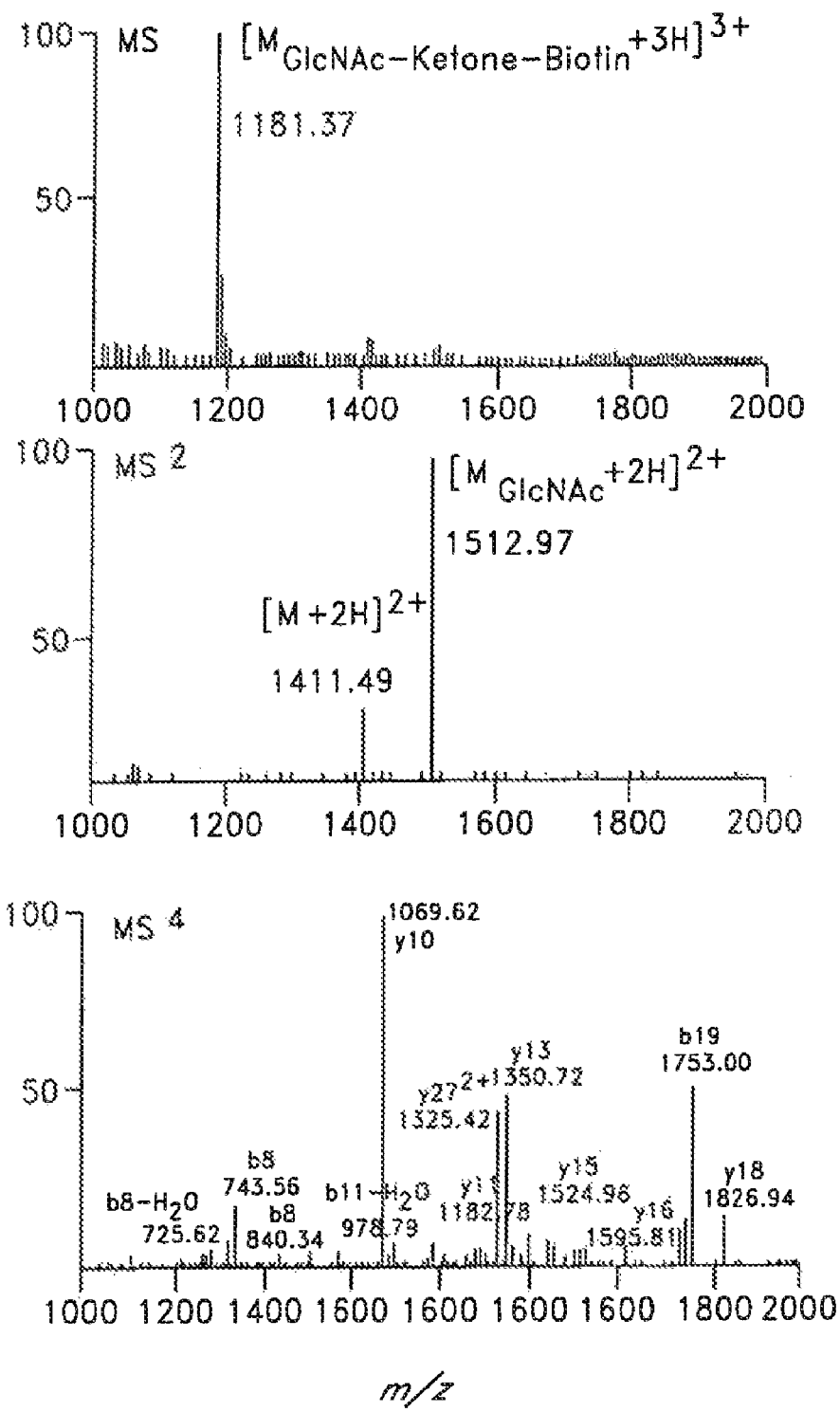
FIG. 19 shows identification of the O-GlcNAc modified peptide $^{256}$TAPTSTIAPGVVMASSPALPTQPAEEAAR$^{284}$ (SEQ ID NO.: 7) on CREB by LC-MS/MS.
Figure 21:
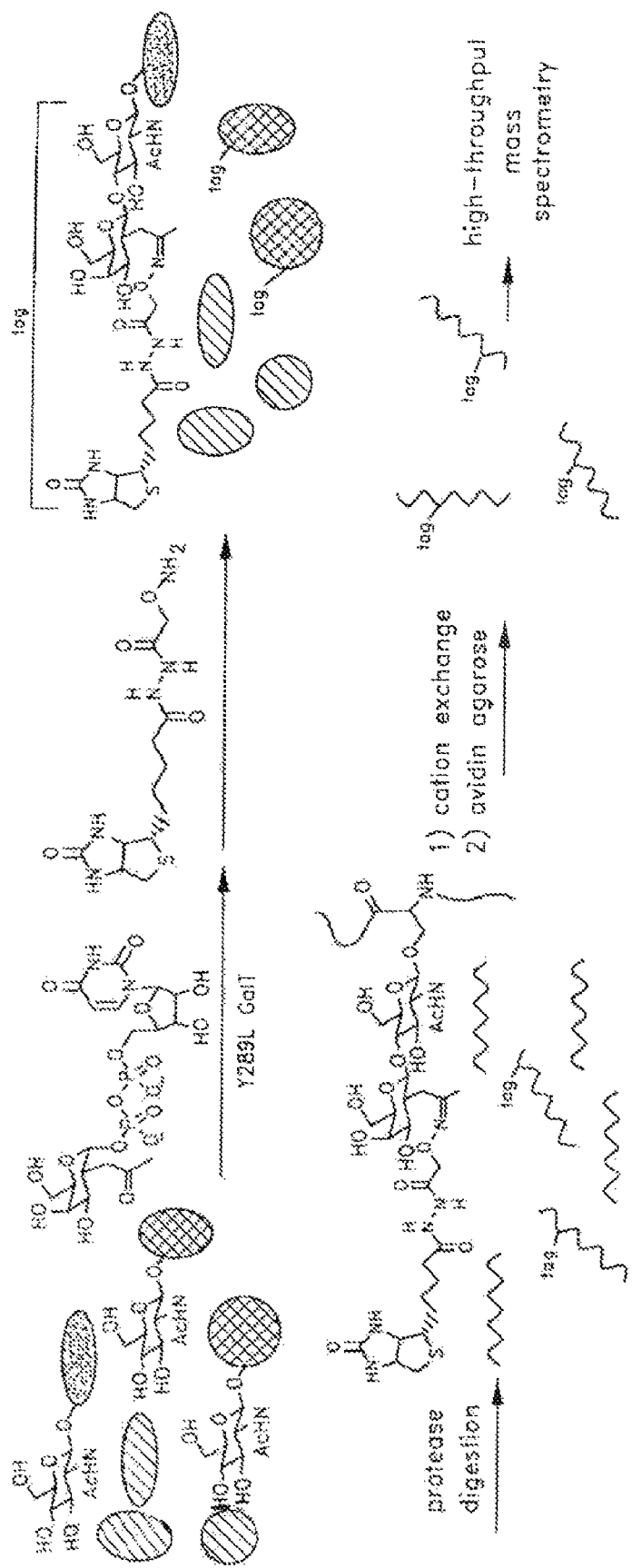
FIG. 21 shows a chemoselective strategy for identifying O-GlcNAc-glycosylated proteins from cellular lysates.

Avidin affinity capture of tryptic peptides from 250 ng of CREB protein identified the expected O-GlcNAc peptide $^{256}$TAPTSTIAPGVVMASSPALPTQPAEEAAR$^{284}$ (SEQ ID NO: 7).(47) FIG. 19 (see also FIG. 15A) shows the expected doubly charged ion labeled with the biotin-ketone moiety (m/z 1181.37). Upon tandem MS, loss of the ketone-biotin moiety (m/z 1512.97) as well as the ketone-biotin-GlcNAc moiety (m/z 1411.49) were observed. Targeted MS$^4$ analysis of the unmodified peptide yielded a number of y and b ions that verified the identification of this peptide.

FIG. 19 shows identification of the O-GlcNAc modified peptide on CREB by LCMS/MS. Tandem mass spectra of the labeled O-GlcNAc peptide $^{256}$TAPTSTIAPGVVMASSPAL-PTQPAEEAAR (SEQ ID NO: 7) (m/z 1181.37). CID revealed signature losses of the ketone-biotin moiety (m/z 1512.97) and the GlcNAc moiety (m/z 1411.49). Higher order MS analysis verified the identification of this peptide from the resultant y and b ions.

Experiments with avidin affinity captured OGT peptides identified a number of candidate O-GlcNAc peptides. Tandem MS of these peptides revealed characteristic charge losses corresponding to loss of the ketone-biotin moiety and ketone-biotin-GlcNAc moiety, which served to unambiguously identify the peptides as O-GlcNAc modified (FIG. 20).

FIG. 20A shows a peptide corresponding to the sequence $^{390}$ISPTFADAYSNMo$_x$GNTLK$^{406}$ (SEQ ID NO: 2) labeled with the ketone-biotin moiety (m/z=856.02). Upon tandem MS, loss of the ketone-biotin moiety (m/z 1025.00) followed by loss of the GlcNAc sugar (m/z 923.56) was observed. Similarly, FIG. 17B shows a peptide corresponding to the sequence $^{1037}$IKPVEVTESA$^{1046}$ (SEQ ID NO: 3) of OGT labeled with the ketone-biotin moiety (m/z 895.96). Upon tandem MS, loss of the ketone-biotin moiety (m/z 1275.03) followed by loss of the GlcNAc sugar (m/z 1072.03) was observed. Notably, three other peptides also displayed the characteristic loss signatures. Their masses, (m/z 1209.05), (m/z 946.20), and (m/z 769.56) corresponded to the labeled OGT peptides $^{407}$EMQDVQGALQCYTR$^{420}$ (SEQ ID NO: 9), $^{421}$AIQINPAFADHSNLASIHK$^{440}$ (SEQ ID NO: 10), and $^{826}$TIIVTTR$^{832}$ (SEQ ID NO: 11) (with an oxidized biotin moiety) respectively.

FIG. 20 shows identification of O-GlcNAc modifiediep-tides on OGT by LC-MS/MS. (A) Tandem mass spectra of the labeled O-GlcNAc peptide $^{390}$ISPTFADAYSN-MoxGNTLK$^{406}$ (SEQ ID NO: 2) (m/z 856.02). CID revealed signature losses of the ketone-biotin moiety (m/z 1025.00) and the GlcNAc moiety (m/z 923.56). Higher order MS analysis provided conclusive identification of this peptide from the resultant y and b ions. (B) Tandem mass spectra of the labeled O-GlcNAc peptide $^{1037}$ IKPVEVTESA$^{1046}$ (SEQ ID NO: 3) (m/z 895.96). CID revealed signature losses of the ketone-biotin moiety (m/z 1275.43) and the GlcNAc moiety (m/z 1072.43). Higher order MS analysis provided conclusive identification of this peptide from the resultant y and b ions as well as internal fragment ions.

To confirm the sequences of the modified peptides, we conducted targeted higher order mass spectrometry on the candidate species. As depicted in FIG. 20, the peptides corresponding to m/z 856.02 and m/z 895.96 were successfully sequenced by MS$^4$ analyses. Resultant y and b ions from the MS$^4$ spectra allowed identification of the peptides as $^{390}$ISPT-FADAYSNMo$_x$GNTLK$^{406}$ (SEQ ID NO: 2) and $^{1037}$IKPVEVTESA$^{1046}$ (SEQ ID NO: 3), respectively. Internal fragment ions in the MS⁴ spectrum of the latter helped to conclusively identify this peptide.

EXAMPLE 3

Exploring the O-GlcNAc Proteome: Direct Identification of O-GlcNAc-Modified Proteins from the Brain (97)

Protein PTMs represent an important mechanism for the regulation of cellular physiology and function. The covalent addition of chemical groups (e.g., phosphate, acetate, carbohydrate) extends the capabilities of proteins and provides a selective and temporal means of controlling protein function (51-53). Despite the importance of PTMs, their extent and significance are only beginning to be understood. O-GlcNAc glycosylation, the covalent attachment of β-N-acetylglucosamine to serine or threonine residues of proteins has been a subject of investigation (53-55). Unlike most carbohydrate modifications, O-GlcNAc is dynamic and intracellular and, as such, shares common features with protein phosphorylation (53, 54). Nearly 80 proteins bearing the O-GlcNAc group have been identified to date, including transcription factors, cytoskeletal proteins, protein kinases, and nuclear pore proteins (55). Recent studies have elucidated diverse roles for the O-GlcNAc modification, ranging from nutrient sensing to the regulation of proteasomal degradation and gene silencing (54,56). Moreover, perturbations in O-GlcNAc levels have been associated with disease states such as cancer, Alzheimer's and diabetes (54, 55).

Several lines of evidence suggest an important role for O-GlcNAc in the brain. First, activation of protein kinase A or C pathways leads to reduced levels of O-GlcNAc in certain protein fractions from cerebellar neurons (57), suggesting an intriguing, dynamic interplay between the two modifications in the brain. Second, O-GlcNAc transferase (OGT) is most abundant in the brain and pancreas (58). Although the regulation of OGT at the cellular level is not well understood, its activity appears to be modulated by several complex mechanisms involving various OGT isoforms, regulatory partners and regulation by PTMs (58). Finally, a role for O-GlcNAc in the brain is suggested by its presence on proteins important for neuronal function and pathogenesis such as cAMP-responsive binding protein (CREB)(59) and β-amyloid precursor protein (APP)(53, 54).

The O-GlcNAc modification has been definitively linked to only a handful of proteins from the brain (60). Efforts to identify proteins have been challenged by the difficulty of detecting the modification in vivo. Like many PTMs, O-GlcNAc is often dynamic, substoichiometric, and prevalent on low abundance regulatory proteins. The sugar is both enzymatically and chemically labile, being subject to reversal by cellular glycosidases and cleavage on the mass spectrometer. As with many protein kinases, the lack of a well-defined consensus sequence for OGT has precluded the determination of in vivo modification sites based on primary sequence alone.

Several methods have been reported for the identification of O-GlcNAc modified proteins. Proteins have been tritium labeled (61), enriched using antibodies or lectins (62, 63), or chemically tagged by metabolic labeling or BEMAD (β-Elimination followed by Michael Addition with Dithiothreitol)(62, 64). However, none of the existing methods is ideally suited to the direct, high-throughput identification of O-GlcNAc proteins from tissues or cell lysates. For instance, the tritium methodology is labor intensive and lacks sensitivity, necessitating purification of relatively large amounts of protein (62). Enrichment of O-GlcNAc proteins using antibody and lectin chromatography has not afforded direct observation of O-GlcNAc glycosylated peptides and thus cannot rule out false-positives (62). Although the BEMAD approach has been employed to map sites from purified proteins or protein complexes, it is an inherently destructive technique that requires extensive controls to establish whether a peptide contains a phosphate, O-GlcNAc or complex O-linked carbohydrate group (62).

The preferred embodiments permit investigations into the breadth of the modification and its potential functions across various tissues and species. Direct detection of the O-GlcNAc moiety would enable conclusive identification of the glycoproteins and localize the modification to specific functional domains, a prerequisite for understanding the physiological role of the modification. Moreover, the preferred embodiments are also useful for quantitative comparisons of glycosylation levels in cellular or disease states, such as cancer, Alzheimer's disease, neurodegeneration, cardiovascular disease, and diabetes.

The preferred embodiments can be applied to the direct, high-throughput analysis of O-GlcNAc proteins from the mammalian brain. Using the preferred embodiments, new O-GlcNAc modified proteins have been identified, including regulatory proteins associated with gene expression, neuronal signaling and synaptic plasticity. The diversity represented by this set of proteins provides new insight into the role of O-GlcNAc in neuronal function.

Numerous studies have demonstrated the importance of enrichment strategies for the detection of PTMs (71). In preferred embodiments, proteins from cellular lysates can be selectively labeled with the ketone-biotin handle, digested, and glycopeptides captured using avidin affinity chromatography. Mass spectrometric analysis of the enriched glycopeptides would afford the proteome-wide identification of novel glycosylated proteins. Importantly, the preferred embodiments would also permit the direct detection of modified peptides, enabling mapping of O-GlcNAc to specific functional domains within a protein.

Application of the Strategy to Bovine Alpha-Crystallin.

Figures 22A, 22B:
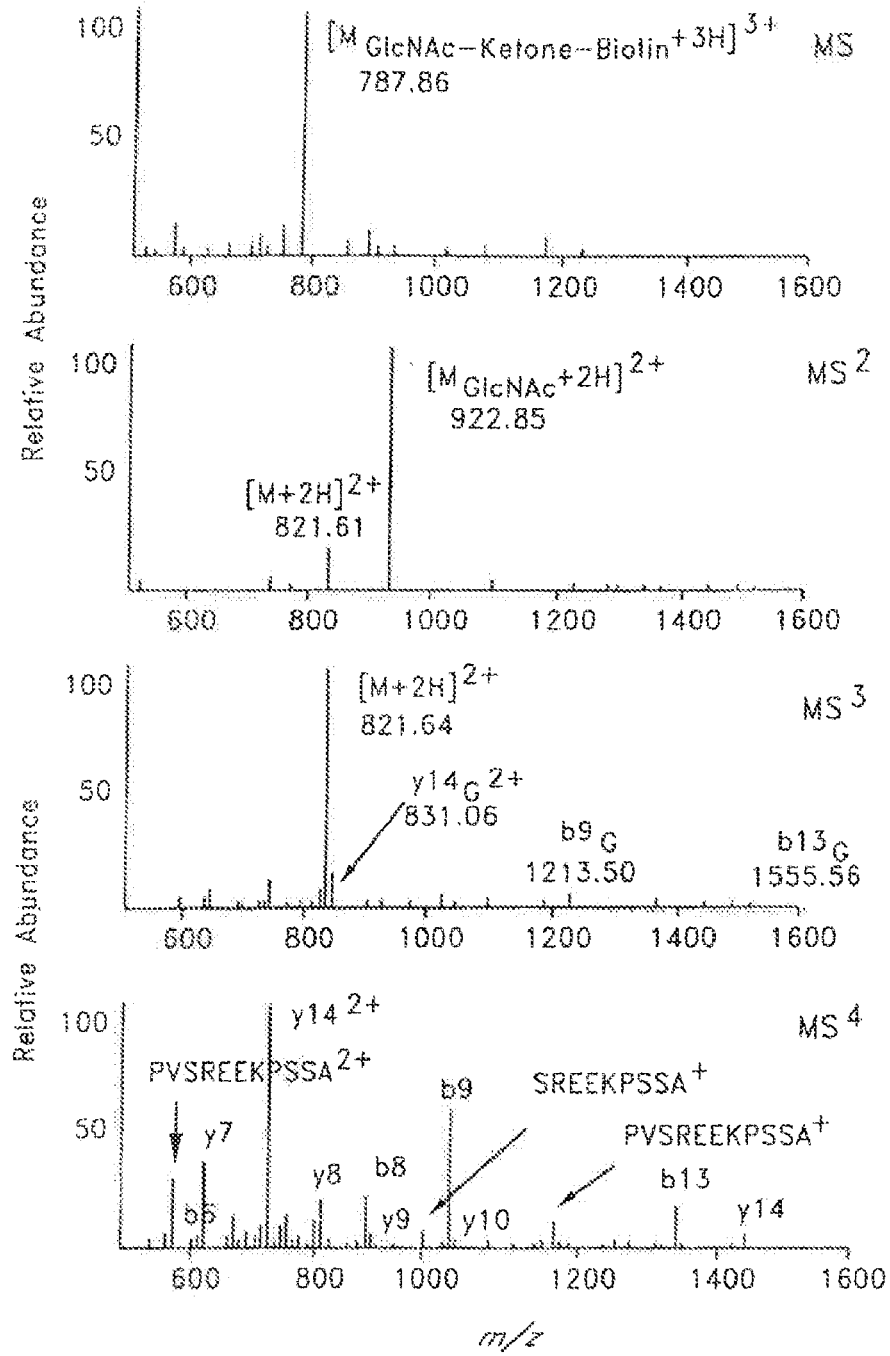
FIG. 22 shows (A) MS analysis revealing the tagged O-GlcNAc peptide $^{158}$AIPVSREEKPSSAPSS$^{173}$ (SEQ ID NO: 4) (m/z 787.86), and (B) summary of the y and b fragment ions observed.

O-GlcNAc modified peptides could be selectively enriched from peptide mixtures using α-A-crystallin. α-A-Crystallin contains one major site of glycosylation with an estimated stoichiometry of 10% (72). As such, the protein has proven to be a challenging target for MS analysis, requiring sophisticated Q-TOF instrumentation (72) or in-line lectin affinity chromatography (73). α-A-Crystallin was enzymatically labeled with the ketone functionality and chemically reacted with an aminooxy biotin derivative. Following tryptic digestion and avidin chromatography, enrichment of the expected glycosylated species was observed (FIG. 22). LC-MS analysis indicated a peak corresponding to the mass of the O-GlcNAc modified peptide $^{158}$AIPVSREEKPSSAPSS$^{173}$ (SEQ ID NO: 4) labeled with the ketone-biotin tag (m/z 1180.5). Sequence identification of the peptide was confirmed by tandem MS analysis. Notably, the ketone-biotin moiety produced a unique fragmentation pattern upon collision-induced dissociation (CID), which provided unambiguous indication of an O-GlcNAc containing peptide. Specifically, predominant loss of the ketone-biotin moiety (515.3 Da) was readily observed upon CID, followed by subsequent loss of the GlcNAc moiety (203.1 Da) during MS³ experiments. Higher order MS analysis localized the GlcNAc moiety on the peptide to the known site, Ser162(72).

Exploration of the O-GlcNAc Proteome of the Brain.

Having demonstrated the selective tagging and capture of O-GlcNAc glycosylated peptides, the preferred embodiments explored the O-GlcNAc proteome of the mammalian brain. Rat brain lysates were separated into nuclear and S100 cytoplasmic fractions, labeled with the tag, and digested with trypsin. A portion of the samples was subjected to proteolytic digestion with GluC to broaden the scope of analysis and generate confirmatory peptide sequences. Due to the overall complexity of the sample, the digested peptides were fractionated via strong cation exchange chromatography prior to avidin affinity chromatography.

Nearly 100 peptides containing the characteristic signature loss of the ketone-biotin tag were observed by LC-MS/MS. FIG. 23A shows an averaged ESI spectrum of ions eluting from the LC column with retention time 17.0 to 18.1 minutes. Peaks corresponding to peptides that displayed the diagnostic signature were subsequently selected for targeted $MS^4$ analysis for sequence identification. Notably, the vast majority of peaks in this region contained the GlcNAc-ketone-biotin moiety, demonstrating significant enrichment of this low-abundance modification. FIG. 23B shows the MS/MS spectrum of a representative peptide (m/z=789.2), indicating the characteristic loss of a ketone-biotin moiety (m/z=925.5) and GlcNAc-ketone-biotin moiety (m/z 823.9). Higher order MS analysis generated a definitive series of b and y ions (FIG. 23C), and database searching identified the peptide as belonging to the protein synaptopodin. Similarly, other MS techniques (72) can also be utilized to obtain sequencing information of species exhibiting the characteristic loss signature.

Using this approach, 34 unique peptides corresponding to 25 proteins from rat brain were sequenced (Table 1). Two of the proteins, microtubule-associated protein 2B (MAP2B) and host cell factor (HCF) have previously been reported to be O-GlcNAc glycosylated (74, 75), providing strong validation of the preferred embodiments. In addition, the preferred embodiments can be confirmed by earlier reports by establishing distinct amino acid stretches within each protein that bear the modification. Two sites of glycosylation were identified in the N-terminal region of MAP2B. In accordance with a demonstrated interaction between the N-terminal region of HCF and both wheat germ agglutinin lectin and an anti-O-GlcNAc antibody (75), four distinct sites within three peptides in the N-terminal region of HCF were observed. Finally, erythrocyte protein band 4.1-like 3 was identified as modified in a region that shares significant sequence identity to a reported glycopeptide from human erythrocyte membrane protein band 4.1 ($^{1029}$TITSETTSTTTTTHITK$^{1045}$ (SEQ ID NO: 12) and $^{773}$(TAQ)TITSETPSSTTTTQITK$^{791}$ (SEQ ID NO: 13), respectively)(76).

TABLE 1

O-GlcNAc glycosylated proteins from the mammalian brain

| Protein | NCBI entry | Function | Peptide sequence | Residues |
|---|---|---|---|---|
| Transcriptional regulation Sox2 (sry-related high mobility group box 2) | 31543759* | Transcription factor | SEASSSPPVVTSSHSR (SEQ ID NO: 14) | 248-264 |
| ATF-2 | 13591926 | Transcription factor, histone acetyltransferase | AALTQQHPPVTDGTVK (SEQ ID NO: 15) | 262-278 |
| HCF | 34881756 | Transcription regulator, chromatin associated factor | TAAAQVGTSVSSAANTSTRPII TVHK† (SEQ ID NO: 16) | 620-645 |
| HCF | 34881756 | Transcription regulator, chromatin associated factor | VMSVVQTK (SEQ ID NO: 17) SPITIITTK (SEQ ID NO: 18) | 691-698 802-810 |
| SRC-1 (steroid receptor coactivator 1) | 34863079 | Transcription coactivator for nuclear receptors | INPSVNPGISPAHGVTR (SEQ ID NO: 19) | 188-204 |
| CCR4-NOT4 | 34855140 | Global transcriptional regulator, mRNA metabolism | SNPVPISSSNHSAR (SEQ ID NO: 20) | 329-343 |
| CCR4-NOT subunit 2 | 34864872 | Global transcriptional regulator, Mrna metabolism | SLSQGTQLPSHVYPTTGVPTM SLHTPPSPSR (SEQ ID NO: 21) | 79-109 |
| TLE-4 (transducin-like enhancer protein 4) | 9507191 | Transcriptional corepressor | TDAPTPGSNSTPGLRPVPGKPP GVDPLASSLR (SEQ ID NO: 22) | 298-329 |

TABLE 1-continued

O-GlcNAc glycosylated proteins from the mammalian brain

| Protein | NCBI entry | Function | Peptide sequence | Residues |
|---|---|---|---|---|
| RNA-binding motif protein 14 | 16307494* | Transcriptional coregulator for steroid receptors | AQPSVSLGAAYR (SEQ ID NO: 23) | 239-250 |
| Nucleic acid-binding proteins NFR-xB (nuclear factor-related xB) | 34862978 | DNA binding protein | VPVTATQTK (SEQ ID NO: 24) | 896-904 |
| Zinc finger RNA-binding protein | 34854400 | RNA binding protein | AGYSQGATQTQAQQAR (SEQ ID NO: 25) | 58-74 |
| Intracellular transport Hrb (HIV-1 Rev-binding protein) | 34859394 | RNA trafficking | APVGSVVSVPSHSSASSDKS (SEQ ID NO: 26) | 360-378 |
| GRASP55 (Golgi reassembly stacking protein 2) | 20301956 | Membrane protein transport, Golgi cisternae stacking | VPTTVEDR (SEQ ID NO: 27) | 423-430 |
| Cellular organization/dynamics CErythrocyte protein band 4.1-like 3 | 16758808 | Cytoskeletal protein | TITSETTSTTTTTHITK (SEQ ID NO: 28) | 1026-1042 |
| | | | TTSTTTTTHITKTVGGISE (SEQ ID NO: 29) | 1031-1050 |
| Erythocyte protein band 4, 1-like 1, isoform L | 11067407 | Cytoskeletal protein | DVLTSYGATAETLSTSTTTHV TK (SEQ ID NO: 30) | 1460-1483 |
| Erythocyte protein band 4, 1-like 1, isoform L | 11067407 | Cytoskeletal protein | TLSTSTTTHVTKTVKGGFSE (SEQ ID NO: 31) | 1472-1491 |
| Spectrin beta chain (fodrin beta chain) | 34879632 | Axonal/pre-synaptic cytoskeletal protein | HDTSASTQSTPASSR (SEQ ID NO: 32) | 2354-2368 |
| MAP18 | 19856246 | Axonogenesis | TTKTTRSPDTSAYCYE (SEQ ID NO: 33) | 2018-2034 |
| MAP28 | 111965 | Dynamic assembly of microtubules at dendrites | SSKDEEPQKDKADVADVPV SE (SEQ ID NO: 34) | 366-387 |
| MAP28 | 111965 | Dynamic assembly of microtubules at dendrites | KADKVADVPSE (SEQ ID NO: 35) | 376-387 |
| | | | TSSESPFPAKE (SEQ ID NO: 36) | 788-798 |
| Cellular communication/signal transduction | 16758634 | Signal transduction, | DGTEVHVTASSSGAGVVK (SEQ ID NO: 37) | 1584-1601 |
| WNK-1 (lysine deficient protein kinase) | | Ion homeostasis | MGGSTPISAASATSLGHFTK (SEQ ID NO: 38) | 2043-2062 |

TABLE 1-continued

O-GlcNAc glycosylated proteins from the mammalian brain

| Protein | NCBI entry | Function | Peptide sequence | Residues |
|---|---|---|---|---|
| PDZ-GEF | 34857578 | Guanine nucleotide exchange factor for RAP 1/2 | ISSRSSIVSNSSFDSVPVSLHDE (SEQ ID NO: 39) | 1211-1233 |
| PDZ-GEF | 34857578 | Guanine nucleotide exchange factor for RAP 1/2 | SSFDSVPVSLHDER (SEQ ID NO: 40) SVPVSLHDE (SEQ ID NO: 41) | 1221-1234 1225-1233 |
| Synaptopodin | 11067429 | Dendritic spine formation | VSGHAAVTTPTKVYSE (SEQ ID NO: 42) | 203-218 |
| Bassoon | 9506427 | Synaptic veside cycling | VTQHFAK$ (SEQ ID NO: 43) | 1338-1444 |
| Uncharacterized proteins Hypothetical protein FLI31657 | 34855501 | Unknown | IGGDLTAAVTK (SEQ ID NO: 44) | 196-206 |
| 1300019H17RIK EN protein | 34880180 | Unknown | EAALPSTK (SEQ ID NO: 45) | 286-293 |
| KIAA1007 protein | 34851212 | Unknown | TVTVTKPTGVSFK (SEQ ID NO: 46) | 1051-1063 |
| DACA-1 homolog | 34861007 | Unknown | IGDVTTSAVK (SEQ ID NO: 47) | 271-280 |

*Mouse proteins identified in the National Center for Biotechnology Information (NCBI) database. Corresponding rat orthologs were identified in the Celera database.
†We identified two district sites of O-GlcNAc glycosylation on this peptide.
$The site of modification was localized to Ser-372 or Ser-373 by using a combination of chemoenzymatic tagging and β-elimination.
§Confirmed by peptide synthesis and MS sequencing analysis (see FIG. 30)

In addition to known proteins, the preferred embodiments enabled the identification of 23 novel O-GlcNAc glycosylated proteins from the mammalian brain (Table 1). The proteins fall into a broad range of functional classes (77), including those involved in transcriptional regulation, neuronal signaling, and synaptic plasticity. Consistent with studies demonstrating that O-GlcNAc modifies transcription factors and RNA polymerase II, a large number of proteins involved in transcription was identified. In addition to transcription factors, O-GlcNAc was found on novel classes of transcriptional proteins such as coactivators, corepressors and chromatin remodeling enzymes, which suggest expanded roles for O-GlcNAc in transcriptional control.

The preferred embodiments afforded the simultaneous detection of multiple PTMs. For instance, an O-GlcNAc modified peptide with a characteristic loss of 98 Da upon CID, consistent with phosphorylation within the same peptide was observed. Moreover, two O-GlcNAc modifications were identified within the N-terminal domain of HCF.

Merging the Technology with β-Elimination Strategies to Map Glycosylation Sites.

Figure 24C:
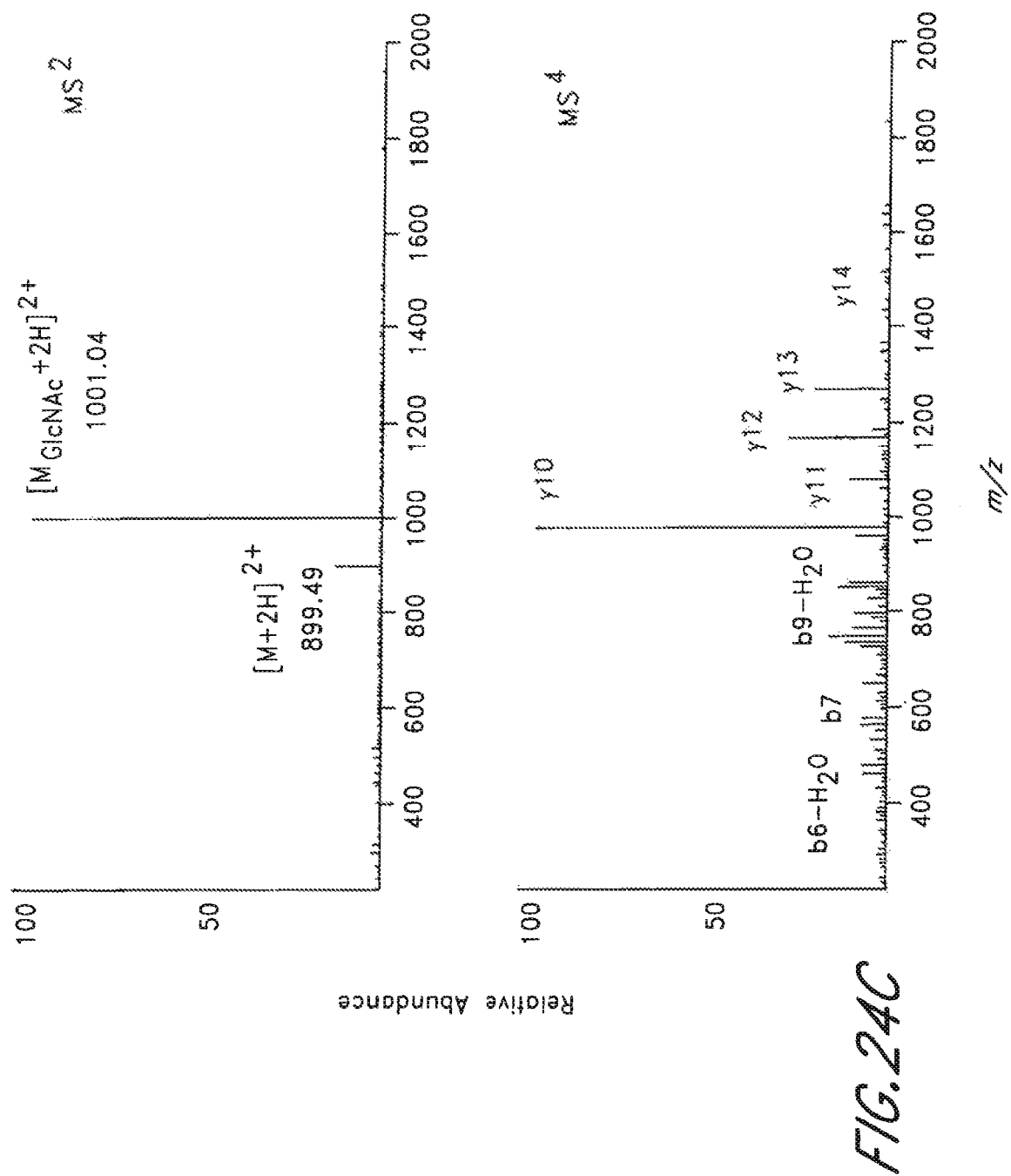
FIG. 24 shows (A) strategy for the formation of a stable sulfide adduct from tagged O-GlcNAc peptides, (B) MS/MS analysis of the sulfide adduct of peptide $^{360}$APVGSVVSVP-SHSSASSDK$^{378}$ (SEQ ID NO: 6) from HIV-1 Rev binding protein, (C) MS/MS spectrum of the corresponding peptide prior to β-elimination shows the characteristic ketone-biotin signature, indicating that the original peptide was O-GlcNAc glycosylated, and (D) summary of the prominent b and y ions from MS/MS analysis of the β-eliminated peptide.
Figure 25:
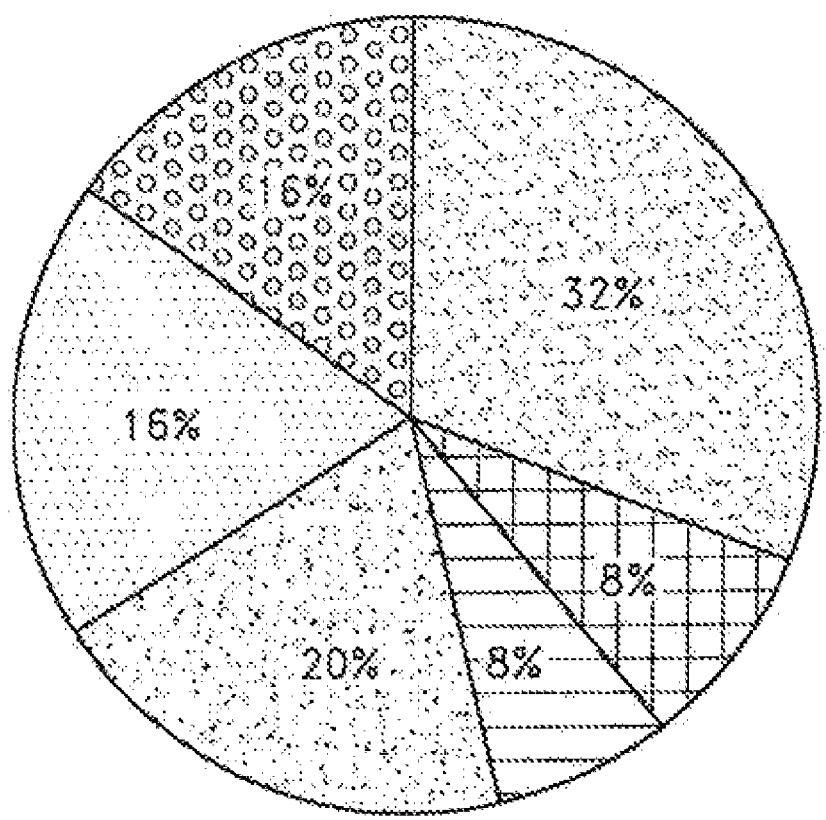
FIG. 25 shows functional classification of the identified O-GlcNAc proteins according to categories described by Schoof et al.(1)

The mapping of specific O-GlcNAc glycosylation sites is inherently difficult due to the lability of the glycosidic linkage upon CID and the preference of OGT for sequences rich in serine, threonine and proline residues. Although the sites of O-GlcNAc glycosylation to short amino acid sequences were narrowed, the features noted above limited the ability to do site-mapping on all but a few sequences. To address this issue, the possibility of using precedented β-elimination strategies in conjunction with the preferred embodiments to localize specific modification sites was examined. Previous studies have shown that glycosylated and phosphorylated serine/threonine residues as well as carboxyamido-modified cysteine residues undergo β-elimination to form dehydroalanine/β-methyldehydroalanine under strong alkaline conditions (62, 78). Subsequent Michael addition of a thiol nucleophile generates a stable sulfide adduct. S100 cytoplasmic lysates were labeled with a ketone-biotin tag and enriched the O-GlcNAc glycopeptides using avidin affinity chromatography as described. One of the enriched fractions was then selected for β-elimination, followed by butanethiol addition (FIG. 24). Tandem MS analysis of the resultant peptides permitted localization of the glycosylation site on HIV-1 Rev binding protein from seven possible residues to Ser372 or Ser373. Notably, tandem MS analysis prior to β-elimination conclusively demonstrated that the original peptide was O-GlcNAc glycosylated, rather than phosphorylated or modified with a complex carbohydrate. With further refinement of the β-elimination methodology toward complex mixtures, the combined ketone-labeling and β-elimination approaches are thought to be a powerful tool for mapping specific O-GlcNAc modification sites.

The preferred embodiments allow for the first direct, high-throughput analysis of O-GlcNAc glycosylated proteins from the mammalian brain. The proteins were identified using a chemoenzymatic approach that exploits an engineered galactosyltransferase enzyme to selectively label O-GlcNAc proteins with a ketone-biotin tag. The tag provides both a straightforward means to enrich low abundance O-GlcNAc peptides from complex mixtures, and a unique signature upon tandem MS for unambiguous identification of the O-GlcNAc glycosylated species. In contrast to reported antibody or lectin-based methods (62, 63), the strategy provides direct evidence of O-GlcNAc glycosylation and permits mapping of modification sites to short amino acid sequences. The ability to localize O-GlcNAc is essential to survey its distribution across the proteome as well as understand its functional significance on a given protein or family of proteins.

A feature of the preferred embodiments is the potential to explore the interplay among post-translational modifications (PTMs). In this study, two peptides that contained more than one PTM were identified. For instance, the N-terminal domain of HCF showed two O-GlcNAc moieties within the same peptide, and a second peptide exhibited evidence of both phosphorylation and glycosylation. Notably, all O-GlcNAc proteins known to date are phosphoproteins, and increasing evidence suggests that glycosylation functionally antagonizes phosphorylation in many cases (54, 59). The preferred embodiments involve a non-destructive technique that does not require the removal of other PTMs in order to study O-GlcNAc. As such, the preferred embodiments permit a direct examination of whether specific glycosylation and phosphorylation events are mutually exclusive in vivo, as suggested for the C-terminal domain of RNA polymerase II (79), or whether the two modifications co-exist, as recently reported for the transcription factor signal transducer and activator of transcription 5 (Stat5)(80).

The preferred embodiments can also be combined with existing β-elimination strategies to identify specific sites of glycosylation. Mapping of sites by MS has proven challenging due to the lability of the sugar moiety and the preponderance of serine, threonine and proline residues in O-GlcNAc peptides. By exploiting β-elimination methods in combination with the preferred embodiments, the glycosylation site on HIV-1 Rev binding protein was localized from seven possible residues to Ser372 or Ser373. The preferred embodiments can be a powerful tool for mapping O-GlcNAc glycosylation sites on other proteins in vivo.

The preferred embodiments identified 25 O-GlcNAc glycosylated proteins from the mammalian brain. Over the last 20 years, the O-GlcNAc pendant moiety has been established on approximately 80 proteins (55). Thus, these results represent a significant expansion in the number of known O-GlcNAc proteins, and they provide new insights into the breadth of the modification and its potential functions in the brain.

Consistent with previous studies demonstrating an important role for O-GlcNAc in transcriptional regulation, two novel transcription factors, sex determining factor Y box (SOX2) and activating transcription factor-2 (ATF-2), were identified. SOX2 is a member of the high mobility group (HMG) box superfamily of minor groove DNA-binding proteins (81), proteins believed to govern cell fate decisions during diverse developmental processes. Although primarily known for its role in embryogenesis, SOX2 has also been detected in the adult central nervous system (82). ATF-2 is a DNA-binding transcription factor that is ubiquitous but enriched in the brain (83). It also possesses an intrinsic histone acetyltransferase (HAT) activity that is required for activating transcription (84). ATF-2 functions as both a homodimer and heterodimer with c-Jun and is responsive to c-Jun N-terminal kinase and p38 mitogen activated protein (MAP) kinase pathways (83). Interestingly, the transcription factor appears to play multiple roles in glucose homeostasis. For instance, ATF-2 has been shown to up-regulate transcription from the insulin promoter in human pancreatic β-cells in a $Ca^{2+}$/calmodulin-dependent protein kinase IV (CaMKIV)-dependent manner (85). Moreover, recent studies indicate that ATF-2 activates the gluconeogenic gene phosphoenolpyruvate carboxykinase (PEPCK) in HepG2 hepatic cells upon retinoic acid induction (86). As O-GlcNAc has been implicated in nutrient sensing and the development of insulin-resistant diabetes (53-55), the finding that ATF-2 is glycosylated provides an exciting link for further investigation. Notably, the region of glycosylation lies in a proline-rich stretch near a motif essential for the HAT activity of ATF-2. Phosphorylation in the N-terminal transactivation domain of ATF-2 (Thr 69, Thr 71) up-regulates its HAT activity (84). It will be important to examine in this instance whether glycosylation and phosphorylation act in opposition.

While transcription factors and RNA polymerase II have been shown to be glycosylated, other important elements of the transcriptional machinery have not been well documented. O-GlcNAc on novel classes of transcriptional proteins, including coactivators, corepressors and chromatin remodeling enzymes was shown. This finding suggests broader roles for O-GlcNAc in regulating transcription than previously recognized. For instance, the modification on two proteins (including a ubiquitin ligase) in the carbon catabolite repression 4-negative on TATA-less (CCR4-NOT), a large protein complex involved in mRNA metabolism and the global control of gene expression was found (87). In addition, O-GlcNAc was identified on steroid receptor coactivator-1 (SRC-1), a chromatin remodeling protein that functions as a transcriptional coactivator for estrogen, thyroid, and other nuclear receptors (88). Finally, O-GlcNAc was found on HCF, a chromatin-associated factor that interacts with both OGT and the Sin3A histone deacetylase (HDAC) complex in vivo (75). Studies have shown that Sin3A effects transcriptional repression by recruiting HDACs and reorganizing chromatin structure. Moreover, mammalian Sin3A has been shown to interact with OGT and thereby synergistically repress transcription from both basal and Sp-1 driven promoters (89). Four distinct sites of glycosylation within the N-terminal domain of HCF, a region required for its interaction with both OGT and Sin3A, was identified. Moreover, three of those sites are located within a short basic region of HCF determined to bind specifically to Sin3A in a yeast two-hybrid screen (amino acids 610-722)(75). It is also contemplated that the functional impact of HCF glycosylation on its interaction with Sin3A and OGT, and on gene silencing be examined.

The preferred embodiments demonstrate that a number of proteins involved in neuronal signaling and synaptic function are the targets of O-GlcNAc glycosylation. For instance, the modification on PDZ-GEF, a guanine nucleotide exchange factor that activates the Ras-related GTPases Rap1 and Rap2 was identified (90). PDZ-GEF contains a PDZ domain, a protein-interacting module often involved in the assembly of signal transduction complexes at the synapse (91). Another O-GlcNAc protein is WNK-1 (With No Lysine K), a serine/threonine protein kinase whose activation has been linked to ion transport and hypertension (92). Moreover, two brain-enriched proteins important for synaptic function, synaptopodin and bassoon was identified. The actin-associated protein synaptopodin is essential for dendritic spine formation, with synaptopodin-deficient mice exhibiting a lack of spine apparatuses as well as impaired long-term potentiation and spatial learning (93). Bassoon, a scaffolding protein of the cytomatrix assembled at the active zone (CAZ) plays a critical role in synaptic vesicle cycling (94). Taken together, these findings reveal that O-GlcNAc glycosylation likely plays critical roles in neuronal communication and synaptic function.

A chemoenzymatic strategy for the high-throughput identification of O-GlcNAc glycosylated proteins from the mammalian brain was demonstrated. The preferred embodiments permit the enrichment and direct identification of O-GlcNAc glycosylated peptides from complex mixtures and can be combined with existing technologies to map specific glycosylation sites. The preferred embodiments enable explorations of the O-GlcNAc proteome in any cell type, tissue or subcellular fraction of interest. Moreover, studies of the dynamic interplay among PTMs and future extension of the methodology to quantitative proteomics should be possible. Using the approach, 23 new O-GlcNAc glycosylated proteins from the brain, including regulatory proteins associated with gene expression, neuronal signaling and synaptic plasticity, were discovered. The functional diversity represented by this set of proteins suggests an expanded role for O-GlcNAc in regulating neuronal function. Accordingly, the preferred embodiments can be used for detection of certain disease states associated with neuronal function, such as cancer, Alzheimer's disease, and neurodegeneration.

Materials and Methods

Chemoenzymatic Labeling, Biotinylation and Avidin Enrichment of α-Crystallin.

Bovine lens α-crystallin (8.7 μg, Sigma-Aldrich) was incubated with the unnatural UDP substrate (65) (750 μM), and Y289L GalT (66) in 20 mM HEPES pH 7.9 containing 5 mM $MnCl_2$ and 100 mM NaCl for 12 h at 4° C. The reactions were then diluted 2-fold with saturated urea, 2.7 M NaOAc pH 3.9 (50 mM final concentration, pH 4.8) and N-(aminoxyacetyl)-N'-(D-biotinoyl) hydrazine (5 mM final concentration, Dojindo), and incubated with gentle shaking for 20-24 h at 23° C. The tagged α-A-crystallin was excised from a Coomassie-stained gel and digested with trypsin (Promega) essentially as described by Shevchenko et al (67). Avidin affinity chromatography and LC-MS/MS analysis were performed as described below.

Preparation of Rat Forebrain Extracts.

The forebrains of Sprague Dawley rats (Charles River Laboratories) were dissected on ice, lysed into 10 volumes of homogenization buffer, and fractionated into nuclear and S100 cytoplasmic components as described by Dignam et al.(68), except that protease inhibitors, phosphatase inhibitors, and a hexosaminidase inhibitor (50 mM GlcNAc) were added to the buffers. Prior to labeling, the extracts were dialyzed into 20 mM HEPES pH 7.3, 0.1 M KCl, 0.2 mM EDTA, 0.2% Triton X-100, 10% glycerol.

Chemoenzymatic Labeling of Cellular Extracts.

Extract (1-10 mg; 1-3 mg/mL) was incubated with 5 mM $MnCl_2$, 1.25 mM ADP, 0.5 mM unnatural UDP substrate, and Y289L GalT (25 ng/μL) for 12-14 h at 4° C. Following enzymatic labeling, extracts were dialyzed into denaturing buffer (5 M urea, 50 mM $NH_4HCO_3$ pH 7.8, 100 mM NaCl; 3×2 h). The pH was adjusted with 2.7 M NaOAc pH 3.9 (final concentration 50 mM, pH 4.8). Aminoxy biotin (2.75 mM) was added, and the reactions were incubated as described for α-A-crystallin. Extracts were diluted with 3 M $NH_4HCO_3$ pH 9.6 (50 mM final concentration, pH 8) and dialyzed (1×2 h, 1×10 h) into 6 M urea, 50 mM $NH_4HCO_3$ pH 7.8, 100 mM NaCl, followed by either denaturing (4 M urea, 50 mM $NH_4HCO_3$ pH 7.8, 10 mM NaCl) or non-denaturing buffer (50 mM $NH_4HCO_3$ pH 7.8, 10 mM NaCl).

Proteolytic Digestion and Cation Exchange/Avidin Affinity Chromatography.

Non-denatured extracts from the previous step were concentrated and denatured/reduced as described in the ICAT protocol from Applied Biosystems. Proteins were then alkylated with 15 mM iodoacetamide for 45 min in the dark, diluted to 0.04% SDS with 50 mM $NH_4HCO_3$ pH 7.8, and digested with trypsin or GluC (20-30 ng/μL) for 12-14 h at 37° C. Urea-denatured extracts were diluted with 50 mM $NH_4HCO_3$ pH 7.8 following the reduction (10 min) and alkylation steps, and subjected to protease digestion as described above.

Proteolytic digests conducted in the presence of urea were desalted with peptide macrotrap cartridges (Michrom Bioresources). Digests conducted without urea were acidified with 1% aqueous TFA and diluted into cation exchange load buffer (Applied Biosystems). Cation exchange chromatography was performed on 1-3 mg of lysate as described by the manufacturer, except that peptides were eluted with a step gradient of 40 mM, 100 mM, 200 mM, and 350 mM KCl in 5 mM $KH_2PO_4$ containing 25% $CH_3CN$. Fractionated peptides were enriched via avidin affinity chromatography (Applied Biosystems) as described by the manufacturer except that the washes were tripled in volume.

β-Elimination of Avidin-Purified Peptides.

Following avidin chromatography, a portion of the S100 lysate fraction (40 mM KCl elution) was subjected to β-elimination (62) using 25 mM butanethiol, and reactions were stopped with AcOH.

LC-MS Analysis of Avidin-Enriched Biotinylated Peptides.

Automated nanoscale reversed-phase HPLC/ESI/MS was performed using an HPLC pump, autosampler (Agilent Technologies), and linear ion trap mass spectrometer (Thermo-Electron) with a variation of the "vented column" approach described by Licklider et al (69). For data dependent experiments, the mass spectrometer was programmed to record a full-scan ESI mass spectrum (m/z 500-2000) followed by five data-dependent MS/MS scans (relative collision energy=35%; 3.5 Da isolation window). Precursor ion masses for candidate peptides were identified by inspecting product ion spectra for peaks corresponding to losses of the ketone-biotin and ketone-biotin-GlcNAc moieties. Up to eight candidate peptides at a time were analyzed in subsequent targeted $MS^4$ experiments to derive sequence information. For all MS experiments, the electrospray voltage was set at 1.6 kV and the heated capillary was maintained at 250° C.

Database Analysis to Identify O-GlcNAc Proteins.

MS/MS or $MS^4$ data were matched to amino acid sequences in the NCBI rat/mouse protein database using the SEQUEST algorithm (70).

EXAMPLE 4

Protocol for O-GlcNAc Protein Capture

A general protocol for O-GlcNAc protein capture is provided.

Part A. Ketone/Aminooxy Biotin Labeling
Lysate Dilution Buffer
Depending on the volume and composition of cell lysate, adjust the composition and concentration of dilution buffer, so the final concentration in the ketone probe reaction is:

Hepes: 20 mM, pH7.9
NaCl: 50 mM
NP-40: 0.9%
DTT: 2.5 mM
Protease inhibitors: 1×

Prepare denatured cell extract by boiling cells in lysis buffer (20 mM HEPES pH 7.9, 0.5% SDS, 10 mM DTT)

Mix the following (200 µL final volume—note, the volume is not critical, but the final concentrations of HEPES should be 10-20 mM, 5 mM $MnCl_2$, 1.25 mM ADP, 500 uM ketone, 20 ng/ul-40 ng/ul Y289L GalT, PNGaseF scaled appropriately to volume):

| Volume | Description | Sample I | II | III | Note |
|---|---|---|---|---|---|
| x µL | Denatured cell extract | + | + | + | 100-300 ug for transfected lysates, >500 ug otherwise |
| (165-x) µL | Lysate dilution buffer | + | + | + | |
| 10 µL | 100 mM $MnCl_2$ | + | + | + | Cofactor for GalT |
| 10 µL | 25 mM 5'-ADP | + | + | + | |
| 4 µL | 1 mg/mL Y289L GalT | + | $H_2O$ | + | |
| 1 µL | PNGaseF | + | + | + | New England Biolabs |
| 6.4 µg | Ketone sugar probe (add to 0.5 mM) | + | + | − | Dry 10 µL of 10 mM solution (1 mg ketone in 156 µL water) |

Rotate at 4° C. for 12-16 h.

Dialyze supernatant into urea buffer (5 M urea, 8 mM HEPES pH 7.9, 100 mM NaCl) for 3×2~3 h at 4° C. to remove excess ketone sugar.

Add 22 µL of detergent solution (9.1% NP-40, 0.9% SDS). Mix samples for 5 min.

Slowly add 1.6 µL of acetate solution (0.3M NaOAc, 3M AcOH). The final pH of the samples becomes 4.75-4.9. Alternatively, add X µL of a pH 3.9 2.5M NaOAc solution such that the final concentration of NaOAc is 50 mM Importantly: the low pH is necessary for catalyzing the coupling between ketone and aminooxy groups. Salt and detergents help solubilize proteins at lower pH. Always check the final pH with pH strips before continuing.

Bring samples back to room temperature and mix for 10 min. Centrifuge at 20,000×g for 5 min, save supernatant.

Add 20 µL of 30 mM aminooxy biotin solution to a final concentration of 3 mM, and mix at room temperature for 20-24 h on shaker.

Neutralize each sample by adding 5 µL of 1M HEPES pH 7.9, and mix for 10 min.

Centrifuge at 21,500×g for 5 min, save supernatant.

Dialyze supernatants into urea buffer (6 M urea, 10 mM HEPES pH 7.9, 100 mM NaCl) for 4 h, 12 h and 4 h at room temperature in dialysis tubing. Dilute the sample with the urea buffer if the sample volume is too small. The use of dialysis tubing is essential for the removal of excess aminooxy biotin.

Dialyze samples into saline buffer (10 mM HEPES pH 7.9, 100 mM NaCl, 1 mM DTT) for 2×4 h at 4° C.

Centrifuge at 21,500×g for 5 min, and save supernatant. Supplement with protease inhibitors.

These biotinylated cell lysates will be used for Part B.

Part B. Streptavidin-Agarose Affinity Capture

Low Salt Wash Buffer

| | For 50 mL | Stock Concentration |
|---|---|---|
| 0.1M $Na_2HPO_4$ pH 7.5 | 10 mL | 0.5M |
| 0.15M NaCl | 1.5 mL | 5M |
| 1% Triton-X100 | 2.5 mL | 20% |
| 0.5% Sodium Deoxycholate | 2.5 mL | 10% |
| 0.1% SDS | 0.5 mL | 10% |

High Salt Wash Buffer

| | For 50 mL | Stock Concentration |
|---|---|---|
| 0.1M $Na_2HPO_4$ pH 7.5 | 10 mL | 0.5M |
| 0.5M NaCl | 5 mL | 5M |
| 0.2% Triton-X100 | 0.5 mL | 20% |

Elution Buffer

| | For 10 mL | Stock Concentration |
|---|---|---|
| 50 mM Tris 6.8 | 1 mL | 0.5M |
| 2.5% SDS | 2.5 mL | 10% |
| 100 mM DTT | 1 mL | 1M |
| 10% Glycerol | 2 mL | 50% |
| 2 mM Biotin | 4.9 mg | Solid |

Wash 3 aliquots of 60-100 µL of sepharose 6B beads (Sigma) with 1 mL low salt wash buffer three times.

Wash 3 aliquots of 60-100 µL of streptavidin-agarose beads (Pierce) with 1 mL low salt wash buffer three times.

Pre-clear each sample of biotinylated lysates with 60-100 µL of sepharose for 1 h at 4° C. with constant rotation. Save some of the pre-clear (the equivalent of ~5 µg of protein) for the 'input sample' on the streptavidin-HRP Western.

Centrifuge at 2,000×g for 30 sec. Collect the supernatant and incubate with 60-100 µL of streptavidin-agarose for 2 h at 4° C. with constant rotation. Centrifuge at 2,000×g for 30 sec. Collect the beads. Remove the flow-through and save at least ~5 ug of protein for 'flow-through sample' on the streptavidin-HRP Western.

Wash three times with 1 mL cold low salt wash buffer, and three times with 1 mL cold high salt wash buffer. During each wash, rotate the microcentrifuge tube for 5 min at 4° C. After each wash, pellet the beads by centrifugation at 2,000×g for 30 s and discard supernatant.

To each aliquot of beads add 2× volume of elution buffer. Vortex the sample briefly and boil for 5 min. Remove from heat, vortex again and boil for another 5 min Centrifuge at 2000×g for 1 min, and collect the supernatant as eluted material.

To examine if the capture of biotinylated proteins is successful, analyze eluted materials by Western blotting with horseradish peroxidase (HRP)-conjugated streptavidin. The gel intended for stretpavidin-HRP should contain the following samples: ~5 µg input from the +GalT/+ket, +GalT/−Ket, −GalT/+ket; ~5 µg flow-through +GalT/+ket, +GalT/−Ket, −GalT/+ket, and 5 µg eluent +GalT/+ket, +GalT/−Ket, −GalT/+ket. The remainder of the eluent may be used (in whatever fraction deemed necessary) for the Western blot with the antibody against the protein of interest. The researcher should anticipate seeing a strong streptavidin-HRP signal for the input lanes, virtually no signal for the flow-through lanes, a strong signal in the reaction (+GalT/+ket) eluent lane and virtually no signal in the control eluent lanes.

Part C. HRP-Streptavidin Western Blotting

Resolve proteins eluted off streptavidin-agarose beads by SDS-PAGE.

Transfer proteins to nitrocellulose membrane.

Rinse the membrane with TBS (pH 7.4).

Block with 5% BSA in TBS for 1 h at room temperature.

Incubate with HRP-streptavidin (Pierce) 1:20,000 in TBS-Tween 0.05% for 1 h at room temperature.

Rinse twice with TBS-Tween 0.05%

Wash 6×10 min with TBS-Tween 0.05% at room temperature

Visualize biotinylated proteins by enhanced chemiluminescence

Although the invention has been described with reference to embodiments and examples, it should be understood that various modifications can be made without departing from the spirit of the invention. Accordingly, the invention is limited only by the following claims. All references cited herein are hereby expressly incorporated by reference.

REFERENCES (1) (a) Varki, A. *Glycobiology* 1993, 3, 97-130. (b) Lasky, L. A. *Annu. Rev. Biochem.* 1995, 64, 113-139. (c) Capila, I.; Linhardt, R. J. *Angew. Chem., Int. Ed.* 2002, 41, 391-412. (d) Rudd, P. M.; Elliott, T.; Cresswell, P.; Wilson, I. A.; Dwek, R. A. *Science* 2001, 291, 2370-2376.

(2) For reviews: (a) Wells, L.; Vosseller, K.; Hart, G. W. *Science* 2001, 291, 2376-2378. (b) Zachara, N. E.; Hart, G. W. *Chem. Rev.* 2002, 102, 431.

(3) Roquemore, E. P.; Chou, T. Y.; Hart, G. W. *Methods Enzymol.* 1994, 230, 443-460.

(4) Snow, C. M.; Senior, A.; Gerace, L. *J. Cell Biol.* 1987, 104, 1143-1156.

(5) Comer, F. I.; Vosseller, K.; Wells, L.; Accavitti, M. A.; Hart, G. W. *Anal. Biochem.* 2001, 293, 169-177.

(6) (a) Qian, X.; Sujino, K.; Palcic, M. M.; Ratcliffe, R. M. In *Glycochemistry: Principles, Synthesis, and Application*; Wang, P. G., Bertozzi, C. R., Eds.; Marcel Dekker, Inc.: New York, 2001; pp 535-565. (b) Wong, C. H.; Halcomb, R. L.; Ichikawa, Y.; Kajimoto, T. *Angew. Chem., Int. Ed.* 1995, 34, 521-546.

(7) Ramakrishnan, B.; Qasba, P. K. *J. Biol. Chem.* 2002, 277, 20833-20839.

(8) Hang, H. C.; Bertozzi, C. R. *J. Am. Chem. Soc.* 2001, 123, 1242-1243.

(9) Sim, M. M.; Kondo, H.; Wong, C. H. *J. Am. Chem. Soc.* 1993, 115, 2260-2267.

(10) Ha, S.; Chang, E.; Lo, M. C.; Men, H.; Park, P.; Ge, M.; Walker, S. *J. Am. Chem. Soc.* 1999, 121, 8415-8426.

(11) Wittmann, V.; Wong, C. H. *J. Org. Chem.* 1997, 62, 2144-2147.

(12) Lamarre-Vincent, N.; Hsieh-Wilson, L. C. *J. Am. Chem. Soc.* 2003, 125, 6612-6613.

(13) (a) Chalkley, R. J.; Burlingame, A. L. *J. Am. Soc. Mass Spectrom.* 2001, 12, 1106-1113. (b) Haynes, P. A.; Aebersold, R. *Anal. Chem.* 2000, 72, 5402-5410.

(14) Vocadlo, D. J.; Hang, H. C.; Kim, E. J.; Hanover, J. A.; Bertozzi, C. R. *Proc. Natl. Acad. Sci. U.S.A.* 2003, 100, 9116-9121.

(15) Seitz, O.; Wong, C. H. *J. Am. Chem. Soc.* 1997, 119, 8766-8776.

(16) Lamarre-Vincent, N.; Hsieh-Wilson, L. C. *J. Am. Chem. Soc.* 2003, 125, 6612-6613.

(17) Arts, J.; Herr, I.; Lansink, M.; Angel, P.; Kooistra, T. *Nucleic Acids Res.* 1997, 25, 311-317.

(18) Ramakrishnan, B.; Qasba, P. K. *J. Biol. Chem.* 2002, 277, 20833-20839.

(19) Ross, A. J.; Ivanova, I. A.; Ferguson, M. A. J.; Nikolaev, A. V. *J. Chem. Soc.-Perkin Trans.* 1 2001, 72-81.

(20) a) Ha, S.; Chang, E.; Lo, M. C.; Men, H.; Park, P.; Ge, M.; Walker, S. *J. Am. Chem. Soc.* 1999, 121, 8415-8426. (b) Sim, M. M.; Kondo, H.; Wong, C. H. *J. Am. Chem. Soc.* 1993, 115, 2260-2267.

(21) (a) Wittmann, V.; Wong, C. H. *J. Org. Chem.* 1997, 62, 2144-2147. (b) Hitchcock, S. A.; Eid, C. N.; Aikins, J. A.; Zia-Ebrahimi, M.; Blaszczak, L. C. *J. Am. Chem. Soc.* 1998, 120, 1916-1917.

(22) Unverzagt, C.; Kunz, H.; Paulson, J. C. *J. Am. Chem. Soc.* 1990, 112, 9308-9309.

(23) Glass, W. F.; Briggs, R. C.; Hnilica, L. S. *Anal. Biochem.* 1981, 115, 219-224.

(24) Roquemore, E. P.; Dell, A.; Morris, H. R.; Panico, M.; Reason, A. J.; Savoy, L. A.; Wistow, G. J.; Zigler, J. S.; Earles, B. J.; Hart, G. W. *J. Biol. Chem.* 1992, 267, 555-563.

(25) Roquemore, E. P.; Chou, T. Y.; Hart, G. W. *Methods Enzymol.* 1994, 230, 443-460.

(26) Konrad, R. J.; Janowski, K. M.; Kudlow, J. E. *Biochem. Biophys. Res. Commun.* 2000, 267, 26-32.

(27) Freeze, H. H. In *Current Protocols in Molecular Biology*; Ausubel, F. M., Brent, R., Kingston, R. E., Moore, D. D., Seidman, J. G., Smith, J. A., Struhl, K., Eds.; John Wiley & Sons, Inc.: New York, 1999; Vol. 3, pp 17.7.1-17.7.8.

(28) (a) Zachara, N. E.; Hart G. W. *Chem. Rev.* 2002, 102, 431-438. (b) Wells, L.; Vosseller, K.; Hart, G. W. *Science* 2001, 291, 3376-2378.

(29) (a) Wells, L.; Vosseller, K.; Cole, R. N.; Cronshaw, J. M.; Matunis, M. J.; Hart, G. W. *Mol. Cell, Proteomics* 2002, 1, 791-804, (b) Vocadlo, D. J.; Hang, H. C.; Kim, E. J.; Hanover, J. A.; Bertozzi, C. R. *Proc. Natl. Acad. Sci. U.S.A.* 2003, 100, 9116-9121. (c) Comer, F. I.; Vosseller, K.; Wells, L.; Accavitti, M. A.; Hart G. W. *Anal. Biochem.* 2001, 293, 169-177.

(30) (a) Zhang, F.; Su, K.; Yang, X.; Bowe, D. B.; Paterson, A. J.; Kudlow, J. E. *Cell* 2003, 115, 715-725; (b) Chou, T. Y.; Dang, C. V.; Hart, G. W. *Proc. Natl. Acad. Sci. U.S.A.* 1995, 92, 4417-4421.

(31) Khidekel, N.; Arndt, S.; Lamarre-Vincent, N.; Lippert, A.; Poulin-Kerstien, K. G.; Ramakrishnan, B, Qasba, P. K.; Hsieh-Wilson, L. C. *J. Am. Chem. Soc.* 2003, 125, 16162-16163.

(32) Notably, the strategy has been successfully applied to brain tissue and several mammalian cell lines.

(33) Roquemore, E. P.; Chou, T. Y.; Han, G. W. *Methods Enzymol*, 1994, 230, 443-460.

(34) Lamarre-Vincent, N.; Hsieh-Wilson, L. C. *J. Am. Chem. Soc.* 2003, 125, 6612-6613.

(35) Lubas, W. A.; Hanover, J. A. *J. Biol. Chem.* 2000, 275, 10983-10988.

(36) Jackson, S. P.; Tjian, R. *Cell* 1988, 55, 125-133.

(37) Mayr, B.; Montminy, M. *Nat. Rev. Mol. Cell. Biol.* 2001, 2, 599-609.

(38) Vo, N.; Goodman, R. H. *J. Biol. Chem.*, 2001, 276, 13505-13508.
(39) Yang, X.; Zhang, F.; Kudlow, J. E. *Cell* 2002, 110, 69-80.
(40) Aebersold, R.; Mann, M. *Nature* 2003, 422, 198-207.
(41) Ramakrishnan, B.; Qasba, P. K. *J. Biol. Chem.* 2002, 277, 20833-20839.
(42) Wang, Y.; Falasca, M.; Schlessinger, J.; Malstrom, S.; Tsichlis, P.; Settleman, J.; Hu, W.; Lim, B.; Prywes, R. *Cell Growth Differ.* 1998, 9, 513-522.
(43) Tarentino, A. L.; Plummer, T. H., Jr. *Methods Enzymol.* 1994, 230, 44-57.
(44) Roquemore, E. P.; Chou, T. Y.; Hart, G. W. *Methods Enzymol.* 1994, 230, 443-460.
(45) An, H. J.; Peavy, T. R.; Hedrick, J. L.; Lebrilla, C. B. *Anal. Chem.* 2003, 75, 5628-5637.
(46) Kunkel, J. P.; Jan, D. C.; Jamieson, J. C.; Butler, M. *J. Biotechnol.* 1998, 62, 55-71.
(47) Lamarre-Vincent, N.; Hsieh-Wilson, L. C. *J. Am. Chem. Soc.* 2003, 125, 6612-6613.
(48) hevchenko, A.; Wilm, M.; Vorm, O.; Mann, M. *Anal. Chem.* 1996, 68, 850-858.
(49) Licklider, L. J.; Thoreen, C. C.; Peng, J.; Gygi, S. P. *Anal. Chem.* 2002, 74, 3076-3083.
(50) Eng, J. K.; McCormack, A. L.; Yates, J. R., III *J. Am. Soc. Mass Spectrom.* 1994, 5, 976-989.
(51) Greengard, P. (2001) *Science* 294, 1024-30.
(52) Jenuwein, T. & Allis, C. D. (2001) *Science* 293, 1074-80.
(53) Wells, L., Vosseller, K. & Hart, G. W. (2001) *Science* 291, 2376-8.
(54) Slawson, C. & Hart, G. W. (2003) *Curr. Opin. Struct. Biol.* 13, 631-6.
(55) Whelan, S. A. & Hart, G. W. (2003) *Circ. Res.* 93, 1047-58.
(56) Zhang, F., Su, K., Yang, X., Bowe, D. B., Paterson, A. J. & Kudlow, J. E. (2003) *Cell* 115, 715-25.
(57) Griffith, L. S. & Schmitz, B. (1999) *Eur. J. Biochem.* 262, 824-31.
(58) Iyer, S. P. N. & Hart, G. W. (2003) *Biochemistry* 42, 2493-2499.
(59) Lamarre-Vincent, N. & Hsieh-Wilson, L. C. (2003) *J. Am. Chem. Soc.* 125, 6612-3.
(60) Cole, R. N. & Hart, G. W. (2001) *J. Neurochem:* 79, 1080-9.
(61) Roquemore, E. P., Chou, T. Y. & Hart, G. W. (1994) *Methods Enzymol.* 230, 443-60.
(62) Wells, L., Vosseller, K., Cole, R. N., Cronshaw, J. M., Matunis, M. J. & Hart, G. W. (2002) *Mol. Cell. Proteomics* 1, 791-804.
(63) Cieniewski-Bernard, C., Bastide, B., Lefebvre, T., Lemoine, J., Mounier, Y. & Michalski, J. C. (2004) *Mol. Cell. Proteomics.*
(64) Vocadlo, D. J., Hang, H. C., Kim, E. J., Hanover, J. A. & Bertozzi, C. R. (2003) *Proc. Natl. Acad. Sci. USA* 100, 9116-21.
(65) Khidekel, N., Arndt, S., Lamarre-Vincent, N., Lippert, A., Poulin-Kerstien, K. G., Ramakrishnan, B., Qasba, P. K. & Hsieh-Wilson, L. C. (2003) *J. Am. Chem. Soc.* 125, 16162-3.
(66) Ramakrishnan, B. & Qasba, P. K. (2002) *J. Biol. Chem.* 277, 20833-9.
(67) Shevchenko, A., Wilm, M., Vorm, O. & Mann, M. (1996) *Anal. Chem.* 68, 850-8.
(68) Dignam, J. D., Lebovitz, R. M. & Roeder, R. G. (1983) *Nucleic Acids Res.* 11, 1475-89.
(69) Licklider, L. J., Thoreen, C. C., Peng, J. & Gygi, S. P. (2002) *Anal. Chem.* 74, 3076-83.
(70) Eng, J. K. M., A. L.; Yates, J. R., III (1994) *J. Am. Soc. Mass Spectrom.* 5, 976-989.
(71) Kalume, D. E., Molina, H. & Pandey, A. (2003) *Curr. Opin. Chem. Biol.* 7, 64-9.
(72) Chalkley, R. J. & Burlingame, A. L. (2001) *J. Am. Soc. Mass Spectrom.* 12, 1106-13.
(73) Haynes, P. A. & Aebersold, R. (2000) *Anal. Chem.* 72, 5402-5410.
(74) Ding, M. & Vandre, D. D. (1996) *J. Biol. Chem.* 271, 12555-61.
(75) Wysocka, J., Myers, M. P., Laherty, C. D., Eisenman, R. N. & Herr, W. (2003) *Genes Dev.* 17, 896-911.
(76) Inaba, M. & Maede, Y. (1989) *J. Biol. Chem.* 264, 18149-55.
(77) Schoof, H., Zaccaria, P., Gundlach, H., Lemcke, K., Rudd, S., Kolesov, G., Arnold, R., Mewes, H. W. & Mayer, K. F. (2002) *Nucleic Acids Res.* 30, 91-3.
(78) Oda, Y., Nagasu, T. & Chait, B. T. (2001) *Nat. Biotechnol.* 19, 379-82.
(79) Kelly, W. G., Dahmus, M. E. & Hart, G. W. (1993) *J. Biol. Chem.* 268, 10416-24.
(80) Gewinner, C., Hart, G., Zachara, N., Cole, R., Beisenherz-Huss, C. & Groner, B. (2004) *J. Biol. Chem.* 279, 3563-72.
(81) Pevny, L. H. & Lovell-Badge, R. (1997) *Curr. Opin. Genet. Dev.* 7, 338-44.
(82) Gure, A. O., Stockert, E., Scanlan, M. J., Keresztes, R. S., Jager, D., Altorki, N. K., Old, L. J. & Chen, Y. T. (2000) *Proc. Natl. Acad. Sci. USA* 97, 4198-203.
(83) Herdegen, T. & Leah, J. D. (1998) *Brain Res. Brain Res. Rev.* 28, 370-490.
(84) Kawasaki, H., Schiltz, L., Chiu, R., Itakura, K., Taira, K., Nakatani, Y. & Yokoyama, K. K. (2000) *Nature* 405, 195-200.
(85) Ban, N., Yamada, Y., Someya, Y., Ihara, Y., Adachi, T., Kubota, A., Watanabe, R., Kuroe, A., Inada, A., Miyawaki, K., Sunaga, Y., Shen, Z. P., Iwakura, T., Tsukiyama, K., Toyokuni, S., Tsuda, K. & Seino, Y. (2000) *Diabetes* 49, 1142-8.
(86) Lee, M. Y., Jung, C. H., Lee, K., Choi, Y. H., Hong, S. & Cheong, J. (2002) *Diabetes* 51, 3400-7.
(87) Collart, M. A. (2003) *Gene* 313, 1-16.
(88) Xu, J. & Li, Q. (2003) *Mol. Endocrinol.* 17, 1681-92.
(89) Yang, X., Zhang, F. & Kudlow, J. E. (2002) *Cell* 110, 69-80.
(90) Rebhun, J. F., Castro, A. F. & Quilliam, L. A. (2000) *J. Biol. Chem.* 275, 34901-8.
(91) Zhang, M. & Wang, W. (2003) *Acc. Chem. Res.* 36, 530-8.
(92) Wilson, F. H., Disse-Nicodeme, S., Choate, K. A., Ishikawa, K., Nelson-Williams, C., Desitter, I., Gunel, M., Milford, D. V., Lipkin, G. W., Achard, J. M., Feely, M. P., Dussol, B., Berland, Y., Unwin, R. J., Mayan, H., Simon, D. B., Farfel, Z., Jeunemaitre, X. & Lifton, R. P. (2001) *Science* 293, 1107-12.
(93) Deller, T., Korte, M., Chabanis, S., Drakew, A., Schwegler, H., Stefani, G. G., Zuniga, A., Schwarz, K., Bonhoeffer, T., Zeller, R., Frotscher, M. & Mundel, P. (2003) *Proc. Natl. Acad. Sci. USA* 100, 10494-9.
(94) Altrock, W. D., tom Dieck, S., Sokolov, M., Meyer, A. C., Sigler, A., Brakebusch, C., Fassler, R., Richter, K., Boeckers, T. M., Potschka, H., Brandt, C., Loscher, W., Grimberg, D., Dresbach, T., Hempelmann, A., Hassan, H., Balschun, D., Frey, J. U., Brandstatter, J. H., Garner, C. C., Rosenmund, C. & Gundelfinger, E. D. (2003) *Neuron* 37, 787-800.

(95) Nelly Khidekel, Sabine Arndt, Nathan Lamarre-Vincent, Alexander Lippert, Katherine G. Poulin-Kerstien, Boopathy Ramakrishnan, Pradman K. Qasba and Linda C. Hsieh-Wilson, *J. Am. Chem. Soc.* 125, 16162-16163 (2003); "A Chemoenzymatic Approach Toward the Rapid and Sensitive Detection of O-GlcNAc Posttranslational Modifications," Nelly Khidekel, Sabine Arndt, Nathan Lamarre-Vincent, Alexander Lippert, Katherine G. Poulin-Kerstien, Boopathy Ramakrishnan, Pradman K. Qasba and Linda C. Hsieh-Wilson, *J. Am. Chem. Soc.* Supporting Information, S1-S6 (2003).

(96) Hwan-Ching Tai, Nelly Khidekel, Scott B. Ficarro, Eric C. Peters, and Linda C. Hsieh-Wilson, *J. Am. Chem. Soc.*, 126, 10500-10501 (2004); "Parallel Identification of O-GlcNAc Modified Proteins from Cell Lysates," Hwan-Ching Tai, Nelly Khidekel, Scott B. Ficarro, Eric C. Peters, and Linda C. Hsieh-Wilson, *J. Am. Chem. Soc.*, Supporting Information, S1-S14.

(97) Nelly Khidekel, Scott B. Ficarro, Eric C. Peters, Linda C. Hsieh-Wilson, *Proc. Natl. Acad. Sci. U.S.A.*, 101 (36), 13132-13137; "Exploring the O-GlcNAc Proteome: Direct Identification of O-GlcNAc-Modified Proteins," Nelly Khidekel, Scott B. Ficarro, Eric C. Peters, Linda C. Hsieh-Wilson, *Proc. Natl. Acad. Sci. U.S.A.*, Supporting Information.

(98) Jhala U S, Canettieri G, Screaton R A, Kulkami R N, Krajewski S, Reed J, Walker J, Lin X, White M, Montminy M. cAMP promotes pancreatic beta-cell survival via CREB-mediated induction of IRS2. Genes Dev. 2003 Jul. 1; 17(13):1575-80.

(99) Herzig S, Long F, Jhala U S, Hedrick S, Quinn R, Bauer A, Rudolph D, Schutz G, Yoon C, Puigserver P, Spiegelman B, Montminy M. CREB regulates hepatic gluconeogenesis through the coactivator PGC-1. Nature. 2001 Sep. 13; 413(6852):179-83. Erratum in: Nature 2001 Oct. 11; 413(6856):652.

(100) Wells L, Vosseller K, Hart G W. A role for N-acetylglucosamine as a nutrient sensor and mediator of insulin resistance. Cell Mol Life Sci. 2003 February; 60(2):222-8. Review.

(101) Liu K, Paterson A J, Chin E, Kudlow J E. Glucose stimulates protein modification by O-linked GlcNAc in pancreatic beta cells: linkage of O-linked GlcNAc to beta cell death. Proc Natl Acad Sci USA. 2000 Mar. 14; 97(6): 2820-5.

(102) CREB and neurodegeneration. Front Biosci. 2004 Jan. 1; 9:100-3.

(103) CREB family transcription factors inhibit neuronal suicide. Nat Med. 2002 May; 8(5):450-1.

(104) Mantamadiotis T, Lemberger T, Bleckmann S C, Kern H, Kretz O, Martin Villalba A, Tronche F, Kellendonk C, Gau D, Kapfhammer J, Otto C, Schmid W, Schutz G. Disruption of CREB function in brain leads to neurodegeneration. Nat Genet. 2002 May; 31(1):47-54.

(105) Eferl R, Wagner E F. AP-1: a double-edged sword in tumorigenesis. Nat Rev Cancer. 2003 November; 3(11): 859-68.

(106) van Dam H, Castellazzi M. Distinct roles of Jun:Fos and Jun:ATF dimers in oncogenesis. Oncogene. 2001 Apr. 30; 20(19):2453-64.

What is claimed is:

1. A compound of the formula:

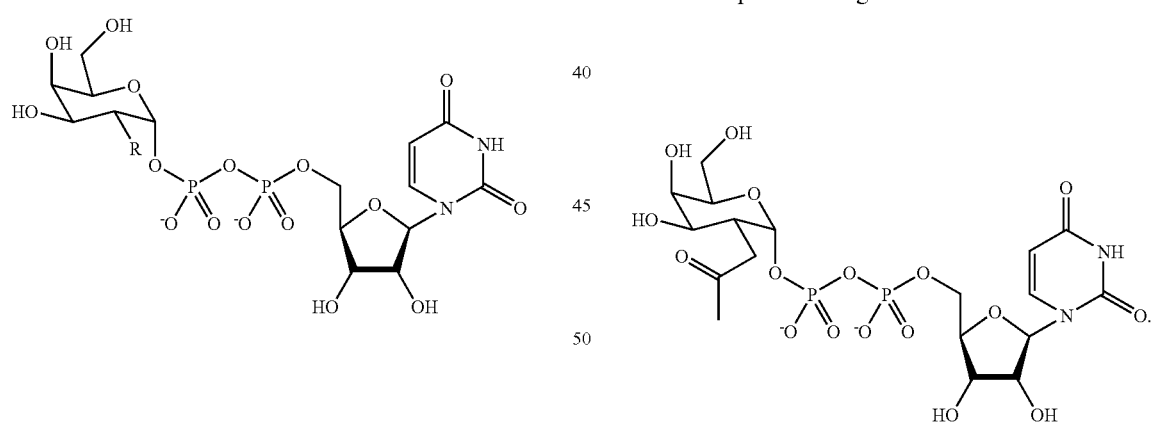

wherein R is a substituent selected from the group consisting of straight chain or branched $C_1$-$C_{12}$ carbon chain bearing a carbonyl group, straight chain or branched $C_1$-$C_{12}$ carbon chain bearing an azide group and straight chain or branched $C_1$-$C_{12}$ carbon chain bearing an alkyne; wherein the carbonyl group, azide group or alkyne is attached to a carbon atom of the carbon chain which is at least one carbon atom removed from the carbon atom of the carbon chain which is attached to the carbon atom of the glycosyl moiety.

2. The compound of claim 1, wherein R is selected from the group consisting of straight chain or branched $C_2$-$C_4$ carbon chain bearing a carbonyl group, straight chain or branched $C_2$-$C_4$ carbon chain bearing an azide group, and straight chain or branched $C_2$-$C_4$ carbon chain bearing an alkyne; wherein the carbonyl group, azide group or alkyne is attached to a carbon atom of the carbon chain which is at least one carbon atom removed from the carbon atom of the carbon chain which is attached to the carbon atom of the glycosyl moiety.

3. The compound having the formula

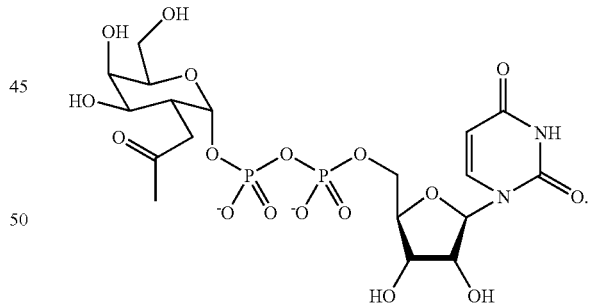

4. The compound of claim 1, wherein R is a straight chain or branched $C_1$-$C_{12}$ carbon chain bearing a carbonyl group, wherein the carbonyl group is attached to a carbon atom of the carbon chain which is at least one carbon atom removed from the carbon atom of the carbon chain attached to the carbon atom of the glycosyl moiety.

5. The compound of claim 4, wherein R is a straight chain $C_1$-$C_{12}$ carbon chain bearing a carbonyl group, wherein the carbonyl group is attached to a carbon atom of the carbon chain which is at least one carbon atom removed from the carbon atom of the carbon chain which is attached to the carbon atom of the glycosyl moiety.

6. The compound of claim 2, wherein R is a straight chain or branched $C_2$-$C_4$ carbon chain bearing a carbonyl group, wherein the carbonyl group is attached to a carbon atom of the carbon chain which is at least one carbon atom removed the carbon atom of the carbon chain which is attached to the carbon atom of the glycosyl moiety.

7. The compound of claim 6, wherein R is a straight chain $C_2$-$C_4$ carbon chain bearing a carbonyl group, wherein the carbonyl group is attached to a carbon atom of the carbon chain which is at least one carbon atom removed the carbon atom of the carbon chain which is attached to the carbon atom of the glycosyl moiety.

* * * * *

```
SEQUENCE LISTING

<160> NUMBER OF SEQ ID NOS: 51

<210> SEQ ID NO 1
<211> LENGTH: 10
<212> TYPE: PRT
<213> ORGANISM: Artificial Sequence
<220> FEATURE:
<223> OTHER INFORMATION: Synthetically prepared peptide sequence
<220> FEATURE:
<221> NAME/KEY: CARBOHYD
<222> LOCATION: 5
<223> OTHER INFORMATION: O-linked N-acetylglucosamine

<400> SEQUENCE: 1

Thr Ala Pro Thr Ser Thr Ile Ala Pro Gly
1               5                   10

<210> SEQ ID NO 2
<211> LENGTH: 17
<212> TYPE: PRT
<213> ORGANISM: Homo sapiens
<220> FEATURE:
<221> NAME/KEY: MOD_RES
<222> LOCATION: 12
<223> OTHER INFORMATION: methione oxidation to the corresponding
      sulfoxide

<400> SEQUENCE: 2

Ile Ser Pro Thr Phe Ala Asp Ala Tyr Ser Asn Met Gly Asn Thr Leu
1               5                   10                  15

Lys
```

-continued

<210> SEQ ID NO 3
<211> LENGTH: 10
<212> TYPE: PRT
<213> ORGANISM: Homo sapiens

<400> SEQUENCE: 3

Ile Lys Pro Val Glu Val Thr Glu Ser Ala
1               5                   10

<210> SEQ ID NO 4
<211> LENGTH: 16
<212> TYPE: PRT
<213> ORGANISM: Bos taurus

<400> SEQUENCE: 4

Ala Ile Pro Val Ser Arg Glu Glu Lys Pro Ser Ser Ala Pro Ser Ser
1               5                   10                  15

<210> SEQ ID NO 5
<211> LENGTH: 15
<212> TYPE: PRT
<213> ORGANISM: Rattus norvegicus

<400> SEQUENCE: 5

Val Ser Gly His Ala Ala Val Thr Thr Pro Lys Val Tyr Ser Glu
1               5                   10                  15

<210> SEQ ID NO 6
<211> LENGTH: 19
<212> TYPE: PRT
<213> ORGANISM: Homo sapiens

<400> SEQUENCE: 6

Ala Pro Val Gly Ser Val Val Ser Val Pro Ser His Ser Ser Ala Ser
1               5                   10                  15

Ser Asp Lys

<210> SEQ ID NO 7
<211> LENGTH: 29
<212> TYPE: PRT
<213> ORGANISM: Rattus norvegicus

<400> SEQUENCE: 7

Thr Ala Pro Thr Ser Thr Ile Ala Pro Gly Val Val Met Ala Ser Ser
1               5                   10                  15

Pro Ala Leu Pro Thr Gln Pro Ala Glu Glu Ala Ala Arg
            20                  25

<210> SEQ ID NO 8
<211> LENGTH: 20
<212> TYPE: PRT
<213> ORGANISM: Homo sapiens

<400> SEQUENCE: 8

Ala Ile Gln Ile Asn Pro Ala Phe Ala Asp Ala His Ser Asn Leu Ala
1               5                   10                  15

Ser Ile His Lys
            20

<210> SEQ ID NO 9
<211> LENGTH: 14
<212> TYPE: PRT
<213> ORGANISM: Homo sapiens

```
<400> SEQUENCE: 9

Glu Met Gln Asp Val Gln Gly Ala Leu Gln Cys Tyr Thr Arg
1               5                   10

<210> SEQ ID NO 10
<211> LENGTH: 19
<212> TYPE: PRT
<213> ORGANISM: Homo sapiens

<400> SEQUENCE: 10

Ala Ile Gln Ile Asn Pro Ala Phe Ala Asp His Ser Asn Leu Ala Ser
1               5                   10                  15

Ile His Lys

<210> SEQ ID NO 11
<211> LENGTH: 7
<212> TYPE: PRT
<213> ORGANISM: Homo sapiens

<400> SEQUENCE: 11

Thr Ile Ile Val Thr Thr Arg
1               5

<210> SEQ ID NO 12
<211> LENGTH: 17
<212> TYPE: PRT
<213> ORGANISM: Rattus norvegicus

<400> SEQUENCE: 12

Thr Ile Thr Ser Glu Thr Thr Ser Thr Thr Thr Thr His Ile Thr
1               5                   10                  15

Lys

<210> SEQ ID NO 13
<211> LENGTH: 20
<212> TYPE: PRT
<213> ORGANISM: Homo sapiens

<400> SEQUENCE: 13

Thr Ala Gln Thr Ile Thr Ser Glu Thr Pro Ser Ser Thr Thr Thr Thr
1               5                   10                  15

Gln Ile Thr Lys
            20

<210> SEQ ID NO 14
<211> LENGTH: 16
<212> TYPE: PRT
<213> ORGANISM: Homo sapiens

<400> SEQUENCE: 14

Ser Glu Ala Ser Ser Ser Pro Pro Val Val Thr Ser Ser His Ser Arg
1               5                   10                  15

<210> SEQ ID NO 15
<211> LENGTH: 16
<212> TYPE: PRT
<213> ORGANISM: Homo sapiens

<400> SEQUENCE: 15

Ala Ala Leu Thr Gln Gln His Pro Pro Val Thr Asp Gly Thr Val Lys
1               5                   10                  15
```

<210> SEQ ID NO 16
<211> LENGTH: 26
<212> TYPE: PRT
<213> ORGANISM: Homo sapiens

<400> SEQUENCE: 16

Thr Ala Ala Ala Gln Val Gly Thr Ser Val Ser Ser Ala Ala Asn Thr
1               5                   10                  15

Ser Thr Arg Pro Ile Ile Thr Val His Lys
            20                  25

<210> SEQ ID NO 17
<211> LENGTH: 8
<212> TYPE: PRT
<213> ORGANISM: Homo sapiens

<400> SEQUENCE: 17

Val Met Ser Val Val Gln Thr Lys
1               5

<210> SEQ ID NO 18
<211> LENGTH: 9
<212> TYPE: PRT
<213> ORGANISM: Homo sapiens

<400> SEQUENCE: 18

Ser Pro Ile Thr Ile Ile Thr Thr Lys
1               5

<210> SEQ ID NO 19
<211> LENGTH: 17
<212> TYPE: PRT
<213> ORGANISM: Homo sapiens

<400> SEQUENCE: 19

Ile Asn Pro Ser Val Asn Pro Gly Ile Ser Pro Ala His Gly Val Thr
1               5                   10                  15

Arg

<210> SEQ ID NO 20
<211> LENGTH: 14
<212> TYPE: PRT
<213> ORGANISM: Homo sapiens

<400> SEQUENCE: 20

Ser Asn Pro Val Pro Ile Ser Ser Asn His Ser Ala Arg
1               5                   10

<210> SEQ ID NO 21
<211> LENGTH: 31
<212> TYPE: PRT
<213> ORGANISM: Homo sapiens

<400> SEQUENCE: 21

Ser Leu Ser Gln Gly Thr Gln Leu Pro Ser His Val Tyr Pro Thr Thr
1               5                   10                  15

Gly Val Pro Thr Met Ser Leu His Thr Pro Pro Ser Pro Ser Arg
            20                  25                  30

<210> SEQ ID NO 22
<211> LENGTH: 32
<212> TYPE: PRT
<213> ORGANISM: Homo sapiens

```
<400> SEQUENCE: 22

Thr Asp Ala Pro Thr Pro Gly Ser Asn Ser Thr Pro Gly Leu Arg Pro
1               5                   10                  15

Val Pro Gly Lys Pro Pro Gly Val Asp Pro Leu Ala Ser Ser Leu Arg
            20                  25                  30

<210> SEQ ID NO 23
<211> LENGTH: 12
<212> TYPE: PRT
<213> ORGANISM: Homo sapiens

<400> SEQUENCE: 23

Ala Gln Pro Ser Val Ser Leu Gly Ala Ala Tyr Arg
1               5                   10

<210> SEQ ID NO 24
<211> LENGTH: 9
<212> TYPE: PRT
<213> ORGANISM: Homo sapiens

<400> SEQUENCE: 24

Val Pro Val Thr Ala Thr Gln Thr Lys
1               5

<210> SEQ ID NO 25
<211> LENGTH: 16
<212> TYPE: PRT
<213> ORGANISM: Homo sapiens

<400> SEQUENCE: 25

Ala Gly Tyr Ser Gln Gly Ala Thr Gln Thr Gln Ala Gln Gln Ala Arg
1               5                   10                  15

<210> SEQ ID NO 26
<211> LENGTH: 19
<212> TYPE: PRT
<213> ORGANISM: Homo sapiens

<400> SEQUENCE: 26

Ala Pro Val Gly Ser Val Val Ser Val Pro Ser His Ser Ser Ala Ser
1               5                   10                  15

Ser Asp Lys

<210> SEQ ID NO 27
<211> LENGTH: 8
<212> TYPE: PRT
<213> ORGANISM: Homo sapiens

<400> SEQUENCE: 27

Val Pro Thr Thr Val Glu Asp Arg
1               5

<210> SEQ ID NO 28
<211> LENGTH: 17
<212> TYPE: PRT
<213> ORGANISM: Homo sapiens

<400> SEQUENCE: 28

Thr Ile Thr Ser Glu Thr Thr Ser Thr Thr Thr Thr His Ile Thr
1               5                   10                  15

Lys
```

<210> SEQ ID NO 29
<211> LENGTH: 19
<212> TYPE: PRT
<213> ORGANISM: Homo sapiens

<400> SEQUENCE: 29

Thr Thr Ser Thr Thr Thr Thr Thr His Ile Thr Lys Thr Val Gly Gly
1               5                   10                  15

Ile Ser Glu

<210> SEQ ID NO 30
<211> LENGTH: 23
<212> TYPE: PRT
<213> ORGANISM: Homo sapiens

<400> SEQUENCE: 30

Asp Val Leu Thr Ser Tyr Gly Ala Thr Ala Glu Thr Leu Ser Thr Ser
1               5                   10                  15

Thr Thr Thr His Val Thr Lys
            20

<210> SEQ ID NO 31
<211> LENGTH: 20
<212> TYPE: PRT
<213> ORGANISM: Homo sapiens

<400> SEQUENCE: 31

Thr Leu Ser Thr Ser Thr Thr Thr His Val Thr Lys Thr Val Lys Gly
1               5                   10                  15

Gly Phe Ser Glu
            20

<210> SEQ ID NO 32
<211> LENGTH: 15
<212> TYPE: PRT
<213> ORGANISM: Homo sapiens

<400> SEQUENCE: 32

His Asp Thr Ser Ala Ser Thr Gln Ser Thr Pro Ala Ser Ser Arg
1               5                   10                  15

<210> SEQ ID NO 33
<211> LENGTH: 16
<212> TYPE: PRT
<213> ORGANISM: Homo sapiens

<400> SEQUENCE: 33

Thr Thr Lys Thr Thr Arg Ser Pro Asp Thr Ser Ala Tyr Cys Tyr Glu
1               5                   10                  15

<210> SEQ ID NO 34
<211> LENGTH: 22
<212> TYPE: PRT
<213> ORGANISM: Homo sapiens

<400> SEQUENCE: 34

Ser Ser Lys Asp Glu Glu Pro Gln Lys Asp Lys Ala Asp Lys Val Ala
1               5                   10                  15

Asp Val Pro Val Ser Glu
            20

<210> SEQ ID NO 35
<211> LENGTH: 11

```
<212> TYPE: PRT
<213> ORGANISM: Homo sapiens

<400> SEQUENCE: 35

Lys Ala Asp Lys Val Ala Asp Val Pro Ser Glu
1               5                   10

<210> SEQ ID NO 36
<211> LENGTH: 11
<212> TYPE: PRT
<213> ORGANISM: Homo sapiens

<400> SEQUENCE: 36

Thr Ser Ser Glu Ser Pro Phe Pro Ala Lys Glu
1               5                   10

<210> SEQ ID NO 37
<211> LENGTH: 18
<212> TYPE: PRT
<213> ORGANISM: Homo sapiens

<400> SEQUENCE: 37

Asp Gly Thr Glu Val His Val Thr Ala Ser Ser Gly Ala Gly Val
1               5                   10                  15

Val Lys

<210> SEQ ID NO 38
<211> LENGTH: 20
<212> TYPE: PRT
<213> ORGANISM: Homo sapiens

<400> SEQUENCE: 38

Met Gly Gly Ser Thr Pro Ile Ser Ala Ala Ser Ala Thr Ser Leu Gly
1               5                   10                  15

His Phe Thr Lys
            20

<210> SEQ ID NO 39
<211> LENGTH: 23
<212> TYPE: PRT
<213> ORGANISM: Homo sapiens

<400> SEQUENCE: 39

Ile Ser Ser Arg Ser Ser Ile Val Ser Asn Ser Ser Phe Asp Ser Val
1               5                   10                  15

Pro Val Ser Leu His Asp Glu
            20

<210> SEQ ID NO 40
<211> LENGTH: 14
<212> TYPE: PRT
<213> ORGANISM: Homo sapiens

<400> SEQUENCE: 40

Ser Ser Phe Asp Ser Val Pro Val Ser Leu His Asp Glu Arg
1               5                   10

<210> SEQ ID NO 41
<211> LENGTH: 9
<212> TYPE: PRT
<213> ORGANISM: Homo sapiens

<400> SEQUENCE: 41
```

```
Ser Val Pro Val Ser Leu His Asp Glu
1               5
```

<210> SEQ ID NO 42
<211> LENGTH: 16
<212> TYPE: PRT
<213> ORGANISM: Homo sapiens

<400> SEQUENCE: 42

```
Val Ser Gly His Ala Ala Val Thr Thr Pro Thr Lys Val Tyr Ser Glu
1               5                   10                  15
```

<210> SEQ ID NO 43
<211> LENGTH: 7
<212> TYPE: PRT
<213> ORGANISM: Homo sapiens

<400> SEQUENCE: 43

```
Val Thr Gln His Phe Ala Lys
1               5
```

<210> SEQ ID NO 44
<211> LENGTH: 11
<212> TYPE: PRT
<213> ORGANISM: Homo sapiens

<400> SEQUENCE: 44

```
Ile Gly Gly Asp Leu Thr Ala Ala Val Thr Lys
1               5                   10
```

<210> SEQ ID NO 45
<211> LENGTH: 8
<212> TYPE: PRT
<213> ORGANISM: Homo sapiens

<400> SEQUENCE: 45

```
Glu Ala Ala Leu Pro Ser Thr Lys
1               5
```

<210> SEQ ID NO 46
<211> LENGTH: 13
<212> TYPE: PRT
<213> ORGANISM: Homo sapiens

<400> SEQUENCE: 46

```
Thr Val Thr Val Thr Lys Pro Thr Gly Val Ser Phe Lys
1               5                   10
```

<210> SEQ ID NO 47
<211> LENGTH: 10
<212> TYPE: PRT
<213> ORGANISM: Homo sapiens

<400> SEQUENCE: 47

```
Ile Gly Asp Val Thr Thr Ser Ala Val Lys
1               5                   10
```

<210> SEQ ID NO 48
<211> LENGTH: 341
<212> TYPE: PRT
<213> ORGANISM: Rattus norvegicus

<400> SEQUENCE: 48

```
Met Thr Met Asp Ser Gly Ala Asp Asn Gln Gln Ser Gly Asp Ala Ala
1               5                   10                  15
```

```
Val Thr Glu Ala Glu Ser Gln Gln Met Thr Val Gln Ala Gln Pro Gln
             20                  25                  30

Ile Ala Thr Leu Ala Gln Val Ser Met Pro Ala Ala His Ala Thr Ser
             35                  40                  45

Ser Ala Pro Thr Val Thr Leu Val Gln Leu Pro Asn Gly Gln Thr Val
 50                  55                  60

Gln Val His Gly Val Ile Gln Ala Ala Gln Pro Ser Val Ile Gln Ser
 65                  70                  75                  80

Pro Gln Val Gln Thr Val Gln Ser Ser Cys Lys Asp Leu Lys Arg Leu
                 85                  90                  95

Phe Ser Gly Thr Gln Ile Ser Thr Ile Ala Glu Ser Glu Asp Ser Gln
                100                 105                 110

Glu Ser Val Asp Ser Val Thr Asp Ser Gln Lys Arg Arg Glu Ile Leu
            115                 120                 125

Ser Arg Arg Pro Ser Tyr Arg Lys Ile Leu Asn Asp Leu Ser Ser Asp
        130                 135                 140

Ala Pro Gly Val Pro Arg Ile Glu Glu Glu Lys Ser Glu Glu Glu Thr
145                 150                 155                 160

Ser Ala Pro Ala Ile Thr Thr Val Thr Val Pro Thr Pro Ile Tyr Gln
                165                 170                 175

Thr Ser Ser Gly Gln Tyr Ile Ala Ile Thr Gln Gly Gly Ala Ile Gln
            180                 185                 190

Leu Ala Asn Asn Gly Thr Asp Gly Val Gln Gly Leu Gln Thr Leu Thr
        195                 200                 205

Met Thr Asn Ala Ala Thr Gln Pro Gly Thr Thr Ile Leu Gln Tyr
    210                 215                 220

Ala Gln Thr Thr Asp Gly Gln Gln Ile Leu Val Pro Ser Asn Gln Val
225                 230                 235                 240

Val Val Gln Ala Ala Ser Gly Asp Val Gln Thr Tyr Gln Ile Arg Thr
                245                 250                 255

Ala Pro Thr Ser Thr Ile Ala Pro Gly Val Val Met Ala Ser Ser Pro
            260                 265                 270

Ala Leu Pro Thr Gln Pro Ala Glu Glu Ala Ala Arg Lys Arg Glu Val
        275                 280                 285

Arg Leu Met Lys Asn Arg Glu Ala Ala Arg Glu Cys Arg Arg Lys Lys
        290                 295                 300

Lys Glu Tyr Val Lys Cys Leu Glu Asn Arg Val Ala Val Leu Glu Asn
305                 310                 315                 320

Gln Asn Lys Thr Leu Ile Glu Glu Leu Lys Ala Leu Lys Asp Leu Tyr
                325                 330                 335

Cys His Lys Ser Asp
            340

<210> SEQ ID NO 49
<211> LENGTH: 1036
<212> TYPE: PRT
<213> ORGANISM: Homo sapiens

<400> SEQUENCE: 49

Met Ala Ser Ser Val Gly Asn Val Ala Asp Ser Thr Gly Leu Ala Glu
 1               5                  10                  15

Leu Ala His Arg Glu Tyr Gln Ala Gly Asp Phe Glu Ala Ala Glu Arg
             20                  25                  30

His Cys Met Gln Leu Trp Arg Gln Glu Pro Asp Asn Thr Gly Val Leu
```

-continued

```
                35                  40                  45
Leu Leu Leu Ser Ser Ile His Phe Gln Cys Arg Arg Leu Asp Arg Ser
 50                  55                  60
Ala His Phe Ser Thr Leu Ala Ile Lys Gln Asn Pro Leu Leu Ala Glu
 65                  70                  75                  80
Ala Tyr Ser Asn Leu Gly Asn Val Tyr Lys Glu Arg Gly Gln Leu Gln
                 85                  90                  95
Glu Ala Ile Glu His Tyr Arg His Ala Leu Arg Leu Lys Pro Asp Phe
            100                 105                 110
Ile Asp Gly Tyr Ile Asn Leu Ala Ala Ala Leu Val Ala Ala Gly Asp
            115                 120                 125
Met Glu Gly Ala Val Gln Ala Tyr Val Ser Ala Leu Gln Tyr Asn Pro
130                 135                 140
Asp Leu Tyr Cys Val Arg Ser Asp Leu Gly Asn Leu Leu Lys Ala Leu
145                 150                 155                 160
Gly Arg Leu Glu Glu Ala Lys Ala Cys Tyr Leu Lys Ala Ile Glu Thr
                165                 170                 175
Gln Pro Asn Phe Ala Val Ala Trp Ser Asn Leu Gly Cys Val Phe Asn
            180                 185                 190
Ala Gln Gly Glu Ile Trp Leu Ala Ile His His Phe Glu Lys Ala Val
            195                 200                 205
Thr Leu Asp Pro Asn Phe Leu Asp Ala Tyr Ile Asn Leu Gly Asn Val
210                 215                 220
Leu Lys Glu Ala Arg Ile Phe Asp Arg Ala Val Ala Ala Tyr Leu Arg
225                 230                 235                 240
Ala Leu Ser Leu Ser Pro Asn His Ala Val Val His Gly Asn Leu Ala
                245                 250                 255
Cys Val Tyr Tyr Glu Gln Gly Leu Ile Asp Leu Ala Ile Asp Thr Tyr
            260                 265                 270
Arg Arg Ala Ile Glu Leu Gln Pro His Phe Pro Asp Ala Tyr Cys Asn
            275                 280                 285
Leu Ala Asn Ala Leu Lys Glu Lys Gly Ser Val Ala Glu Ala Glu Asp
290                 295                 300
Cys Tyr Asn Thr Ala Leu Arg Leu Cys Pro Thr His Ala Asp Ser Leu
305                 310                 315                 320
Asn Asn Leu Ala Asn Ile Lys Arg Glu Gln Gly Asn Ile Glu Glu Ala
                325                 330                 335
Val Arg Leu Tyr Arg Lys Ala Leu Glu Val Phe Pro Glu Phe Ala Ala
            340                 345                 350
Ala His Ser Asn Leu Ala Ser Val Leu Gln Gln Gln Gly Lys Leu Gln
            355                 360                 365
Glu Ala Leu Met His Tyr Lys Glu Ala Ile Arg Ile Ser Pro Thr Phe
370                 375                 380
Ala Asp Ala Tyr Ser Asn Met Gly Asn Thr Leu Lys Glu Met Gln Asp
385                 390                 395                 400
Val Gln Gly Ala Leu Gln Cys Tyr Thr Arg Ala Ile Gln Ile Asn Pro
                405                 410                 415
Ala Phe Ala Asp Ala His Ser Asn Leu Ala Ser Ile His Lys Asp Ser
            420                 425                 430
Gly Asn Ile Pro Glu Ala Ile Ala Ser Tyr Arg Thr Ala Leu Lys Leu
            435                 440                 445
Lys Pro Asp Phe Pro Asp Ala Tyr Cys Asn Leu Ala His Cys Leu Gln
450                 455                 460
```

```
Ile Val Cys Asp Trp Thr Asp Tyr Asp Glu Arg Met Lys Lys Leu Val
465                 470                 475                 480

Ser Ile Val Ala Asp Gln Leu Glu Lys Asn Arg Leu Pro Ser Val His
                485                 490                 495

Pro His His Ser Met Leu Tyr Pro Leu Ser His Gly Phe Arg Lys Ala
            500                 505                 510

Ile Ala Glu Arg His Gly Asn Leu Cys Leu Asp Lys Ile Asn Val Leu
        515                 520                 525

His Lys Pro Pro Tyr Glu His Pro Lys Asp Leu Lys Leu Ser Asp Gly
    530                 535                 540

Arg Leu Arg Val Gly Tyr Val Ser Ser Asp Phe Gly Asn His Pro Thr
545                 550                 555                 560

Ser His Leu Met Gln Ser Ile Pro Gly Met His Asn Pro Asp Lys Phe
                565                 570                 575

Glu Val Phe Cys Tyr Ala Leu Ser Pro Asp Asp Gly Thr Asn Phe Arg
            580                 585                 590

Val Lys Val Met Ala Glu Ala Asn His Phe Ile Asp Leu Ser Gln Ile
        595                 600                 605

Pro Cys Asn Gly Lys Ala Ala Asp Arg Ile His Gln Asp Gly Ile His
    610                 615                 620

Ile Leu Val Asn Met Asn Gly Tyr Thr Lys Gly Ala Arg Asn Glu Leu
625                 630                 635                 640

Phe Ala Leu Arg Pro Ala Pro Ile Gln Ala Met Trp Leu Gly Tyr Pro
                645                 650                 655

Gly Thr Ser Gly Ala Leu Phe Met Asp Tyr Ile Ile Thr Asp Gln Glu
            660                 665                 670

Thr Ser Pro Ala Glu Val Ala Glu Gln Tyr Ser Glu Lys Leu Ala Tyr
        675                 680                 685

Met Pro His Thr Phe Phe Ile Gly Asp His Ala Asn Met Phe Pro His
    690                 695                 700

Leu Lys Lys Lys Ala Val Ile Asp Phe Lys Ser Asn Gly His Ile Tyr
705                 710                 715                 720

Asp Asn Arg Ile Val Leu Asn Gly Ile Asp Leu Lys Ala Phe Leu Asp
                725                 730                 735

Ser Leu Pro Asp Val Lys Ile Val Lys Met Lys Cys Pro Asp Gly Gly
            740                 745                 750

Asp Asn Ala Asp Ser Ser Asn Thr Ala Leu Asn Met Pro Val Ile Pro
        755                 760                 765

Met Asn Thr Ile Ala Glu Ala Val Ile Glu Met Ile Asn Arg Gly Gln
    770                 775                 780

Ile Gln Ile Thr Ile Asn Gly Phe Ser Ile Ser Asn Gly Leu Ala Thr
785                 790                 795                 800

Thr Gln Ile Asn Asn Lys Ala Ala Thr Gly Glu Glu Val Pro Arg Thr
                805                 810                 815

Ile Ile Val Thr Thr Arg Ser Gln Tyr Gly Leu Pro Glu Asp Ala Ile
            820                 825                 830

Val Tyr Cys Asn Phe Asn Gln Leu Tyr Lys Ile Asp Pro Ser Thr Leu
        835                 840                 845

Gln Met Trp Ala Asn Ile Leu Lys Arg Val Pro Asn Ser Val Leu Trp
    850                 855                 860

Leu Leu Arg Phe Pro Ala Val Gly Glu Pro Asn Ile Gln Gln Tyr Ala
865                 870                 875                 880
```

```
Gln Asn Met Gly Leu Pro Gln Asn Arg Ile Ile Phe Ser Pro Val Ala
                885                 890                 895

Pro Lys Glu Glu His Val Arg Arg Gly Gln Leu Ala Asp Val Cys Leu
            900                 905                 910

Asp Thr Pro Leu Cys Asn Gly His Thr Thr Gly Met Asp Val Leu Trp
            915                 920                 925

Ala Gly Thr Pro Met Val Thr Met Pro Gly Glu Thr Leu Ala Ser Arg
930                 935                 940

Val Ala Ala Ser Gln Leu Thr Cys Leu Gly Cys Leu Glu Leu Ile Ala
945                 950                 955                 960

Lys Asn Arg Gln Glu Tyr Glu Asp Ile Ala Val Lys Leu Gly Thr Asp
                965                 970                 975

Leu Glu Tyr Leu Lys Lys Val Arg Gly Lys Val Trp Lys Gln Arg Ile
            980                 985                 990

Ser Ser Pro Leu Phe Asn Thr Lys Gln Tyr Thr Met Glu Leu Glu Arg
            995                 1000                1005

Leu Tyr Leu Gln Met Trp Glu His Tyr Ala Ala Gly Asn Lys Pro Asp
    1010                1015                1020

His Met Ile Lys Pro Val Glu Val Thr Glu Ser Ala
1025                1030                1035

<210> SEQ ID NO 50
<211> LENGTH: 173
<212> TYPE: PRT
<213> ORGANISM: Bos taurus

<400> SEQUENCE: 50

Met Asp Ile Ala Ile Gln His Pro Trp Phe Lys Arg Thr Leu Gly Pro
1               5                   10                  15

Phe Tyr Pro Ser Arg Leu Phe Asp Gln Phe Phe Gly Glu Gly Leu Phe
            20                  25                  30

Glu Tyr Asp Leu Leu Pro Phe Leu Ser Ser Thr Ile Ser Pro Tyr Tyr
        35                  40                  45

Arg Gln Ser Leu Phe Arg Thr Val Leu Asp Ser Gly Ile Ser Glu Val
    50                  55                  60

Arg Ser Asp Arg Asp Lys Phe Val Ile Phe Leu Asp Val Lys His Phe
65                  70                  75                  80

Ser Pro Glu Asp Leu Thr Val Lys Val Gln Glu Asp Phe Val Glu Ile
                85                  90                  95

His Gly Lys His Asn Glu Arg Gln Asp Asp His Gly Tyr Ile Ser Arg
            100                 105                 110

Glu Phe His Arg Arg Tyr Arg Leu Pro Ser Asn Val Asp Gln Ser Ala
        115                 120                 125

Leu Ser Cys Ser Leu Ser Ala Asp Gly Met Leu Thr Phe Ser Gly Pro
    130                 135                 140

Lys Ile Pro Ser Gly Val Asp Ala Gly His Ser Glu Arg Ala Ile Pro
145                 150                 155                 160

Val Ser Arg Glu Glu Lys Pro Ser Ser Ala Pro Ser Ser
                165                 170

<210> SEQ ID NO 51
<211> LENGTH: 175
<212> TYPE: PRT
<213> ORGANISM: Bos taurus

<400> SEQUENCE: 51
```

-continued

```
Met Asp Ile Ala Ile His His Pro Trp Ile Arg Arg Pro Phe Phe Pro
1               5                   10                  15

Phe His Ser Pro Ser Arg Leu Phe Asp Gln Phe Phe Gly Glu His Leu
                20              25                  30

Leu Glu Ser Asp Leu Phe Pro Ala Ser Thr Ser Leu Ser Pro Phe Tyr
        35              40                  45

Leu Arg Pro Pro Ser Phe Leu Arg Ala Pro Ser Trp Ile Asp Thr Gly
    50              55                  60

Leu Ser Glu Met Arg Leu Glu Lys Asp Arg Phe Ser Val Asn Leu Asp
65              70                  75                  80

Val Lys His Phe Ser Pro Glu Glu Leu Lys Val Lys Val Leu Gly Asp
                85              90                  95

Val Ile Glu Val His Gly Lys His Glu Glu Arg Gln Asp Glu His Gly
            100             105                 110

Phe Ile Ser Arg Glu Phe His Arg Lys Tyr Arg Ile Pro Ala Asp Val
        115             120                 125

Asp Pro Leu Ala Ile Thr Ser Ser Leu Ser Ser Asp Gly Val Leu Thr
    130             135                 140

Val Asn Gly Pro Arg Lys Gln Ala Ser Gly Pro Glu Arg Thr Ile Pro
145             150                 155                 160

Ile Thr Arg Glu Glu Lys Pro Ala Val Thr Ala Ala Pro Lys Lys
                165                 170                 175
```